(12) United States Patent
Benson et al.

(10) Patent No.: US 7,816,540 B2
(45) Date of Patent: *Oct. 19, 2010

(54) CARBOXYL- OR HYDROXYL-SUBSTITUTED BENZIMIDAZOLE DERIVATIVES

(75) Inventors: Gregory Martin Benson, Therwil (CH); Konrad Bleicher, Freiburg (DE); Uwe Grether, Efringen-Kirchen (DE); Bernd Kuhn, Reinach BL (CH); Rainer E. Martin, Basel (CH); Jean-Marc Plancher, Hagenthal-le-Bas (FR); Hans Richter, Grenzach-Wyhlen (DE); Sven Taylor, Riedisheim (FR); Minmin Yang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/331,461

(22) Filed: Dec. 10, 2008

(65) Prior Publication Data
US 2009/0163552 A1  Jun. 25, 2009

(30) Foreign Application Priority Data
Dec. 21, 2007   (EP)   ................... 07150351

(51) Int. Cl.
*A61K 31/4184* (2006.01)
*C07D 235/18* (2006.01)
(52) U.S. Cl. .................... 548/309.7; 514/394
(58) Field of Classification Search ............ 548/309.7
See application file for complete search history.

(56) References Cited
U.S. PATENT DOCUMENTS
2008/0021027 A1   1/2008   Benson et al.

FOREIGN PATENT DOCUMENTS
WO   WO 2007/081335   7/2007
WO   WO 2008/000643   1/2008

OTHER PUBLICATIONS

Gross et al., "The Peptides", vol. 2, pp. 365-381 (1980) Academic Press, NY.
Tempest et al., Tet. Lett., 42, pp. 4959-4962 (2001).
Tempest et al., Tet. Lett., 42, pp. 4963-4968 (2001).
Zhang et al., Tet. Lett., 45, pp. 6757-6760 (2004).
Bamford et al., Bioorganic & Medicinal Chemistry Letters, 15, pp. 3402-3406 (2005).
White, E.H., J. Am. Chem. Soc., 77, pp. 6011-6014 (1955).
Evans et al., Tetrahedron Lett., 38, pp. 4535-4538 (1997).
Larock, R.C., Comprehensive Organic Transformations, $2^{nd}$ Edition, John Wiley & Sons, New York, NY, pp. 1941-1949 (1999).

*Primary Examiner*—Laura L. Stockton
(74) *Attorney, Agent, or Firm*—George W. Johnston; Dennis P. Tramaloni; Brian C. Remy

(57) ABSTRACT

This invention relates to novel carboxyl- or hydroxyl-substituted benzimidazole derivatives of formula (I)

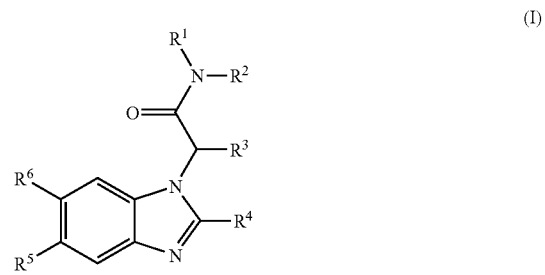

wherein $R^1$ to $R^6$ are as defined in the description and in the claims, as well as physiologically acceptable salts and esters thereof. These compounds bind to FXR and can be used as medicaments.

32 Claims, No Drawings

CARBOXYL- OR HYDROXYL-SUBSTITUTED BENZIMIDAZOLE DERIVATIVES

PRIORITY TO RELATED APPLICATION(S)

This application claims the benefit of European Patent Application No. 07150351.0, filed Dec. 21, 2007, which is hereby incorporated by reference in its entirety.

FIELD OF THE INVENTION

This invention is concerned with novel carboxyl- or hydroxyl-substituted benzimidazole derivatives, a process for the manufacture of these compounds, pharmaceutical preparations which contain such compounds as well as the use of these compounds for the production of pharmaceutical preparations.

BACKGROUND OF THE INVENTION

The Farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. (1999) Identification of a nuclear receptor for bile acids. Science 284, 1362-5]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXR alpha and blocks their transcriptional functions [Lu, T. T., Makishima, M., Repa, J. J., Schoonjans, K., Kerr, T. A., Auwerx, J. and Mangelsdorf, D. J. (2000) Molecular basis for feedback regulation of bile acid synthesis by nuclear receptors. Mol Cell 6, 507-15]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Tarr, P. T., Jones, S. A., Anisfeld, A. M., Stoltz, C. M., Tontonoz, P., Kliewer, S., Willson, T. M. and Edwards, P. A. (2002) Regulation of multidrug resistance-associated protein 2 (ABCC2) by the nuclear receptors pregnane X receptor, farnesoid X-activated receptor, and constitutive androstane receptor. J Biol Chem 277, 2908-15; Ananthanarayanan, M., Balasubramanian, N., Makishima, M., Mangelsdorf, D. J. and Suchy, F. J. (2001) Human bile salt export pump promoter is transactivated by the farnesoid X receptor/bile acid receptor. J Biol Chem 276, 28857-65]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. (2003) Hepatoprotection by the farnesoid X receptor agonist GW4064 in rat models of intra- and extra-hepatic cholestasis. J Clin Invest 112, 1678-87; Sinal, C. J., Tohkin, M., Miyata, M., Ward, J. M., Lambert, G. and Gonzalez, F. J. (2000) Targeted disruption of the nuclear receptor FXR/BAR impairs bile acid and lipid homeostasis. Cell 102, 731-44]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines the hydrophilicity of the bile acid pool and its ability to solubilize cholesterol. FXR activation increases the hydrophilicity of the pool, decreasing the intestinal solubilization of cholesterol, effectively blocking its absorption. Decrease absorption would be expected to result in lowering of plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. (2006) Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. J Biol Chem 281, 807-12]. FXR also decreases hepatic synthesis of triglycerides by repressing SREBP1-c expression by an alternate pathway involving SHP and LXRalpha. Thus compounds which modulate FXR activity may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol>240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple co-morbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

The novel compounds of the present invention exceed the compounds known in the art, inasmuch as they bind to and selectively modulate FXR very efficiently. Consequently, cholesterol absorption is reduced, LDL cholesterol and triglycerides are lowered, and inflammatory atherosclerosis is reduced. Since multiple facets of combined dyslipidemia and cholesterol homeostasis are addressed by FXR modulators, they are expected to have an enhanced therapeutic potential compared to the compounds already known in the art.

SUMMARY OF THE INVENTION

More specifically, the invention relates to novel benzimidazole derivatives of the formula (I)

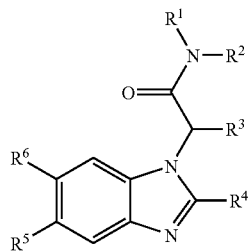

(I)

wherein
$R^1$ is selected from

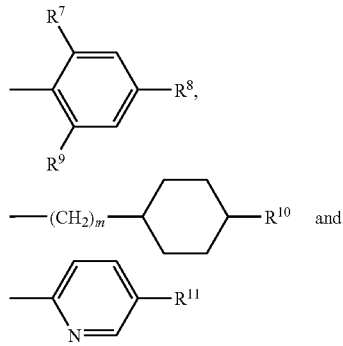

$R^2$ is hydrogen or lower alkyl;
$R^3$ is cyclohexyl or bicyclo[2.2.1]heptyl;
$R^4$ is phenyl which is substituted in 4-position by halogen, cyano or fluoro-lower alkyl, or pyridyl which is substituted with 1 or 2 substituents independently selected from halogen, amino, cyano and lower alkoxy;
$R^5$ and $R^6$ independently from each other are hydrogen or fluoro;
$R^7$ and $R^9$ independently from each other are selected from the group consisting of hydrogen, lower alkyl, halogen, lower alkoxy, fluoro-lower alkyl, fluoro-lower alkoxy and cyano;
$R^8$ is —$(CR^{12}R^{13})_n$—COOH wherein n is 0, 1 or 2 and $R^{12}$ and $R^{13}$ independently from each other are hydrogen or lower alkyl, or $R^{12}$ and $R^{13}$ together with the carbon atom they are attached to form a cycloalkyl ring,
or —O—$(CR^{14}R^{15})_p$—COOH wherein p is 1 or 2 and $R^{14}$ and $R^{15}$ independently from each other are hydrogen or lower alkyl, or $R^{14}$ and $R^{15}$ together with the carbon atom they are attached to form a cycloalkyl ring,
or $R^8$ is tetrazole;
$R^{10}$ is hydroxy or —$(CH_2)_p$—COOH wherein p is 0, 1 or 2;
M is 0 or 1;
$R^{11}$ is —COOH;

and pharmaceutically acceptable salts thereof.

The compounds are selective modulators of the farnesoid-X-receptor and are useful in the treatment or prophylaxis of diseases which are modulated by FXR agonists, particularly for the therapeutic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and/or Alzheimer's disease, which method comprises administering a compound of formula (I) to a human being or animal.

DETAILED DESCRIPTION OF THE INVENTION

A. Definitions

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "$C_{1-10}$-alkyl" refers to a branched or straight-chain monovalent saturated aliphatic hydrocarbon radical of one to ten carbon atoms, such as e.g. methyl, ethyl, n-propyl, isopropyl, n-butyl, s-butyl, t-butyl, pentyl, 1,1,3,3-tetramethyl-butyl and the like. Lower alkyl groups as described below also are preferred alkyl groups.

The term "lower alkyl" or "$C_1$-$C_7$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower alkyl groups can optionally be substituted, e.g. by hydroxy. Such substituted lower alkyl groups are referred to as "hydroxy-lower-alkyl".

The term "fluoro-lower alkyl" refers to lower alkyl groups which are mono- or multiply substituted with fluorine. Examples of fluoro-lower alkyl groups are e.g. —$CFH_2$, —$CF_2H$, —$CF_3$, —$CH_2CF_3$, —$(CH_2)_2CF_3$, —$CH(CF_3)_2$ and —$CF_2$—$CF_2H$.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "cycloalkyl" refers to a monovalent carbocyclic radical of 3 to 10 carbon atoms, preferably 3 to 7 carbon atoms, such as cyclopropyl, cyclobutyl, cyclopentyl, or cyclohexyl. A cycloalkyl group can optionally be substituted as described in the description and claims.

The term "alkoxy" refers to the group —O—R', wherein R' is an alkyl. The term "lower alkoxy" refers to the group —O—R', wherein R' is a lower alkyl. A preferred example is methoxy.

The term "fluoro-lower alkoxy" refers to the group R"—O—, wherein R" is fluoro-lower alkyl. Examples of fluoro-lower alkoxy groups are e.g. —O—CFH$_2$, —O—CF$_2$H, —O—CF$_3$, —O—CH$_2$CF$_3$, —O—(CH$_2$)$_2$CF$_3$, —O—CH(CF$_3$)$_2$, and —O—CF$_2$—CF$_2$H.

The term "protecting group" refers to groups which are used to protect functional groups, particularly hydroxy groups, temporarily. Examples of protecting groups are benzyl, p-methoxybenzyl, t-butyl-dimethylsilyl, t-butyl-diphenylsilyl and (for protection of amino groups) Boc and benzyloxycarbonyl.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and trimethylammonium salt. The term "pharmaceutically acceptable salts" also refers to such salts.

All references referred to herein are incorporated by reference in their entirety.

B. Detailed Description of the Invention

In detail, the present invention relates to compounds of formula (I)

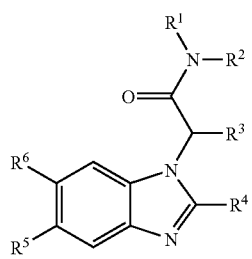

(I)

wherein
R$^1$ is selected from

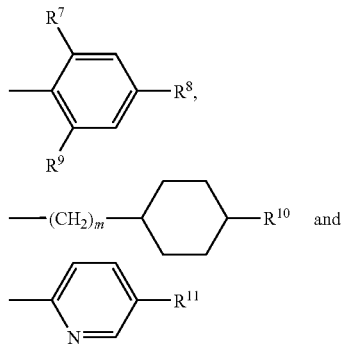

R$^2$ is hydrogen or lower alkyl;
R$^3$ is cyclohexyl or bicyclo[2.2.1]heptyl;
R$^4$ is phenyl which is substituted in 4-position by halogen, cyano or fluoro-lower alkyl, or pyridyl which is substituted with 1 or 2 substituents independently selected from halogen, amino, cyano and lower alkoxy;
R$^5$ and R$^6$ independently from each other are hydrogen or fluoro;
R$^7$ and R$^9$ independently from each other are selected from the group consisting of hydrogen, lower alkyl, halogen, lower alkoxy, fluoro-lower alkyl, fluoro-lower alkoxy and cyano;
R$^8$ is —(CR$^{12}$R$^{13}$)$_n$—COOH wherein n is 0, 1 or 2 and R$^{12}$ and R$^{13}$ independently from each other are hydrogen or lower alkyl, or R$^{12}$ and R$^{13}$ together with the carbon atom they are attached to form a cycloalkyl ring,
  or —O—(CR$^{14}$R$^{15}$)$_p$—COOH wherein p is 1 or 2 and R$^{14}$ and R$^{15}$ independently from each other are hydrogen or lower alkyl, or R$^{14}$ and R$^{15}$ together with the carbon atom they are attached to form a cycloalkyl ring, or R$^8$ is tetrazole;
R$^{10}$ is hydroxy or —(CH$_2$)$_p$—COOH wherein p is 0, 1 or 2;
m is 0 or 1;
R$^{11}$ is —COOH;

and pharmaceutically acceptable salts thereof.

Compounds of formula (I) are individually preferred and physiologically acceptable salts thereof are individually preferred, with the compounds of formula (I) being particularly preferred.

The compounds of formula (I) can have one or more asymmetric C atoms and can therefore exist as an enantiomeric mixture, diastereomeric mixture or as optically pure compounds.

In particular, preferred compounds are the compounds of formula (I) described in the examples as individual compounds as well as pharmaceutically acceptable salts as well as optically pure compounds thereof.

Preferred are the compounds of formula (I), wherein
R$^8$ is —(CR$^{12}$R$^{13}$)$_n$—COOH wherein n is 0, 1 or 2 and R$^{12}$ and R$^{13}$ independently from each other are hydrogen or lower alkyl, or R$^{12}$ and R$^{13}$ together with the carbon atom they are attached to form a cycloalkyl ring,
or —O—(CR$^{14}$R$^{15}$)$_p$—COOH wherein p is 1 or 2 and R$^{14}$ and R$^{15}$ independently from each other are hydrogen or lower alkyl, or R$^{14}$ and R$^{15}$ together with the carbon atom they are attached to form a cycloalkyl ring.

Preferred are further compounds of formula (I) according to the invention, wherein R$^2$ is hydrogen.

Especially preferred are furthermore compounds of formula (I) according to the present invention, wherein $R^3$ is cyclohexyl.

A group of preferred compounds of formula (I) are further those, wherein $R^4$ is phenyl which is substituted in 4-position by halogen, cyano or fluoro-lower alkyl, with those compounds of formula (I) being more preferred, wherein $R^4$ is 4-halogenphenyl. Most preferably, $R^4$ is 4-chlorophenyl.

Another group of preferred compounds of formula (I) are those, wherein $R^4$ is pyridyl which is substituted with 1 or 2 substituents independently selected from halogen, amino, cyano and lower alkoxy. More preferably, $R^4$ is pyridin-3-yl which is substituted with 1 or 2 substituents independently selected from halogen, amino, cyano and lower alkoxy. Most preferably, $R^4$ is 6-chloropyridin-3-yl or 2,6-dimethoxy-pyridin-3-yl.

Preferred are further compounds of formula (I) according to present invention, wherein $R^5$ and $R^6$ are fluoro.

A group of preferred compounds of formula (I) according to the invention are further those, wherein $R^1$ is

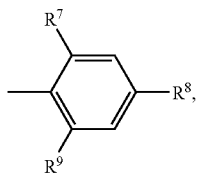

and wherein $R^7$ and $R^9$ independently from each other are selected from the group consisting of hydrogen, lower alkyl, halogen, lower alkoxy, fluoro-lower alkyl, fluoro-lower alkoxy and cyano; and $R^8$ is —$(CR^{12}R^{13})_p$—COOH wherein n is 0, 1 or 2 and $R^{12}$ and $R^{13}$ independently from each other are hydrogen or lower alkyl, or $R^{12}$ and $R^{13}$ together with the carbon atom they are attached to form a cycloalkyl ring, or —O—$(CR^{14}R^{15})_p$—COOH wherein p is 1 or 2 and $R^{14}$ and $R^{15}$ independently from each other are hydrogen or lower alkyl, or $R^{14}$ and $R^{15}$ together with the carbon atom they are attached to form a cycloalkyl ring.

This means, these are compounds of formula (I) having the formula

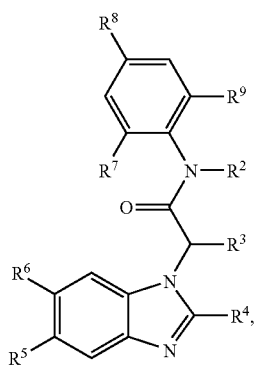

(I-i)

wherein $R^1$ to $R^9$ are as defined herein before.

Compounds of formula (I-i) are especially preferred, wherein $R^8$ is —$(CR^{12}R^{13})_p$—COOH, n is 0, 1 or 2 and $R^{12}$ and $R^{13}$ independently from each other are hydrogen or lower alkyl, or $R^{12}$ and $R^{13}$ together with the carbon atom they are attached to form a cycloalkyl ring. More preferably, $R^8$ is —COOH.

Also preferred are compounds of formula (I-i), wherein $R^8$ is —O—$(CR^{14}R^{15})_p$—COOH wherein p is 1 or 2 and $R^{14}$ and $R^{15}$ independently from each other are hydrogen or lower alkyl, or $R^{14}$ and $R^{15}$ together with the carbon atom they are attached to form a cycloalkyl ring. Especially preferred are those compounds, wherein p is 1. Especially preferred are compounds, wherein $R^{14}$ and $R^{15}$ are methyl or wherein $R^{14}$ and $R^{15}$ together with the carbon atom they are attached to form a cyclopropyl ring.

Another group of preferred compounds of formula (I) according to the invention are those, wherein $R^1$ is

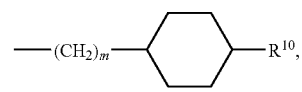

and wherein $R^{10}$ is hydroxy or —$(CH_2)_p$—COOH wherein p is 0, 1 or 2, and m is 0 or 1.

This means, these are compounds of formula (I) having the formula

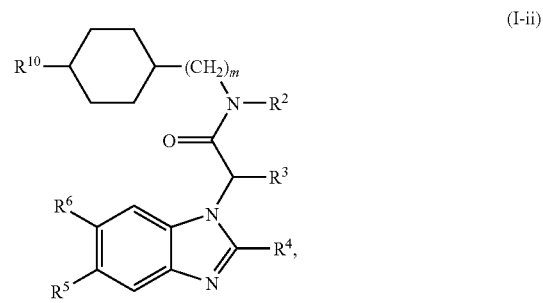

(I-ii)

wherein $R^1$ to $R^6$, $R^{10}$ and m are as defined herein before.

Preferred are compounds of formula (I-ii), wherein m is 0.

Further preferred compounds of formula (I-ii) according to the invention are those, wherein $R^{10}$ is hydroxy or —COOH. Especially preferred are those, wherein $R^{10}$ is hydroxy.

Furthermore, compounds of formula (I) according to the invention are preferred, wherein $R^1$ is

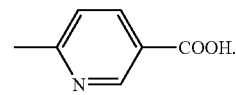

This means, these are compounds of formula (I) having the formula

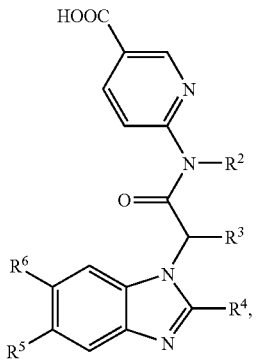

(I-iii)

wherein R$^1$ to R$^6$ are as defined herein before.

Preferred compounds of formula (I) are those selected from the group consisting of:

6-{2-[2-(6-chloro-pyridin-3-yl)-5,6-difluoro-benzoimidazol-1-yl]-2-cyclohexyl-acetylamino}-nicotinic acid,
3-chloro-4-{2-[2-(6-chloro-pyridin-3-yl)-5,6-difluoro-benzoimidazol-1-yl]-2-cyclohexyl-acetylamino}-benzoic acid,
4-{2-[2-(6-chloro-pyridin-3-yl)-5,6-difluoro-benzoimidazol-1-yl]-2-cyclohexyl-acetylamino}-3-fluoro-benzoic acid,
4-{2-[2-(6-chloro-pyridin-3-yl)-5,6-difluoro-benzoimidazol-1-yl]-2-cyclohexyl-acetylamino}-3-methyl-benzoic acid,
(−)-3-chloro-4-{2-[2-(6-chloro-pyridin-3-yl)-5,6-difluoro-benzoimidazol-1-yl]-2-cyclohexyl-acetylamino}-benzoic acid,
(+)-3-chloro-4-{2-[2-(6-chloro-pyridin-3-yl)-5,6-difluoro-benzoimidazol-1-yl]-2-cyclohexyl-acetylamino}-benzoic acid,
trans-4-{2-[2-(6-chloro-pyridin-3-yl)-5,6-difluoro-benzoimidazol-1-yl]-2-cyclohexyl-acetylamino}-cyclohexanecarboxylic acid,
2-cyclohexyl-2-[2-(2,6-dimethoxy-pyridin-3-yl)-5,6-difluoro-benzoimidazol-1-yl]-N-(4-hydroxy-cyclohexyl)-acetamide,
(+)-2-cyclohexyl-2-[2-(2,6-dimethoxy-pyridin-3-yl)-5,6-difluoro-benzoimidazol-1-yl]-N-(trans-4-hydroxy-cyclohexyl)-acetamide,
trans-4-({cyclohexyl[2-(2,6-dimethoxypyridin-3-yl)-5,6-difluoro-1H-benzimidazol-1-yl]acetyl}amino)cyclohexanecarboxylic acid,
(+)-4-{2-cyclohexyl-2-[2-(2,6-dimethoxy-pyridin-3-yl)-5,6-difluoro-benzoimidazol-1-yl]-acetylamino}-cyclohexanecarboxylic acid,
4-{2-cyclohexyl-2-[2-(2,6-dimethoxy-pyridin-3-yl)-5,6-difluoro-benzoimidazol-1-yl]-acetylamino}-3-methyl-benzoic acid,
4-{2-cyclohexyl-2-[2-(2,6-dimethoxy-pyridin-3-yl)-5,6-difluoro-benzoimidazol-1-yl]-acetylamino}-3-fluoro-benzoic acid,
4-{2-cyclohexyl-2-[2-(2,6-dimethoxy-pyridin-3-yl)-5-fluoro-benzoimidazol-1-yl]-acetylamino}-cyclohexanecarboxylic acid,
(−)-4-{2-cyclohexyl-2-[2-(2,6-dimethoxy-pyridin-3-yl)-5-fluoro-benzoimidazol-1-yl]-acetylamino}-cyclohexanecarboxylic acid,
(−)-4-{2-[2-(4-chloro-phenyl)-5,6-difluoro-benzoimidazol-1-yl]-2-cyclohexyl-acetylamino}-cyclohexanecarboxylic acid,
(4-{2-[2-(4-chloro-phenyl)-5,6-difluoro-benzoimidazol-1-yl]-2-cyclohexyl-acetylamino}-cyclohexyl)-acetic acid,
(+)-[trans-4-({2-[2-(4-chlorophenyl)-5,6-difluoro-1H-benzimidazol-1-yl]-2-cyclohexylacetyl}amino)cyclohexyl]acetic acid,
4-{2-bicyclo[2.2.1]hept-7-yl-2-[2-(4-chloro-phenyl)-5,6-difluoro-benzoimidazol-1-yl]-acetylamino}-benzoic acid,
(−)-trans-4-[({-2-[2-(4-chlorophenyl)-5-fluoro-1H-benzimidazol-1-yl]-2-cyclohexylacetyl}amino)methyl]cyclohexanecarboxylic acid,
3-chloro-4-{2-[2-(4-chloro-phenyl)-5-fluoro-benzoimidazol-1-yl]-2-cyclohexyl-acetylamino}-benzoic acid,
4-{2-[2-(4-chloro-phenyl)-5,6-difluoro-benzoimidazol-1-yl]-2-cyclohexyl-acetylamino}-benzoic acid,
(+)-4-{-2-[2-(4-chloro-phenyl)-5,6-difluoro-benzoimidazol-1-yl]-2-cyclohexyl-acetylamino}-benzoic acid,
(−)-4-{-2-[2-(4-chloro-phenyl)-5,6-difluoro-benzoimidazol-1-yl]-2-cyclohexyl-acetylamino}-benzoic acid,
4-{2-[2-(4-chloro-phenyl)-5,6-difluoro-benzoimidazol-1-yl]-2-cyclohexyl-acetylamino}-3-methyl-benzoic acid,
(+)-4-{-2-[2-(4-chloro-phenyl)-5,6-difluoro-benzoimidazol-1-yl]-2-cyclohexyl-acetylamino}-3-methyl-benzoic acid,
(−)-4-{-2-[2-(4-chloro-phenyl)-5,6-difluoro-benzoimidazol-1-yl]-2-cyclohexyl-acetylamino}-3-methyl-benzoic acid,
3-chloro-4-{2-[2-(4-chloro-phenyl)-5,6-difluoro-benzoimidazol-1-yl]-2-cyclohexyl-acetylamino}-benzoic acid,
(+)-3-chloro-4-{-2-[2-(4-chloro-phenyl)-5,6-difluoro-benzoimidazol-1-yl]-2-cyclohexyl-acetylamino}-benzoic acid,
(−)-3-chloro-4-{-2-[2-(4-chloro-phenyl)-5,6-difluoro-benzoimidazol-1-yl]-2-cyclohexyl-acetylamino}-benzoic acid,
4-{2-[2-(4-chloro-phenyl)-5,6-difluoro-benzoimidazol-1-yl]-2-cyclohexyl-acetylamino}-3-fluoro-benzoic acid,
(+)-4-{-2-[2-(4-chloro-phenyl)-5,6-difluoro-benzoimidazol-1-yl]-2-cyclohexyl-acetylamino}-3-fluoro-benzoic acid,
(−)-4-{-2-[2-(4-chloro-phenyl)-5,6-difluoro-benzoimidazol-1-yl]-2-cyclohexyl-acetylamino}-3-fluoro-benzoic acid,
4-{2-[2-(4-chloro-phenyl)-5,6-difluoro-benzoimidazol-1-yl]-2-cyclohexyl-acetylamino}-3,5-difluoro-benzoic acid,
(+)-4-{-2-[2-(4-chloro-phenyl)-5,6-difluoro-benzoimidazol-1-yl]-2-cyclohexyl-acetylamino}-3,5-difluoro-benzoic acid,
(−)-4-{-2-[2-(4-chloro-phenyl)-5,6-difluoro-benzoimidazol-1-yl]-2-cyclohexyl-acetylamino}-3,5-difluoro-benzoic acid,
4-{2-[2-(4-chloro-phenyl)-5,6-difluoro-benzoimidazol-1-yl]-2-cyclohexyl-acetylamino}-3-cyano-benzoic acid,
3-chloro-4-{2-[2-(4-chloro-phenyl)-benzoimidazol-1-yl]-2-cyclohexyl-acetylamino}-benzoic acid,
(+)-3-chloro-4-{-2-[2-(4-chloro-phenyl)-benzoimidazol-1-yl]-2-cyclohexyl-acetylamino}-benzoic acid,
(−)-3-chloro-4-{-2-[2-(4-chloro-phenyl)-benzoimidazol-1-yl]-2-cyclohexyl-acetylamino}-benzoic acid,
4-{2-[2-(4-chloro-phenyl)-5,6-difluoro-benzoimidazol-1-yl]-2-cyclohexyl-acetylamino}-3-methoxy-benzoic acid,
4-{2-[2-(4-chloro-phenyl)-5,6-difluoro-benzoimidazol-1-yl]-2-cyclohexyl-acetylamino}-3-trifluoromethyl-benzoic acid,
4-{2-cyclohexyl-2-[5,6-difluoro-2-(4-trifluoromethyl-phenyl)-benzoimidazol-1-yl]-acetylamino}-benzoic acid,
4-{2-cyclohexyl-2-[5-fluoro-2-(4-trifluoromethyl-phenyl)-benzoimidazol-1-yl]-acetylamino}-benzoic acid, 4-{2-[2-(4-chloro-phenyl)-5,6-difluoro-benzoimidazol-1-yl]-2-cyclohexyl-acetylamino}-3-trifluoromethoxy-benzoic acid,
4-{2-[2-(4-chloro-phenyl)-5-fluoro-benzoimidazol-1-yl]-2-cyclohexyl-acetylamino}-benzoic acid,
4-{2-[2-(4-chloro-phenyl)-5-fluoro-benzoimidazol-1-yl]-2-cyclohexyl-acetylamino}-3-fluoro-benzoic acid,
(4-{2-[2-(4-chloro-phenyl)-5,6-difluoro-benzoimidazol-1-yl]-2-cyclohexyl-acetylamino}-phenyl)-acetic acid,
2-(4-{2-[2-(4-chloro-phenyl)-5,6-difluoro-benzoimidazol-1-yl]-2-cyclohexyl-acetylamino}-3-fluoro-phenyl)-propionic acid,
2-(4-{2-[2-(4-chloro-phenyl)-5,6-difluoro-benzoimidazol-1-yl]-2-cyclohexyl-acetylamino}-3-fluoro-phenyl)-2-methyl-propionic acid,
3-(4-{2-[2-(4-chloro-phenyl)-5,6-difluoro-benzoimidazol-1-yl]-2-cyclohexyl-acetylamino}-phenyl)-propionic acid,
3-(4-{2-[2-(4-chloro-phenyl)-5,6-difluoro-benzoimidazol-1-yl]-2-cyclohexyl-acetylamino}-3-fluoro-phenyl)-propionic acid,
(−)-3-(4-{2-[2-(4-chloro-phenyl)-5,6-difluoro-benzoimidazol-1-yl]-2-cyclohexyl-acetylamino}-3-fluoro-phenyl)-propionic acid,
(+)-3-(4-{2-[2-(4-chloro-phenyl)-5,6-difluoro-benzoimidazol-1-yl]-2-cyclohexyl-acetylamino}-3-fluoro-phenyl)-propionic acid,
(4-{2-[2-(4-chloro-phenyl)-5,6-difluoro-benzoimidazol-1-yl]-2-cyclohexyl-acetylamino}-3-fluoro-phenoxy)-acetic acid,
2-(4-{2-[2-(4-chloro-phenyl)-5,6-difluoro-benzoimidazol-1-yl]-2-cyclohexyl-acetylamino}-3-fluoro-phenoxy)-propionic acid,
2-(4-{2-[2-(4-chloro-phenyl)-5,6-difluoro-benzoimidazol-1-yl]-2-cyclohexyl-acetylamino}-3-fluoro-phenoxy)-2-methyl-propionic acid,
(+)-2-(4-{-2-[2-(4-chloro-phenyl)-5,6-difluoro-benzoimidazol-1-yl]-2-cyclohexyl-acetylamino}-3-fluoro-phenoxy)-2-methyl-propionic acid,
(−)-2-(4-{-2-[2-(4-chloro-phenyl)-5,6-difluoro-benzoimidazol-1-yl]-2-cyclohexyl-acetylamino}-3-fluoro-phenoxy)-2-methyl-propionic acid,
1-(4-{2-[2-(4-chloro-phenyl)-5,6-difluoro-benzoimidazol-1-yl]-2-cyclohexyl-acetylamino}-3-fluoro-phenoxy)-cyclopropanecarboxylic acid,
(+)-1-(4-{-2-[2-(4-chloro-phenyl)-5,6-difluoro-benzoimidazol-1-yl]-2-cyclohexyl-acetylamino}-3-fluoro-phenoxy)-cyclopropanecarboxylic acid,
(−)-1-(4-{-2-[2-(4-chloro-phenyl)-5,6-difluoro-benzoimidazol-1-yl]-2-cyclohexyl-acetylamino}-3-fluoro-phenoxy)-cyclopropanecarboxylic acid,
2-[2-(4-chloro-phenyl)-5,6-difluoro-benzoimidazol-1-yl]-2-cyclohexyl-N-trans-(4-hydroxy-cyclohexyl)-acetamide,
(−)-2-[2-(4-chloro-phenyl)-5,6-difluoro-benzoimidazol-1-yl]-2-cyclohexyl-N-(4-hydroxy-cyclohexyl)-acetamide,
(+)-2-[2-(4-chloro-phenyl)-5,6-difluoro-benzoimidazol-1-yl]-2-cyclohexyl-N-(4-hydroxy-cyclohexyl)-acetamide,
6-{2-[2-(4-chloro-phenyl)-5,6-difluoro-benzoimidazol-1-yl]-2-cyclohexyl-acetylamino}-nicotinic acid, and pharmaceutically acceptable salts thereof.

Also preferred are the compounds of formula (I) selected from:
(+)-4-{2-[2-(4-Chloro-phenyl)-5,6-difluoro-benzoimidazol-1-yl]-2-cyclohexyl-acetylamino}-3-cyano-benzoic acid,
(−)-4-{2-[2-(4-Chloro-phenyl)-5,6-difluoro-benzoimidazol-1-yl]-2-cyclohexyl-acetylamino}-3-cyano-benzoic acid,
(+)-4-{2-[2-(4-Chloro-phenyl)-5,6-difluoro-benzoimidazol-1-yl]-2-cyclohexyl-acetylamino}-3-methoxy-benzoic acid,
(−)-4-{2-[2-(4-Chloro-phenyl)-5,6-difluoro-benzoimidazol-1-yl]-2-cyclohexyl-acetylamino}-3-methoxy-benzoic acid,
(+)-4-{2-[2-(4-Chloro-phenyl)-5,6-difluoro-benzoimidazol-1-yl]-2-cyclohexyl-acetylamino}-3-trifluoromethyl-benzoic acid,
(−)-4-{2-[2-(4-Chloro-phenyl)-5,6-difluoro-benzoimidazol-1-yl]-2-cyclohexyl-acetylamino}-3-trifluoromethyl-benzoic acid,
(+)-4-{2-[2-(4-Chloro-phenyl)-5,6-difluoro-benzoimidazol-1-yl]-2-cyclohexyl-acetylamino}-3-trifluoromethoxy-benzoic acid,
(−)-4-{2-[2-(4-Chloro-phenyl)-5,6-difluoro-benzoimidazol-1-yl]-2-cyclohexyl-acetylamino}-3-trifluoromethoxy-benzoic acid,
(−)-4-{2-[2-(4-Chloro-phenyl)-5-fluoro-benzoimidazol-1-yl]-2-cyclohexyl-acetylamino}-3-fluoro-benzoic acid,
(+)-4-{2-[2-(4-Chloro-phenyl)-5-fluoro-benzoimidazol-1-yl]-2-cyclohexyl-acetylamino}-3-fluoro-benzoic acid,
4-{2-[2-(4-Chloro-phenyl)-5,6-difluoro-benzoimidazol-1-yl]-2-cyclohexyl-acetylamino}-3-cyano-5-fluoro-benzoic acid,
(+)-4-{2-[2-(4-Chloro-phenyl)-5,6-difluoro-benzoimidazol-1-yl]-2-cyclohexyl-acetylamino}-3-cyano-5-fluoro-benzoic acid,
(−)-4-{2-[2-(4-Chloro-phenyl)-5,6-difluoro-benzoimidazol-1-yl]-2-cyclohexyl-acetylamino}-3-cyano-5-fluoro-benzoic acid,
1-(4-{2-[2-(4-Chloro-phenyl)-benzoimidazol-1-yl]-2-cyclohexyl-acetylamino}-3-fluoro-phenoxy)-cyclopropanecarboxylic acid,
(+)-1-(4-{2-[2-(4-Chloro-phenyl)-benzoimidazol-1-yl]-2-cyclohexyl-acetylamino}-3-fluoro-phenoxy)-cyclopropanecarboxylic acid,
(−)-1-(4-{2-[2-(4-Chloro-phenyl)-benzoimidazol-1-yl]-2-cyclohexyl-acetylamino}-3-fluoro-phenoxy)-cyclopropanecarboxylic acid,
4-{2-[2-(4-Chloro-phenyl)-benzoimidazol-1-yl]-2-cyclohexyl-acetylamino}-3-trifluoromethyl-benzoic acid,
(+)-4-{2-[2-(4-Chloro-phenyl)-benzoimidazol-1-yl]-2-cyclohexyl-acetylamino}-3-trifluoromethyl-benzoic acid,
(−)-4-{2-[2-(4-Chloro-phenyl)-benzoimidazol-1-yl]-2-cyclohexyl-acetylamino}-3-trifluoromethyl-benzoic acid,
4-{2-Cyclohexyl-2-[5,6-difluoro-2-(6-methoxy-pyridin-3-yl)-benzoimidazol-1-yl]-acetylamino}-cyclohexanecarboxylic acid,
(−)-4-{2-[2-(6-Chloro-pyridin-3-yl)-5,6-difluoro-benzoimidazol-1-yl]-2-cyclohexyl-acetylamino}-cyclohexanecarboxylic acid,
(4-{2-[2-(6-Chloro-2-methoxy-pyridin-3-yl)-5,6-difluoro-benzoimidazol-1-yl]-2-cyclohexyl-acetylamino}-cyclohexyl)-acetic acid,
4-{2-[2-(6-Chloro-2-methoxy-pyridin-3-yl)-5,6-difluoro-benzoimidazol-1-yl]-2-cyclohexyl-acetylamino}-cyclohexanecarboxylic acid,
4-{2-[2-(6-Chloro-2-methoxy-pyridin-3-yl)-5,6-difluoro-benzoimidazol-1-yl]-2-cyclohexyl-acetylamino}-benzoic acid,
(+)-4-{2-Cyclohexyl-2-[5,6-difluoro-2-(6-methoxy-pyridin-3-yl)-benzoimidazol-1-yl]-acetylamino}-cyclohexanecarboxylic acid,
(−)-4-{2-[2-(6-Chloro-2-methoxy-pyridin-3-yl)-5,6-difluoro-benzoimidazol-1-yl]-2-cyclohexyl-acetylamino}-cyclohexanecarboxylic acid,
(−)-(4-{2-[2-(6-Chloro-2-methoxy-pyridin-3-yl)-5,6-difluoro-benzoimidazol-1-yl]-2-cyclohexyl-acetylamino}-cyclohexyl)-acetic acid,
(+)-4-{(S)-2-[2-(6-Chloro-2-methoxy-pyridin-3-yl)-5,6-difluoro-benzoimidazol-1-yl]-2-cyclohexyl-acetylamino}-benzoic acid, 4-{2-Bicyclo[2.2.1]hept-7-yl-2-[2-(4-chloro-phenyl)-5,6-difluoro-benzoimidazol-1-yl]-acetylamino}-benzoic acid,
(4-{2-Cyclohexyl-2-[5,6-difluoro-2-(2-methoxy-pyridin-3-yl)-benzoimidazol-1-yl]-acetylamino}-cyclohexyl)-acetic acid,
4-[2-Cyclohexyl-2-(5,6-difluoro-2-p-tolyl-benzoimidazol-1-yl)-acetylamino]-benzoic acid
4-[2-Cyclohexyl-2-(5,6-difluoro-2-p-tolyl-benzoimidazol-1-yl)-acetylamino]-cyclohexanecarboxylic acid,
(−)-4-[2-Cyclohexyl-2-(5,6-difluoro-2-p-tolyl-benzoimidazol-1-yl)-acetylamino]-benzoic acid,
(+)-[2-Cyclohexyl-2-(5,6-difluoro-2-p-tolyl-benzoimidazol-1-yl)-acetylamino]-cyclohexanecarboxylic acid,
4-{2-Bicyclo[2.2.1]hept-7-yl-2-[2-(4-chloro-phenyl)-5,6-difluoro-benzoimidazol-1-yl]-acetylamino}-cyclohexanecarboxylic acid,
4-{2-Cyclohexyl-2-[5,6-difluoro-2-(4-methoxy-phenyl)-benzoimidazol-1-yl]-acetylamino}-benzoic acid,
(−)-4-{2-Bicyclo[2.2.1]hept-7-yl-2-[2-(4-chloro-phenyl)-5,6-difluoro-benzoimidazol-1-yl]-acetylamino}-cyclohexanecarboxylic acid,
4-{2-Cyclohexyl-2-[5,6-difluoro-2-(4-methoxy-phenyl)-benzoimidazol-1-yl]-acetylamino}-cyclohexanecarboxylic acid,
(−)-4-{2-Cyclohexyl-2-[5,6-difluoro-2-(4-methoxy-phenyl)-benzoimidazol-1-yl]-acetylamino}-benzoic acid,
(4-{2-Bicyclo[2.2.1]hept-7-yl-2-[2-(4-chloro-phenyl)-5,6-difluoro-benzoimidazol-1-yl]-acetylamino}-cyclohexyl)-acetic acid,
(−)-4-{2-Bicyclo[2.2.1]hept-7-yl-2-[2-(4-chloro-phenyl)-5,6-difluoro-benzoimidazol-1-yl]-acetylamino}-benzoic acid,
(−)-(4-{2-Bicyclo[2.2.1]hept-7-yl-2-[2-(4-chloro-phenyl)-5,6-difluoro-benzoimidazol-1-yl]-acetylamino}-cyclohexyl)-acetic acid,
2-[2-(4-Chloro-phenyl)-5,6-difluoro-benzoimidazol-1-yl]-2-cyclohexyl-N-[4-(1H-tetrazol-5-yl)-phenyl]-acetamide,
2-[2-(4-Chloro-phenyl)-5,6-difluoro-benzoimidazol-1-yl]-N-[2-chloro-4-(1H-tetrazol-5-yl)-phenyl]-2-cyclohexyl-acetamide,
2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide,
(+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide,
(+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide,
2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide,
(+)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide,
(−)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide,
2-[2-(4-Chloro-phenyl)-benzoimidazol-1-yl]-2-cyclohexyl-N-[4-(1H-tetrazol-5-yl)-2-trifluoromethyl-phenyl]-acetamide,
(+)-2-[2-(4-Chloro-phenyl)-benzoimidazol-1-yl]-2-cyclohexyl-N-[4-(1H-tetrazol-5-yl)-2-trifluoromethyl-phenyl]-acetamide,
(−)-2-[2-(4-Chloro-phenyl)-benzoimidazol-1-yl]-2-cyclohexyl-N-[4-(1H-tetrazol-5-yl)-2-trifluoromethyl-phenyl]-acetamide,
2-Cyclohexyl-2-[2-(2,6-dimethoxy-pyridin-3-yl)-5,6-difluoro-benzoimidazol-1-yl]-N-[2-fluoro-4-(1H-tetrazol-5-yl)-phenyl]-acetamide,
2-Cyclohexyl-2-[2-(2,6-dimethoxy-pyridin-3-yl)-5,6-difluoro-benzoimidazol-1-yl]-N-[4-(1H-tetrazol-5-yl)-2-trifluoromethyl-phenyl]-acetamide, and pharmaceutically acceptable salts thereof.

Particularly preferred compounds of formula (I) are those selected from the group consisting of
2-cyclohexyl-2-[2-(2,6-dimethoxy-pyridin-3-yl)-5,6-difluoro-benzoimidazol-1-yl]-N-(4-hydroxy-cyclohexyl)-acetamide,
(+)-2-cyclohexyl-2-[2-(2,6-dimethoxy-pyridin-3-yl)-5,6-difluoro-benzoimidazol-1-yl]-N-(trans-4-hydroxy-cyclohexyl)-acetamide,
(−)-2-[2-(4-chloro-phenyl)-5,6-difluoro-benzoimidazol-1-yl]-2-cyclohexyl-N-(4-hydroxy-cyclohexyl)-acetamide, and pharmaceutically acceptable salts thereof.

Other especially preferred compounds of formula (I) are those selected from the group consisting of
4-{2-[2-(4-chloro-phenyl)-5,6-difluoro-benzoimidazol-1-yl]-2-cyclohexyl-acetylamino}-benzoic acid,
(−)-4-{2-[2-(4-chloro-phenyl)-5,6-difluoro-benzoimidazol-1-yl]-2-cyclohexyl-acetylamino}-benzoic acid,
4-{2-[2-(4-chloro-phenyl)-5,6-difluoro-benzoimidazol-1-yl]-2-cyclohexyl-acetylamino}-3-fluoro-benzoic acid,
(−)-4-{2-[2-(4-chloro-phenyl)-5,6-difluoro-benzoimidazol-1-yl]-2-cyclohexyl-acetylamino}-3-fluoro-benzoic acid, and pharmaceutically acceptable salts thereof.

Other particularly preferred compounds of formula (I) are those selected from the group consisting of
2-(4-{2-[2-(4-chloro-phenyl)-5,6-difluoro-benzoimidazol-1-yl]-2-cyclohexyl-acetylamino}-3-fluoro-phenoxy)-2-methyl-propionic acid,
(−)-2-(4-{-2-[2-(4-chloro-phenyl)-5,6-difluoro-benzoimidazol-1-yl]-2-cyclohexyl-acetylamino}-3-fluoro-phenoxy)-2-methyl-propionic acid,
1-(4-{2-[2-(4-chloro-phenyl)-5,6-difluoro-benzoimidazol-1-yl]-2-cyclohexyl-acetylamino}-3-fluoro-phenoxy)-cyclopropanecarboxylic acid,
(−)-1-(4-{-2-[2-(4-chloro-phenyl)-5,6-difluoro-benzoimidazol-1-yl]-2-cyclohexyl-acetylamino}-3-fluoro-phenoxy)-cyclopropanecarboxylic acid, and pharmaceutically acceptable salts thereof.

Other particularly preferred compounds of formula (I) are those selected from the group consisting of
(−)4-{2-[2-(4-Chloro-phenyl)-5,6-difluoro-benzoimidazol-1-yl]-2-cyclohexyl-acetylamino}-3-cyano-benzoic acid,
(−)-4-{2-[2-(4-Chloro-phenyl)-5,6-difluoro-benzoimidazol-1-yl]-2-cyclohexyl-acetylamino}-3-trifluoromethyl-benzoic acid,
(−)-4-{2-[2-(4-Chloro-phenyl)-5,6-difluoro-benzoimidazol-1-yl]-2-cyclohexyl-acetylamino}-3-cyano-5-fluoro-benzoic acid,
(−)-4-{2-[2-(4-Chloro-phenyl)-benzoimidazol-1-yl]-2-cyclohexyl-acetylamino}-3-trifluoromethyl-benzoic acid, and pharmaceutically acceptable salts thereof.

Other particularly preferred compounds of formula (I) are those selected from the group consisting of
(+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide,
(−)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide,
(−)-2-[2-(4-Chloro-phenyl)-benzoimidazol-1-yl]-2-cyclohexyl-N-[4-(1H-tetrazol-5-yl)-2-trifluoromethyl-phenyl]-acetamide, and pharmaceutically acceptable salts thereof.

It will be appreciated that the compounds of general formula (I) in this invention may be derivatised at functional groups to provide derivatives which are capable of conversion back to the parent compound in vivo.

The invention also relates to a process for the preparation of compounds of formula (I) as defined above, which process comprises cyclisation of a compound of formula (II)

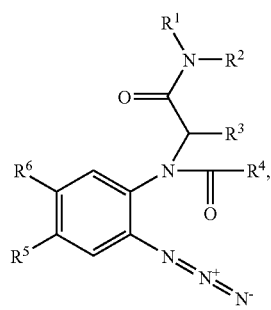

wherein $R^1$, $R^2$, $R^3$, $R^4$, $R^5$ and $R^6$ are as defined above.

The cyclisation of a compound of formula (II) can be performed under reaction conditions well known to the person skilled in the art. Such cyclisations can conveniently be carried e.g. in a suitable solvent such as e.g. dichloromethane at a suitable temperature in the presence of a suitable reagent such as free $PPh_3$ or resin bound $PPh_3$.

The invention further relates to an alternative process for the preparation of compounds of formula (I) as defined above, which process comprises amide coupling of an acid of formula (III)

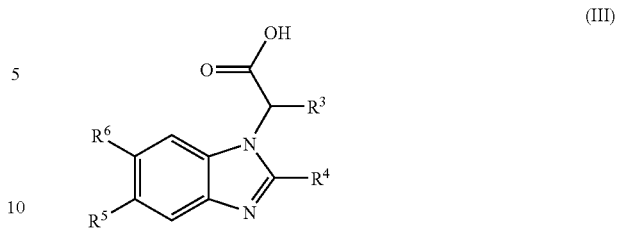

wherein $R^3$, $R^4$, $R^5$ and $R^6$ are as defined above, with an amine of formula (IV)

$$R^1\text{—}NH_2 \qquad (IV)$$

wherein $R^1$ is as defined above.

The amid coupling of a compound of formula (III) can be performed under reaction conditions well known to the person skilled in the art. Such coupling can conveniently be carried e.g. in a suitable solvent such as N,N-dimethylformamide (DMF) or dioxane at a suitable temperature in the presence of a suitable coupling reagent such as N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT) or O-benzotriazol-1-yl-N,N,N',N'-tetramethyluronium tetrafluoroborate (TBTU).

The present invention also relates to compounds of formula (I) as defined above, when prepared by a process as described above.

The compounds of formula (I) can be prepared by methods known in the art or as described below. Unless otherwise indicated, the substituents $R^1$ to $R^8$ are as described above. Compounds of formula (I) according to the present invention can be prepared e.g. by the methods and procedures given below. A typical procedure for the preparation of compounds of formula (I) is illustrated in scheme 1 below.

Scheme 1

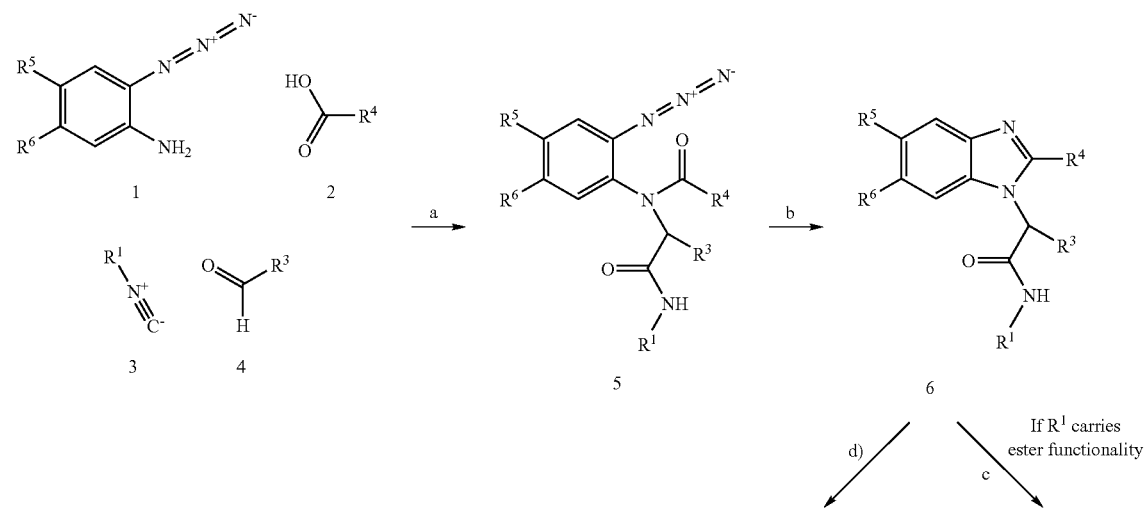

-continued

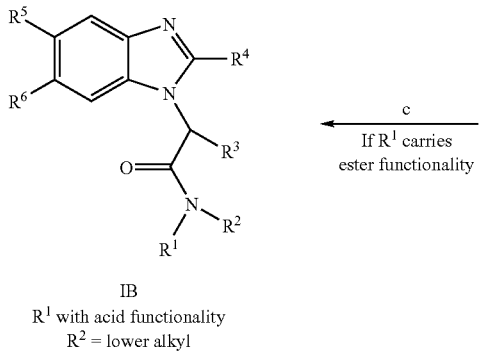

IB
R¹ with acid functionality
R² = lower alkyl

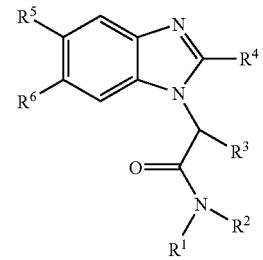

7
R² = lower alkyl

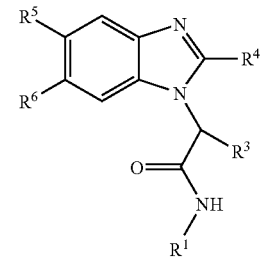

IA
R¹ with acid functionality

In a suitable organic solvent such as e.g. MeOH a 2-azidoarylamine 1, a carboxylic acid 2, an isonitrile 3 and an aldehyde 4 are condensed to 5 in a so called Ugi-type reaction (step a, typical procedures may be found, e.g. in "The Peptides" by Gross & Meienhofer vol. 2, Academic Press, N.Y., 1980, pp 365-381). In a subsequent intramolecular Staudinger-type reaction with a suitable reagent such as, e.g. PPh₃, the azido bisamide 5 is converted to the benzimidazole 6. In those cases where the substituent R¹ carries an ester functionality the ester functionality can be cleaved under basic (e.g. methyl or ethyl esters with lithium hydroxide in polar solvents such as, e.g. methanol, water or THF or mixtures of said solvents) or under acidic conditions (e.g. tert-butyl ester using concentrated hydrochloric acid in THF or formic acid in methanol) to furnish final compounds IA (step c). Optionally the benzimidazole 6 can be N-alkylated by deprotonation with a strong base (e.g. NaH or LiHMDA) and subsequent treatment with an alkylating agent R²—X with X being a typical leaving group such as e.g. Cl, Br, I, SO₂alkyl, SO₂fluoroalkyl, SO₂aryl (step d). In the resulting compounds 7, like for derivatives 6, the ester group can be cleaved as described under step c. Many of the building blocks 2-4, particularly the carboxylic acid 2, are commercially available. If not, they may be prepared from commercially available starting materials using procedures described in literature and typically known to those skilled in the art. The isonitrile 3 can e.g. be obtained by dehydration of the corresponding formamide R¹—N—CHO with a suitable reagent such as e.g. phosgene, POCl₃ or Me₂N=CH⁺ClCl⁻. Aldehyde 4 can e.g. be prepared from the corresponding alcohol by oxidation with a suitable oxidant such as e.g. tetrapropylammonium perruthenate(VII). The 2-azidoarylamine 1 is usually prepared in three steps from the corresponding 2-aminoarylcarboxylic acid, which is converted into a 2-azidoarylcarboxylic acid by diazotation with NaNO₂ in a suitable solvent (e.g. methanol) and subsequent treatment with a suitable azide salt such as NaN₃. The resulting 2-azidoarylcarboxylic acid is then converted into 1 via Curtius rearrangement of the 2-azidoarylcarboxylic azide obtained from the 2-azidoarylcarboxylic acid by its activation of with a suitable reagent (e.g. chloroethylformiate in the presence of a base such as triethylamine) and subsequent treatment with a suitable source of azide anions (e.g. sodium azide). The 2-azidoaryl amine 1 can alternatively be prepared via the 2-azidoarylcarboxamide obtained by activation of the 2-azidoarylcarboxylic acid with a suitable reagent (e.g. chloroethylformiate in the presence of a base such as triethylamine) and subsequent treatment with ammonia. This amide is converted into 1 in a so called Hofmann-rearrangement by treatment with a suitable reagent such as NaOBr.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds (1), (2), (3) or (4) contain stereogenic centers, compounds (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

An alternative approach to the preparation of compounds of formula I is illustrated in the scheme below.

Scheme 2

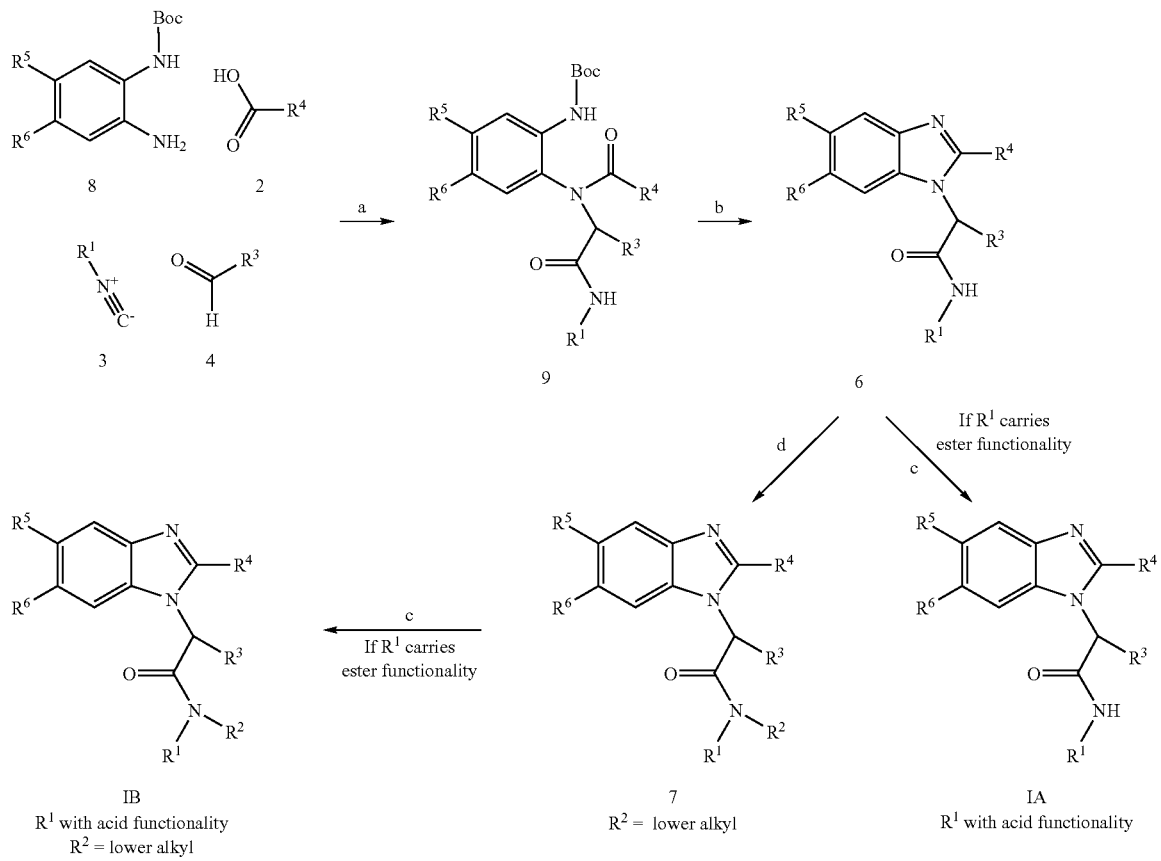

Compounds of the general formula I can also be prepared as described in scheme 2. In this approach a mono boc-protected ortho arylene diamine 8, a carboxylic acid 2, an isonitrile 3, and an aldehyde 4 are condensed in an organic solvent such as e.g. methanol in the presence of an acid (such as e.g. HCl) to the bis amide 9 again in an Ugi-type condensation (step a). Bisamide 9 is deprotected with TFA and cyclised to the desired benzimidazole 6 (step b). In case where intermediate 9 carries an ester functionality this can be cleaved as described under scheme 1 to give compounds of the formula IA. Optionally, intermediate 9 can be N-alkylated as described before (step c) to give intermediates 7 which in turn can be converted into compounds of formula IB using the conditions described under scheme 1. Typical procedures applicable to this approach were described e.g. by Tempest et al. in Tet. Lett. 2001, 42, 4959-4962 and 4963-4968, or by Zhang et al. in Tet. Lett. 2004, 45, 6757-6760. Mono boc-protected ortho arylene diamines 1 are commercially available or may be prepared from the corresponding unprotected diamine by treatment with di-tert-butyl dicarbonate in an organic solvent such as e.g. THF in the presence of a base such as e.g. diisopropylethylamine.

If desired or required functional groups present in I (such as —$CO_2$alkyl, amino groups, cyano groups and others) may be derivatized to other functional groups using typical standard procedures known to those skilled in the art (e.g. reduction of —$CO_2$alkyl to —$CH_2OH$ with $LiAlH_4$, hydrolysis of —$CO_2$alkyl to $CO_2H$ and subsequent optional conversion to an amide, acylation of amino groups).

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (2), (3), (4), (6), (7) or (9) contain stereogenic centers, compounds (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

$R^1$ as present in (I) after steps a and b or steps a, b and c in above shown schemes may be transformed into or replaced by other $R^1$ using one or a sequence of reaction steps. Two possible examples are given below:

a) $R^1$=$CH_2Ph$ may for instance be removed using debenzylation conditions (e.g. hydrogenolysis in a solvent such as methanol in presence of a catalyst such as Pd(0) on charcoal powder) and a new $R^1$ can be introduced e.g. by deprotonation of the resulting $CONHR^2$ with a strong base (e.g. LiHMDA) and treatment with an alkylating agent $R^1$—X (X being a typical leaving group such as e.g. Cl, Br, I, $SO_2$alkyl, $SO_2$fluoroalkyl, $SO_2$aryl, and $R^1$ being $C_{1-10}$-alkyl, lower-alkoxy-lower-alkyl, lower-alkoxy-carbonyl-lower-alkyl, cycloalkyl, cycloalkyl-lower-alkyl, aryl-lower-alkyl, di-aryl-lower-alkyl, heteroaryl-lower-alkyl or heterocyclyl-lower-alkyl) or alternatively by a Pd(II)-promoted coupling with $R^1$—X ($R^1$ being aryl or heteroaryl and X being Cl, Br, I or $OSO_2CF_3$)

b) Amidolysis of the —$CR^3CONR^1R^2$-moiety of (I) to —$CR^3COOH$ may be carried out using suitable conditions such as heating in isopropanol in presence of NaOH or LiOH. A new amide bond can then be formed using an amine $HNR^1R^2$ and a typical peptide coupling reagent such as e.g. EDCI, DCC or TPTU.

Functional groups present in (I) or any intermediates which are not stable or are reactive under the reaction conditions of one or more of the reaction steps, can be protected with appropriate protecting groups (as described e.g. in "Protective Groups in Organic Chemistry" by T. W. Greene and P. G. M. Wutts, $2^{nd}$ Ed., 1991, Wiley N.Y.) before the critical step applying methods well known in the art. Such protecting groups can be removed at a later stage of the synthesis using standard methods described in the literature.

An alternative method for the amidolysis of Ugi reaction products is the treatment of benzimidazoles such as 10 with sodium nitrite in a mixture of acetic acid and acetic acid anhydride to give an intermediate diazotation reaction product which after rearrangement can be cleaved upon reaction with a mixture of alkaline hydroxides (e.g., LiOH, NaOH, KOH) and hydrogen peroxide to the corresponding free carboxylic acids 11 (Scheme 3, step a; see: E. H. White *J. Am. Chem. Soc.* 1955, 77, 6011-6014, D. A: Evans, P. H. Carter, C. J. Dinsmore, J. C. Barrow, J. L. Katz, D. W. Kung *Tetrahedron Lett.* 1997, 38, 4535-4538). The amide cleavage reaction is broad with respect to the nature of the amide that can be employed and is by no means limited to benzylamides only. The application of chiral acids in the Ugi reaction step leads to the formation of diastereoisomers, which might be separable by standard chromatography on normal silicia either on the step of the amide 10 or the free acid 11. Alternatively, chiral acids 11 can be resolved by standard methods known to the person skilled in the art such as crystallization with chiral amines or by chiral chromatography.

Another approach to the preparation of compounds of formula I is illustrated in scheme 4 below.

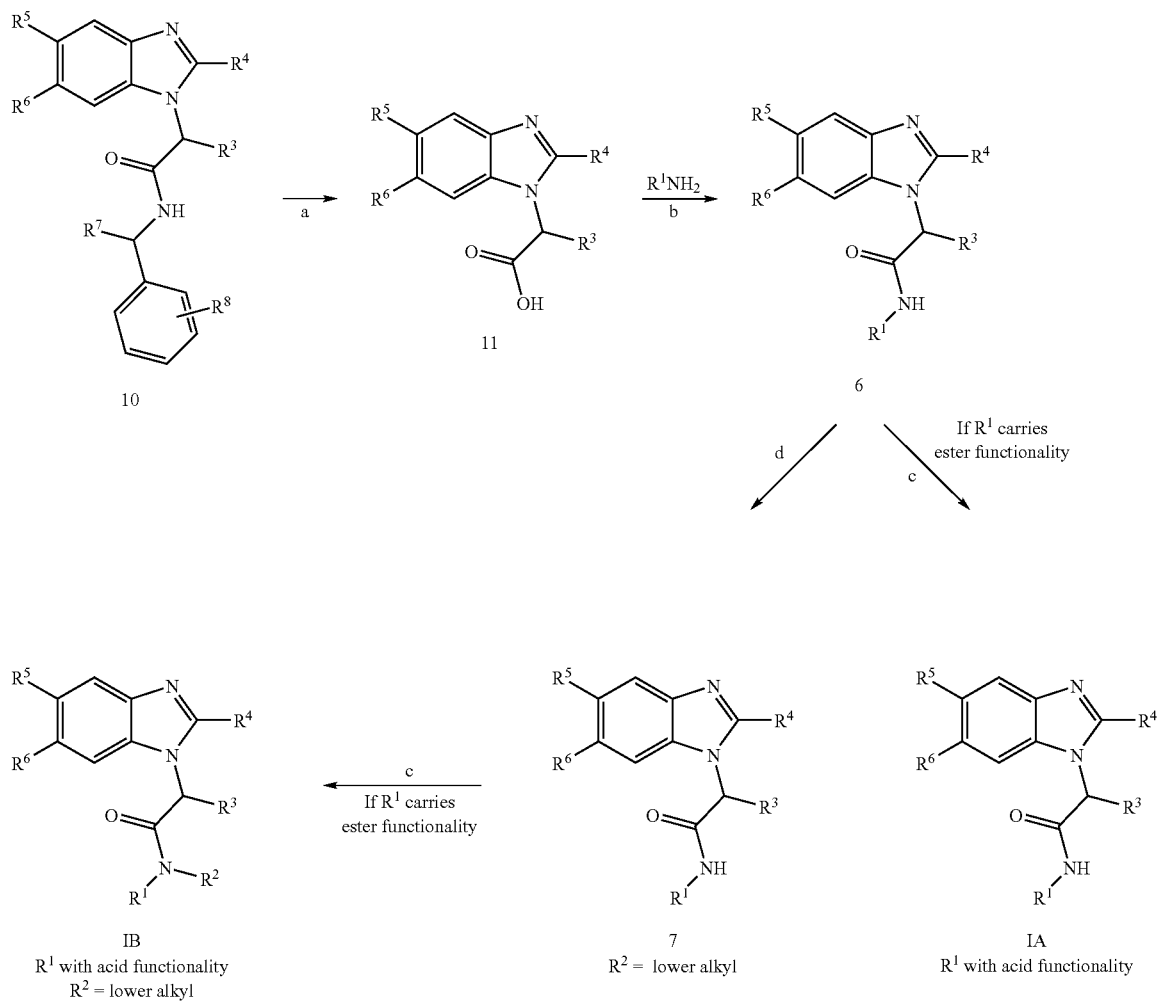

Scheme 3

Scheme 4

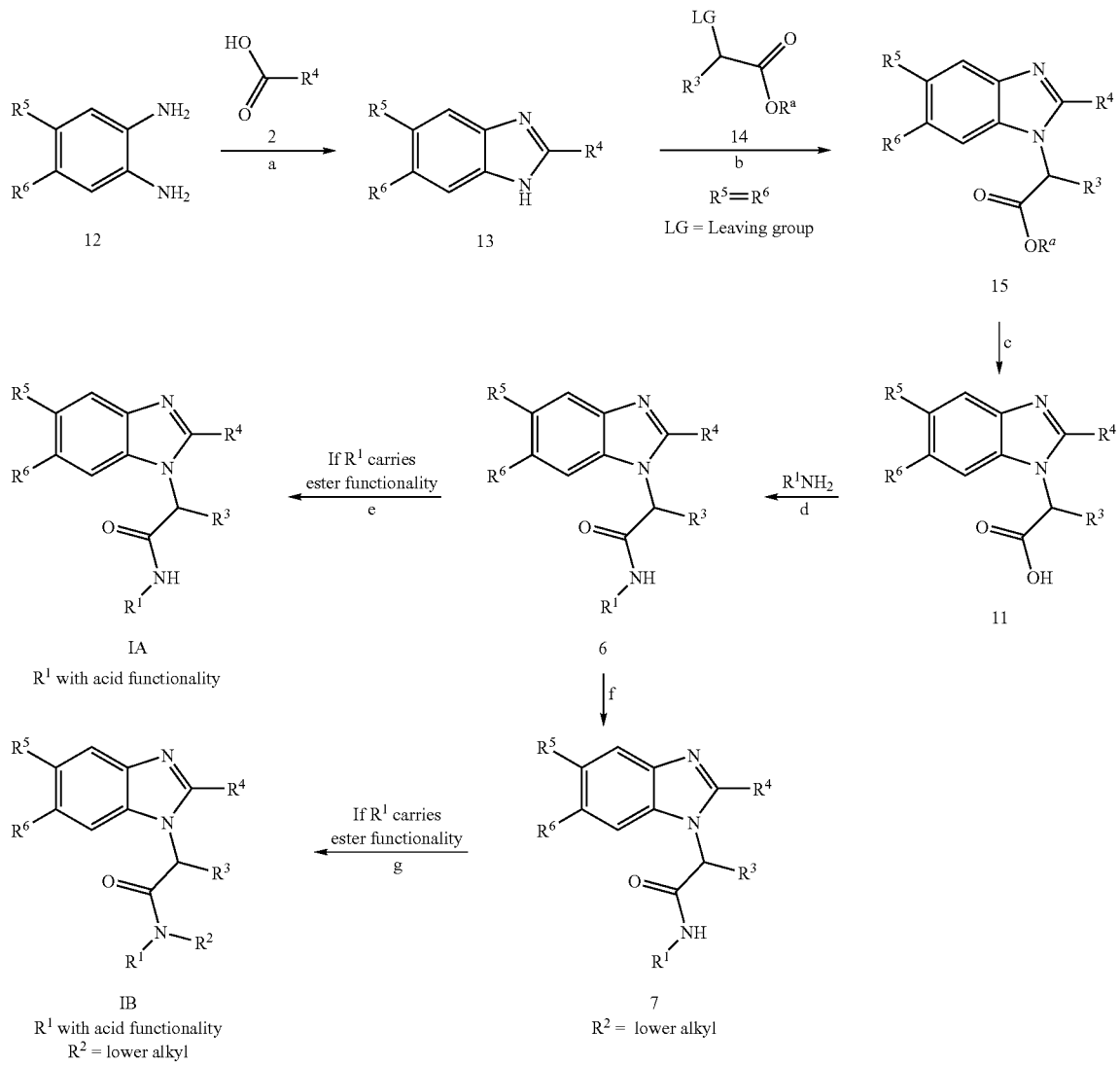

Compounds of the general formula IA and IB can also be prepared according to scheme 4. Benzimidazoles of the general structure 13 (either commercially available or accessible via, e.g. reaction of an appropriately substituted phenylene diamine 12 with an aryl-carboxylic acid 2, step a) can be alkylated with, e.g. a 2-bromo (or other leaving group such as, e.g. $OSO_2$alkyl, $OSO_2$fluoroalkyl, $OSO_2$aryl)-alkylacetic acid ester 14 in an appropriate solvent such as, e.g. N,N'-dimethylformamide and a suitable base such as, e.g. cesium carbonate to give intermediates 12 ($R^9$ signifies an alkyl group such as e.g. methyl, ethyl or tert-butyl). Cleavage of the ester functionality using the same condition as described under scheme 1 yields acid intermediates 15. Amide coupling of intermediates 11 with optionally substituted Cycloalkyl/Aryl amines (either commercially available or accessible by methods described in references or by methods known in the art) gives compounds 6 (step d). Amide couplings of this type are widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. N,N-dimethylformamide (DMF) or dioxane, optionally in the presence of a base (e.g. triethylamine, diisopropylethylamine or 4-(dimethylamino)pyridine). Alternatively, intermediates 6 can be obtained by converting intermediates 11 into their acid chlorides by treatment with, e.g. thionyl chloride, optionally in a solvent such as, e.g. dichloromethane and reaction of the acid chloride with optionally substituted Cycloalkyl/Aryl amines in an appropriate solvent such as, e.g. dichloromethane and a base such as, e.g. triethylamine, pyridine diisopropylethylamine or 4-(dimethylamino)pyridine. Conversion of intermediates 6 into compounds of the general formula IA and IB can be accomplished as described in the preceding schemes.

It is known to those skilled in the art that tetrazoles can be synthesized by a variety of standard procedures. For example, organic nitrites can be reacted with sodium azide and ammonium chloride or trialkyl- or tetraalkyl-ammonium chloride in an appropriate solvent such as, e.g. DMF, DMSO, N-methylpyrrolidine or toluene to furnish the tetrazoles. Alternatively, organic azides such as organo-tin, -silicon, -boron and -aluminium azides such as, e.g. trialkyltin- or trimethylsilylazides in an appropriate solvent such as, e.g. toluene, can be reacted with nitrites to form tetrazoles. For some of these reactions elevated temperatures such as, e.g. the boiling temperature of the solvent may be required. Another method for the preparation of tetrazoles include the reaction of an alkyl- or arylnitrile with sodium azide in the presence of a Lewis acid such as, e.g. boron trifluoride or zinc bromide in solvents like dichloromethane, N,N-dimethylformamide or water at temperatures between 0° C. and the boiling point of the solvent.

A process for preparing tetrazoles includes the reaction of a nitrile group-carrying derivative of formula 6 and 7 (prepared as described in schemes 1 to 4) with sodium azide and a trialkylammonium salt such as, e.g. triethylammonium hydrochloride in a suitable solvent such as, e.g. xylene at elevated temperatures, preferably at the boiling point of the solvent.

If compounds of formula 6 or 7 contain stereogenic centers, compounds (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent. The tetrazole forming step can be done on chiral or achiral benzimidazoles of type 6 or 7.

Functional groups present in (I) or any intermediates which are not stable or are reactive under the tetrazole forming reaction conditions, can be protected with appropriate protecting groups (as described e.g. in "Protective Groups in Organic Chemistry" by T. W. Greene and P. G. M. Wutts, 2$^{nd}$ Ed., 1991, Wiley N.Y.) before the critical step, applying methods well known in the art. Such protecting groups can be removed at a later stage of the synthesis using standard methods described in the literature.

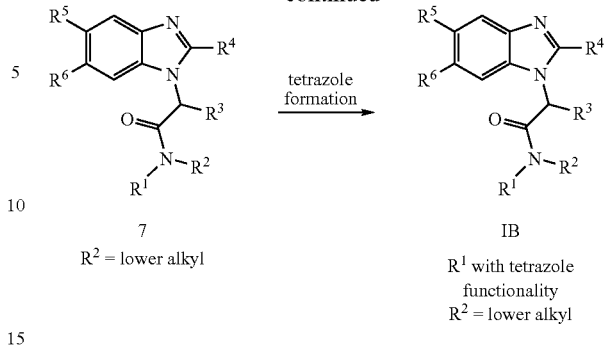

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate FXR. They can therefore be used in the treatment or prophylaxis of diseases and conditions which are modulated by FXR agonists. "Diseases (and conditions) which are modulated by FXR agonists" include increased lipid and cholesterol levels, particularly high LDL-cholesterol, high triglycerides, low HDL-cholesterol, dyslipidemia, atherosclerotic disease, diabetes, particularly non-insulin dependent diabetes mellitus, metabolic syndrome, cholesterol gallstone disease, cholestasis/fibrosis of the liver, diseases of cholesterol absorption, cancer, particularly gastrointestinal cancer, osteoporosis, peripheral occlusive disease, ischemic stroke, Parkinson's disease and Alzheimer's disease. Preferred diseases (and conditions) which are modulated by FXR agonists are prevention or treatment of high LDL cholesterol levels, high triglycerides, dyslipidemia, cholesterol gallstone disease, cancer, non-insulin dependent diabetes mellitus and metabolic syndrome. Particularly preferred diseases which are modulated by FXR agonists are high LDL cholesterol, high triglyceride levels and dyslipidemia.

The invention therefore also relates to pharmaceutical compositions comprising a compound as defined above, in a therapeutically effective amount, and a pharmaceutically acceptable carrier and/or adjuvant.

The invention likewise embraces compounds as described above for use as therapeutically active substances, especially as therapeutically active substances for the treatment or prophylaxis of diseases which are modulated by FXR agonists, particularly as therapeutically active substances for the treatment or prophylaxis of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and/or Alzheimer's disease.

In another preferred embodiment, the invention relates to a method for the therapeutic or prophylactic treatment of diseases which are modulated by FXR agonists, particularly for the therapeutic or prophylactic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and Alzheimer's disease which method comprises administering a compound as defined above to a human being or animal.

The invention also embraces the use of compounds as defined above for the therapeutic or prophylactic treatment of diseases which are modulated by FXR agonists, particularly for the therapeutic or prophylactic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and Alzheimer's disease.

The invention also relates to the use of compounds as described above for the preparation of medicaments for the therapeutic or prophylactic treatment of diseases which are modulated by FXR agonists, particularly for the therapeutic or prophylactic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and Alzheimer's disease. Such medicaments comprise a compound as described above.

The following tests were carried out in order to determine the activity of the compounds of formula (I). Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21 (pLysS) cells by standard methods (Current Protocols in Molecular Biology, Wiley Press, ed. Ausubel et al).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$. For each reaction well in a 96-well plate, 40 nM of GST-FXR LBD fusion protein was bound to 10 μg glutathione yttrium silicate SPA beads (PharmaciaAmersham) in a final volume of 50 μl by shaking. A radioligand (eg. 40 nM) of 2,N-dicyclohexyl-2-[2-(2,4 dimethoxy-phenyl)-benzoimidazol-1-yl]-acetamide) was added, and the reaction incubated at RT for 30 minutes in the presence of test compounds followed by scintillation proximity counting. All binding assays were performed in 96-well plates and the amount of bound ligand was measured on a Packard TopCount using OptiPlates (Packard). Dose response curves were performed within a range of concentration from $6 \times 10^{-9}$ M to $2.5 \times 10^{-5}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plates at a density of $10^5$ cells/well and then transfected with the pFA-FXR-LBD or expression plasmid plus a reporter plasmid. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays ($EC_{50}$ or $IC_{50}$), preferably in the range of 0.5 nM to 10 μM, more preferably 0.5 nM to 100 nM.

For example, the following compounds showed the following $IC_{50}$ values in the binding assay described above:

| Example | IC50 μm |
|---------|---------|
| 1 | 15.99 |
| 2 | 0.33 |
| 3 | 1.27 |
| 4 | 2.72 |
| 5 | n.a |
| 6 | n.a |
| 7 | n.a |
| 8 | 0.02 |
| 9 | 0.01 |
| 10 | 0.31 |
| 11 | n.a |
| 12 | 0.28 |
| 13 | 0.06 |
| 14 | 0.54 |
| 15 | 0.05 |
| 16 | 0.61 |
| 17 | 0.21 |
| 18 | 0.09 |
| 19 | 0.31 |
| 20 | 4.04 |
| 21 | 0.01 |
| 22 | 0.31 |
| 23 | 1.34 |
| 24 | 0.05 |
| 25 | 0.13 |
| 26 | 1.71 |
| 27 | 0.02 |
| 28 | 0.05 |
| 29 | 0.49 |
| 30 | 0.01 |
| 31 | 0.04 |
| 32 | 0.54 |
| 33 | 0.04 |
| 34 | 0.003 |
| 35 | 0.60 |

-continued

| Example | IC50 μm |
|---|---|
| 36 | 0.007 |
| 37 | 0.05 |
| 38 | 0.04 |
| 39 | n.a |
| 40 | n.a |
| 41 | 0.59 |
| 42 | 0.01 |
| 43 | 0.28 |
| 44 | 0.21 |
| 45 | 0.05 |
| 46 | 0.21 |
| 47 | 0.04 |
| 48 | 1.35 |
| 49 | 0.17 |
| 50 | 0.80 |
| 51 | 0.060 |
| 52 | 0.003 |
| 53 | 0.01 |
| 54 | 0.39 |
| 55 | 0.06 |
| 56 | 0.01 |
| 57 | 0.006 |
| 58 | 0.13 |
| 59 | 0.002 |
| 60 | 0.002 |
| 61 | 2.08 |
| 62 | 0.001 |
| 63 | 0.20 |
| 64 | 17.10 |
| 65 | 0.04 |
| 66 | 0.2 |
| 67 | 0.74 |
| 68 | 0.12 |
| 69 | 1.03 |
| 70 | 0.74 |
| 71 | 0.75 |
| 72 | 0.01 |
| 73 | 0.25 |
| 74 | 0.03 |
| 75 | 0.30 |
| 76 | 0.04 |
| 77 | 0.00 |
| 78 | 1.80 |
| 79 | 0.01 |
| 80 | 0.06 |
| 81 | 8.60 |
| 82 | 0.43 |
| 83 | 0.01 |
| 84 | 2.00 |
| 85 | 0.01 |
| 86 | 1.4 |
| 87 | 1.7 |
| 88 | 1.6 |
| 89 | 1.2 |
| 90 | 0.5 |
| 91 | 4.2 |
| 92 | 0.3 |
| 93 | 0.4 |
| 94 | 1.3 |
| 95 | 0.5 |
| 96 | 3.3 |
| 97 | 3.6 |
| 98 | 3.3 |
| 99 | 0.5 |
| 100 | 3.2 |
| 101 | 0.8 |
| 102 | 2.8 |
| 103 | 0.2 |
| 104 | 0.8 |
| 105 | 0.4 |
| 106 | 0.3 |
| 107 | 0.3 |
| 108 | 0.04 |
| 109 | 0.015 |
| 110 | 0.006 |
| 111 | 0.001 |
| 112 | 0.078 |

-continued

| Example | IC50 μm |
|---|---|
| 113 | 0.008 |
| 114 | 0.004 |
| 115 | 0.355 |
| 116 | 0.022 |
| 117 | 0.013 |
| 118 | 0.350 |
| 119 | 0.001 |
| 120 | n.a. |
| 121 | n.a. |

The compounds of formula (I) and their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following examples serve to illustrate the present invention in more detail. They are, however, not intended to limit its scope in any manner.

EXAMPLES

Abbreviations

DCM=dichloromethane, DIPEA=N,N'-diisopropylethylamine, DMF=dimethylformamide, HATU=2-(7-Aza-1H-benzotriazole-1-yl)-1,1,3,3-tetramethyluronium hexafluorophosphate, HCl=hydrogen chloride, HPLC=high pressure liquid chromatography, LiOH=lithium hydroxide, MPLC=medium pressure liquid chromatography, $NaHCO_3$=sodium hydrogen carbonate, rt=room temperature, $SiO_2$=silica gel.

General Remarks

Reactions were carried out under nitrogen or argon atmosphere, when appropriate.

Example 1

3-Chloro-4-{2-[2-(6-chloro-pyridin-3-yl)-5,6-difluoro-benzoimidazol-1-yl]-2-cyclohexyl-acetylamino}-benzoic acid The title compound was prepared by heating [2-(6-chloro-pyridin-3-yl)-5,6-difluoro-benzoimidazol-1-yl]-cyclohexylacetic acid (200 mg, 0.46 mmol) in 5 ml thionylchloride to 80° C. for 4 h. The solvent was evaporated and the residue taken up in dichloromethane. 4-Amino-3-chloro-benzoic acid methyl ester (85 mg, 0.46 mmol) were added and the reaction mixture stirred at rt overnight. The crude product was worked up by addition of a solution of 1 M $NaHCO_3$ and extraction of the aqueous layer with dichloromethane. Organic layers were combined, dried over $MgSO_4$ and evaporated to dryness. The residue was taken up in methanol (3 ml) and 1N NaOH (1 ml) added. The mixture was stirred at rt overnight, the solvent evaporated and the product isolated via preparative HPLC. MS ($ES^+$): 560 (M+H).

Intermediates a) [2-(6-Chloro-pyridin-3-yl)-5,6-difluoro-benzoimidazol-1-yl]-cyclohexyl-acetic acid To a solution of (2-amino-4,5-difluoro-phenyl)-carbamic acid tert-butyl ester (1.0 g, 4.1 mmol) in methanol (15 mL) were added cyclohexanecarbaldehyde (0.82 mL, 6.14 mmol, 1.5 equiv.), 6-chloro-nicotinic acid (0.665 g, 4.1 mmol, 1.0 equiv.) and isocyanomethyl-benzene (0.48 mL, 10.24 mmol, 1.0 equiv.) and stirred at rt for 16 h. A solution of 4 M HCl in dioxane (10 mL) was added and the reaction mixture stirred at rt for 3 h. The solution was concentrated by evaporation under reduced pressure, the pH adjusted to 9 by addition of a solution of 1 M $NaHCO_3$ and the aqueous layer extracted with ethyl acetate. The combined organic phases were dried over $MgSO_4$ and concentrated by evaporation under reduced pressure. The crude material was dissolved in a mixture of acetic anhydride (40 ml) and acetic acid (20 ml) and cooled to 0° C. Sodium nitrite (7.4 g, 107 mmol) were added in portions. After the addition the reaction was warmed to rt and stirred for 3 h. The solution was concentrated by evaporation under reduced pressure, the pH adjusted to 9 by addition of a solution of 1 M $NaHCO_3$ and the aqueous layer extracted with ethyl acetate. The resulting brown oil was taken up in a mixture of THF:water (3:1, 20 mL) and a pre-prepared solution of LiOH (2.1 g, 48.7 mmol) in hydrogen peroxide (10 mL, 30% solution in water) was added drop wise. The mixture was stirred at rt for 30 min. The solution was concentrated by evaporation under reduced pressure, the pH adjusted to 4 by addition of acetic acid and the aqueous layer extracted with ethyl acetate. The intermediate was not further purified but used as crude material for further modification. MS ($ES^-$): 404 (M−H).

b) (2-Amino-4,5-difluoro-phenyl)-carbamic acid tert-butyl ester 4,5-Difluoro-2-nitro-phenylamine (6.0 g, 34 mmol, 1 equiv.) was added to a solution of di-tert-butyl dicarbonate (14.8 g, 68 mmol, 2 equiv.) and DMAP (211 mg, 0.2 mmol, 0.05 in THF (100 mL) and the mixture was stirred at room temperature for 72 hours. The solvent was evaporated and the crude extracted from ethylacetate and aq. $NaHCO_3$. The residue was taken up in DCM and cooled to 0° C. Trifluoroacetic acid (7.75 g, 68 mmol, 2 equiv) were added slowly and the mixture stirred for 48 h at 0° C. 2 N NaOH was added to adjust the pH to 7. The organic layer was separated and evaporated. The residue was taken up in ethyl acetate and the product extracted from aq. $NaHCO_3$. The intermediate was isolated via Kieselgel chromatography. 4.28 g (16 mmol, 1 equiv.) were dissolved in DMF (50 ml) and 13 ml of a saturated $NH_4Cl$ solution added. Zink powder (5.1 g, 78 mmol, 5 equiv.) was added and the suspension stirred for 30 minutes at 80° C. and another 2 hours at room temperature. The remaining solid was filtered off and the organic layer evaporated. The product was extracted from ethyl actetate and aq. $NaHCO_3$ and further purified via Kieselgel chromatography.

Example 2

6-{2-[2-(6-Chloro-pyridin-3-yl)-5,6-difluoro-benzoimidazol-1-yl]-2-cyclohexyl-acetylamino}-nicotinic acid The title compound was prepared in analogy to Example 1, replacing 4-amino-3-methyl-benzoic acid methyl ester with 6-amino-nicotinic acid methyl ester. MS ($ES^+$): 527 (M+H).

Example 3

4-{2-[2-(6-Chloro-pyridin-3-yl)-5,6-difluoro-benzoimidazol-1-yl]-2-cyclohexyl-acetylamino}-3-fluoro-benzoic acid The title compound was prepared in analogy to example 1, replacing 4-amino-3-chloro-benzoic acid methyl ester with 4-amino-3-fluoro-benzoic acid methyl ester. MS ($ES^+$): 544 (M+H).

Example 4

4-{2-[2-(6-Chloro-pyridin-3-yl)-5,6-difluoro-benzoimidazol-1-yl]-2-cyclohexyl-acetylamino}-3-methyl-benzoic acid The title compound was prepared in analogy to example 1, replacing 4-amino-3-fluoro-benzoic acid methyl ester with 4-amino-3-methyl-benzoic acid methyl ester. MS ($ES^+$): 540 (M+H).

Example 5

(−)-3-Chloro-4-{2-[2-(6-chloro-pyridin-3-yl)-5,6-difluoro-benzoimidazol-1-yl]-2-cyclohexyl-acetylamino}-benzoic acid The title compound was prepared in analogy to example 1 conducting separation of the stereoisomers by chiral preparative HPLC. MS (ES+): 560 (M+H).

Example 6

(+)-3-Chloro-4-{2-[2-(6-chloro-pyridin-3-yl)-5,6-difluoro-benzoimidazol-1-yl]-2-cyclohexyl-acetylamino}-benzoic acid The title compound was prepared in analogy to example 1 conducting separation of the stereoisomers by chiral preparative HPLC. MS (ES+): 560 (M+H).

Intermediate trans-4-Isocyano-cyclohexanecarboxylic acid methyl ester trans-4-Amino-cyclohexanecarboxylic acid methyl ester hydrochloride (2 g, 10.3 mmol) was dissolved in a mixture of DMF (10 ml) and DIPEA (2 ml). Ethylformiate (5 ml, 62 mmol) were added and the mixture heated to 75° C. overnight. The solvent was evaporated and the crude product extracted from ethyl acetate. A brown oil was obtained. MS (ES+): 186 (M+H). The crude material was dissolved in dichloromethane (15 ml). Triethylamine (1.5 ml) was added and the reaction mixture cooled to 0° C. Triphosgene (470 mf, 1.6 mmol) was dissolved in dichloromethane (4 ml) and added drop wise to the reaction mixture. This was warmed up to rt and stirred for 1 h. The product was isolated directly via Kieselgel chromatography using ethyl acetate as an eluent. The intermediate was used without further characterization.

Example 7 trans-4-{2-[2-(6-Chloro-pyridin-3-yl)-5,6-difluoro-benzoimidazol-1-yl]-2-cyclohexyl-acetylamino}-cyclohexanecarboxylic acid To a solution of (2-amino-4,5-difluoro-phenyl)-carbamic acid tert-butyl ester (0.2 g, 0.82 mmol) in methanol (4 mL) were added cyclohexanecarbaldehyde (0.16 mL, 1.22 mmol, 1.5 equiv.), 6-chloro-nicotinic acid (0.13 g, 0.82 mmol, 1.0 equiv.) and trans-4-Isocyano-cyclohexanecarboxylic acid methyl ester (0.137 mg, 0.82 mmol, 1.0 equiv.) and stirred at rt for 16 h. A solution of 4 M HCl in dioxane (4 mL) was added and the reaction mixture stirred at rt for 3 h. The solution was concentrated by evaporation under reduced pressure, the pH adjusted to 9 by addition of a solution of 1 M NaHCO$_3$ and the aqueous layer extracted with ethyl acetate. The combined organic phases were dried over MgSO$_4$ and concentrated by evaporation under reduced pressure. The crude material was dissolved in methanol (15 ml) and NaOH (5 ml) and DMF (1 ml) were added and the mixture heated to 50° C. overnight. The pH was adjusted to 4. A light brown solid appeared which was further purified by preparative HPLC. MS (ES+): 532 (M+H).

Example 8

2-Cyclohexyl-2-[2-(2,6-dimethoxy-pyridin-3-yl)-5,6-difluoro-benzoimidazol-1-yl]-N-(trans-4-hydroxy-cyclohexyl)-acetamide To a solution of cyclohexyl-[2-(2,6-dimethoxy-pyridin-3-yl)-5,6-difluoro-benzoimidazol-1-yl]-acetic acid (300 mg, 0.70 mmol, 1.0 equiv) in DCM (5 mL) was added triethylamine (142.1 mg, 194.7 µL, 1.39 mmol, 2.0 equiv) and HATU (341.6 mg, 0.90 mmol, 1.3 equiv) and the mixture stirred at 40° C. After 15 min, trans-4-amino-cyclohexanol hydrochloride (137.04 mg, 0.90 mmol, 1.3 equiv; [CAS RN 50910-54-8]) was added and stirring continued at 50° C. for 2 h. Removal of the solvent mixture under reduced pressure and purification by silica column chromatography using a MPLC system (CombiFlash Companion, Isco Inc.) eluting with a gradient of heptane/ethyl acetate yielded 0.33 g (90%) of the title compound. MS (ES+): 529 (M+H).

Intermediates a) N-Benzyl-2-cyclohexyl-2-[2-(2,6-dimethoxy-pyridin-3-yl)-5,6-difluoro-benzoimidazol-1-yl]-acetamide To a solution of (2-amino-4,5-difluoro-phenyl)-carbamic acid tert-butyl ester (2.50 g, 10.24 mmol, 1.0 equiv; example 1, intermediate b) in methanol (30 mL) was added cyclohexanecarbaldehyde (1.15 g, 1.23 mL, 10.24 mmol, 1.0 equiv; [2043-61-0]) and the mixture stirred at rt. After 30 min, 2,6-dimethoxy-nicotinic acid (1.88 g, 10.24 mmol, 1.0 equiv; [CAS RN 16727-43-8]) and isocyanomethyl-benzene (1.20 g, 1.25 mL, 10.24 mmol, 1.0 equiv; [931-53-3]) were added and stirring continued at rt for 2 h. A solution of 4 M HCl in dioxane (20 mL) was added and the reaction mixture stirred at rt overnight. The solution was concentrated by evaporation under reduced pressure, the pH adjusted to 9 by addition of a solution of 1 M NaHCO$_3$ and the aqueous layer extracted with dichloromethane. The combined organic phases were dried over MgSO$_4$ and concentrated by evaporation under reduced pressure. The crude material was purified by silica column chromatography using a MPLC system (CombiFlash Companion, Isco Inc.) eluting with a gradient of heptane/ethyl acetate to give 3.57 g (60%) of the title compound. MS (ES+): 522 (M+H).

b) Cyclohexyl-[2-(2,6-dimethoxy-pyridin-3-yl)-5,6-difluoro-benzoimidazol-1-yl]-acetic acid To a solution of N-benzyl-2-cyclohexyl-2-[2-(2,6-dimethoxy-pyridin-3-yl)-5,6-difluoro-benzoimidazol-1-yl]-acetamide (3.50 g, 6.72 mmol, 1.0 equiv) in a mixture of acetic acid (25 mL) and acetic acid anhydride (50 mL) was added at 0° C. in several small portions sodium nitrite (10.20 g, 147.91 mmol, 22.0 equiv) within 1 h. The reaction mixture was stirred overnight allowing to warm up to rt. The solution was concentrated by evaporation under reduced pressure, the pH adjusted to 9 by addition of a solution of 1 M NaHCO$_3$ and the aqueous layer extracted with diethyl ether. The combined organic phases were dried over MgSO$_4$ and concentrated by evaporation under reduced pressure. The crude material was taken up in a mixture of THF:water (3:1, 40 mL) and a pre-prepared solution of LiOH (1.61 g, 67.23 mmol, 10.0 equiv) in hydrogen peroxide (15.24 g, 13.73 mL, 134.46 mmol, 20.0 equiv; 30% solution in water) was added and stirred at rt for 30 min. The solution was concentrated by evaporation under reduced pressure, the pH adjusted to 4 by addition of 1 M HCl and the aqueous layer extracted with diethyl ether. The combined organic phases were dried over MgSO₄ and concentrated by evaporation under reduced pressure. Purification by silica column chromatography using a MPLC system (CombiFlash Companion, Isco Inc.) eluting with a gradient of dichloromethane/methanol yielded 1.67 g (57%) of the title compound. MS (ES⁺): 432 (M+H).

Example 9

(+)-2-Cyclohexyl-2-[2-(2,6-dimethoxy-pyridin-3-yl)-5,6-difluoro-benzoimidazol-1-yl]-N-(trans-4-hydroxy-cyclohexyl)-acetamide The title compound was prepared in accordance with example 8 conducting separation of the stereoisomers by chiral preparative HPLC (Chiralpak-AD column) eluting with a gradient of ethanol/heptane. MS (ES⁺): 530 (M+H).

Example 10 trans-4-{2-Cyclohexyl-2-[2-(2,6-dimethoxy-pyridin-3-yl)-5,6-difluoro-benzoimidazol-1-yl]-acetylamino}-cyclohexanecarboxylic acid To a solution of 4-{2-cyclohexyl-2-[2-(2,6-dimethoxy-pyridin-3-yl)-5,6-difluoro-benzoimidazol-1-yl]-acetylamino}-cyclohexanecarboxylic acid ethyl ester (350 mg, 0.60 mmol, 1.0 equiv) in a mixture of acetonitrile/water (2:1, 5 mL) was added a solution of aqueous 6 M NaOH (0.3 mL, 1.80 mmol, 3.0 equiv) and the reaction mixture heated by microwave irradiation to 100° C. for 30 min. The solvent was removed under reduced pressure and the crude reaction mixture adjusted to pH=3 by addition of a solution of 1 M HCl and the aqueous layer extracted with a mixture of dichloromethane/isopropanol (4:1). The combined organic phases were dried over MgSO₄, concentrated by evaporation under reduced pressure and the crude material purified over a short silica column eluting with a gradient of dichloromethane/methanol yielding 0.31 g (93%) of the title compound. MS (ES⁺): 558 (M+H).

Intermediate

4-{2-Cyclohexyl-2-[2-(2,6-dimethoxy-pyridin-3-yl)-5,6-difluoro-benzoimidazol-1-yl]-acetylamino}-cyclohexanecarboxylic acid ethyl ester The title compound was prepared in analogy to example 8 replacing trans-4-amino-cyclohexanol hydrochloride with trans-4-amino-cyclohexanecarboxylic acid ethyl ester ([CAS RN 1678-68-8]). MS (ES⁺): 585 (M+H).

Example 11

(+)-trans-4-{2-Cyclohexyl-2-[2-(2,6-dimethoxy-pyridin-3-yl)-5,6-difluoro-benzoimidazol-1-yl]-acetylamino}-cyclohexanecarboxylic acid The title compound was prepared in accordance with example 10 conducting separation of the stereoisomers by chiral preparative HPLC (Chiralpak-AD column) eluting with a gradient of ethanol (+0.5% formic acid)/heptane. MS (ES⁺): 557 (M+H).

Example 12

4-{2-Cyclohexyl-2-[2-(2,6-dimethoxy-pyridin-3-yl)-5,6-difluoro-benzoimidazol-1-yl]-acetylamino}-3-methyl-benzoic acid The title compound was prepared in analogy to example 10 followed by purification with preparative HPLC on reversed phase eluting with a gradient of acetonitrile/water. MS (ES⁺): 566 (M+H).

Intermediate

4-{2-Cyclohexyl-2-[2-(2,6-dimethoxy-pyridin-3-yl)-5,6-difluoro-benzoimidazol-1-yl]-acetylamino}-3-methyl-benzoic acid methyl ester The title compound was prepared in analogy to example 8 replacing trans-4-amino-cyclohexanol hydrochloride with 4-amino-3-methyl-benzoic acid methyl ester ([CAS RN 18595-14-7]). MS (ES⁺): 579 (M+H).

Example 13

4-{2-Cyclohexyl-2-[2-(2,6-dimethoxy-pyridin-3-yl)-5,6-difluoro-benzoimidazol-1-yl]-acetylamino}-3-fluoro-benzoic acid The title compound was prepared in analogy to example 10 followed by purification with preparative HPLC on reversed phase eluting with a gradient of acetonitrile/water. MS (ES⁺): 569 (M+H).

Intermediate

4-{2-Cyclohexyl-2-[2-(2,6-dimethoxy-pyridin-3-yl)-5,6-difluoro-benzoimidazol-1-yl]-acetylamino}-3-fluoro-benzoic acid ethyl ester The title compound was prepared in analogy to example 8 replacing trans-4-amino-cyclohexanol hydrochloride with 4-amino-3-fluoro-benzoic acid ethyl ester ([CAS RN 73792-12-8]). MS (ES⁺): 597 (M+H).

Example 14 trans-4-{2-Cyclohexyl-2-[2-(2,6-dimethoxy-pyridin-3-yl)-5-fluoro-benzoimidazol-1-yl]-acetylamino}-cyclohexanecarboxylic acid The title compound was prepared in analogy to example 10 followed by purification with preparative HPLC on reversed phase eluting with a gradient of acetonitrile/water. MS (ES⁺): 540 (M+H).

Intermediates a) N-Benzyl-2-cyclohexyl-2-[2-(2,6-dimethoxy-pyridin-3-yl)-5-fluoro-benzoimidazol-1-yl]-acetamide The title compound was prepared in analogy to example 8, intermediate a, replacing (2-amino-4,5-difluoro-phenyl)-carbamic acid tert-butyl ester (example 1, intermediate b) with (2-amino-5-fluoro-phenyl)-carbamic acid tert-butyl ester (prepared as described in M. J. Bamford, M. J. Alberti, N. Bailey, S. Davies, D. K. Dean, A. Gaiba, S. Garland, J. D. Harling, D. K. Jung, T. A. Panchal, C. A. Parr, J. G. Steadman, A. K. Takle, J. T. Townsend, D. M. Wilson, J. Witherington *Bioorg. Med. Chem. Lett.* 2005, 15, 3402-3406). MS (ES$^+$): 504 (M+H).

b) Cyclohexyl-[2-(2,6-dimethoxy-pyridin-3-yl)-5-fluoro-benzoimidazol-1-yl]-acetic acid The title compound was prepared in analogy to example 8, intermediate b. MS (ES$^+$): 415 (M+H).

c) 4-{2-Cyclohexyl-2-[2-(2,6-dimethoxy-pyridin-3-yl)-5-fluoro-benzoimidazol-1-yl]-acetylamino}-cyclohexanecarboxylic acid ethylamide The title compound was prepared in analogy to example 8 replacing trans-4-amino-cyclohexanol hydrochloride with trans-4-amino-cyclohexanecarboxylic acid ethyl ester ([CAS RN 1678-68-8]). MS (ES$^+$): 568 (M+H).

Example 15

(−)-trans-4-{2-Cyclohexyl-2-[2-(2,6-dimethoxy-pyridin-3-yl)-5-fluoro-benzoimidazol-1-yl]-acetylamino}-cyclohexanecarboxylic acid The title compound was prepared in analogy to example 14 conducting separation of the stereoisomers by chiral preparative HPLC (Chiralpak-AD column) eluting with a gradient of isopropanol (+0.5% formic acid)/heptane. MS (ES$^+$): 540 (M+H).

Example 16

(−)-trans-4-{2-[2-(4-Chloro-phenyl)-5,6-difluoro-benzoimidazol-1-yl]-2-cyclohexyl-acetylamino}-cyclohexanecarboxylic acid The title compound was prepared in analogy to example 8 replacing cyclohexyl-[2-(2,6-dimethoxy-pyridin-3-yl)-5,6-difluoro-benzoimidazol-1-yl]-acetic acid with [2-(4-chloro-phenyl)-5,6-difluoro-benzoimidazol-1-yl]-cyclohexyl-acetic acid (example 22, intermediate c) and trans-4-amino-cyclohexanol hydrochloride with trans-4-amino-cyclohexanecarboxylic acid ethyl ester ([CAS RN 1678-68-8]), followed by subsequent ester hydrolysis in analogy to example 10. Purification was conducted with chiral preparative HPLC (Chiralpak-AD column) eluting with a gradient of ethanol (+0.5% formic acid)/heptane. MS (ES$^+$): 530 (M+H).

Example 17

(trans-4-{2-[2-(4-Chloro-phenyl)-5,6-difluoro-benzoimidazol-1-yl]-2-cyclohexyl-acetylamino}-cyclohexyl)-acetic acid The title compound was prepared in analogy to example 10 followed by purification with preparative HPLC on reversed phase eluting with a gradient of acetonitrile/water. MS (ES$^+$): 544 (M+H).

Intermediate (4-{2-[2-(4-Chloro-phenyl)-5,6-difluoro-benzoimidazol-1-yl]-2-cyclohexyl-acetylamino}-cyclohexyl)-acetic acid ethyl ester The title compound was prepared in analogy to example 8 replacing cyclohexyl-[2-(2,6-dimethoxy-pyridin-3-yl)-5,6-difluoro-benzoimidazol-1-yl]-acetic acid with [2-(4-chloro-phenyl)-5,6-difluoro-benzoimidazol-1-yl]-cyclohexyl-acetic acid (example 22, intermediate c) and trans-4-amino-cyclohexanol hydrochloride with trans-(4-amino-cyclohexyl)-acetic acid ethyl ester hydrochloride ([CAS RN 76308-26-4]). MS (ES$^+$): 572 (M+H).

Example 18

(+)-trans-(4-{2-[2-(4-Chloro-phenyl)-5,6-difluoro-benzoimidazol-1-yl]-2-cyclohexyl-acetylamino}-cyclohexyl)-acetic acid The title compound was prepared in accordance with example 17 conducting separation of the stereoisomers by chiral preparative HPLC (Chiralcel-ODH column) eluting with a gradient of isopropanol (+0.5% trifluoroacetic acid)/heptane. MS (ES$^+$): 544 (M+H).

Example 19

4-{2-Bicyclo[2.2.1]hept-7-yl-2-[2-(4-chloro-phenyl)-5,6-difluoro-benzoimidazol-1-yl]-acetylamino}-benzoic acid The title compound was prepared in analogy to example 10 followed by purification with preparative HPLC on reversed phase eluting with a gradient of acetonitrile/water. MS (ES$^+$): 536 (M+H).

Intermediate

4-{2-Bicyclo[2.2.1]hept-7-yl-2-[2-(4-chloro-phenyl)-5,6-difluoro-benzoimidazol-1-yl]-acetylamino}-benzoic acid methyl ester The title compound was prepared in analogy to example 8, intermediate a, replacing cyclohexanecarbaldehyde with bicyclo[2.2.1]heptane-7-carbaldehyde ([CAS RN 53291-20-6]), 2,6-dimethoxy-nicotinic acid with 4-chloro-benzoic acid ([CAS RN 74-11-3]) and isocyanomethyl-benzene with 4-isocyano-benzoic acid methyl ester ([CAS RN 198476-21-0]) followed by purification with preparative HPLC on reversed phase eluting with a gradient of acetonitrile/water. MS (ES$^+$): 550 (M+H).

Example 20

(−)-trans-4-({2-[2-(4-Chloro-phenyl)-5-fluoro-benzoimidazol-1-yl]-2-cyclohexyl-acetylamino}-methyl)-cyclohexanecarboxylic acid The title compound was prepared in analogy to example 10 followed by purification with chiral preparative HPLC (Chiralpak-AD column) eluting with a gradient of isopropanol (+0.5% formic acid)/heptane. MS (ES$^+$): 527 (M+H).

Intermediate 4-({2-[2-(4-Chloro-phenyl)-5-fluoro-benzoimidazol-1-yl]-2-cyclohexyl-acetylamino}-methyl)-cyclohexanecarboxylic acid methyl ester The title compound was prepared in analogy to example 8, intermediate a, replacing (2-amino-4,5-difluoro-phenyl)-carbamic acid tert-butyl ester with (2-amino-5-fluoro-phenyl)-carbamic acid tert-butyl ester (prepared as described in M. J. Bamford, M. J. Alberti, N. Bailey, S. Davies, D. K. Dean, A. Gaiba, S. Garland, J. D. Harling, D. K. Jung, T. A. Panchal, C. A. Parr, J. G. Steadman, A. K. Takle, J. T. Townsend, D. M. Wilson, J. Witherington *Bioorg. Med. Chem. Lett.* 2005, 15, 3402-3406), 2,6-dimethoxy-nicotinic acid with 4-chlorobenzoic acid ([CAS RN 74-11-3]) and isocyanomethyl-benzene with 4-isocyanomethyl-cyclohexanecarboxylic acid methyl ester ([CAS RN 730964-84-8]) followed by purification with preparative HPLC on reversed phase eluting with a gradient of acetonitrile/water. MS (ES$^+$): 540 (M+H).

Example 21

3-Chloro-4-{2-[2-(4-chloro-phenyl)-5-fluoro-benzoimidazol-1-yl]-2-cyclohexyl-acetylamino}-benzoic acid The title compound was prepared in analogy to example 10 followed by purification with preparative HPLC on reversed phase eluting with a gradient of acetonitrile/water. MS (ES$^+$): 542 (M+H).

Intermediate

3-Chloro-4-{2-[2-(4-chloro-phenyl)-5-fluoro-benzoimidazol-1-yl]-2-cyclohexyl-acetylamino}-benzoic acid methyl ester The title compound was prepared in analogy to example 8, intermediate a, replacing (2-amino-4,5-difluoro-phenyl)-carbamic acid tert-butyl ester with (2-amino-5-fluoro-phenyl)-carbamic acid tert-butyl ester (prepared as described in M. J. Bamford, M. J. Alberti, N. Bailey, S. Davies, D. K. Dean, A. Gaiba, S. Garland, J. D. Harling, D. K. Jung, T. A. Panchal, C. A. Parr, J. G. Steadman, A. K. Takle, J. T. Townsend, D. M. Wilson, J. Witherington *Bioorg. Med. Chem. Lett.* 2005, 15, 3402-3406), 2,6-dimethoxy-nicotinic acid with 4-chlorobenzoic acid ([CAS RN 74-11-3]) and isocyanomethyl-benzene with 3-chloro-4-isocyano-benzoic acid methyl ester (prepared in analogy to 4-isocyano-benzoic acid methyl ester ([CAS RN 198476-21-0]) from 4-amino-3-chloro-benzoic acid methyl ester ([CAS RN 84228-44-4]) as described in S. Kamijo, T. Jin, Y. Yamamoto *J. Am. Chem. Soc.* 2001, 123, 9453-9454) followed by purification with preparative HPLC on reversed phase eluting with a gradient of acetonitrile/water. MS (ES$^+$): 554 (M+H).

Example 22

4-{2-[2-(4-Chloro-phenyl)-5,6-difluoro-benzoimidazol-1-yl]-2-cyclohexyl-acetylamino}-benzoic acid To the solution of 4-{2-[2-(4-chloro-phenyl)-5,6-difluoro-benzoimidazol-1-yl]-2-cyclohexyl-acetylamino}-benzoic acid ethyl ester (intermediate d) in 25 ml dioxan, 25 ml water and 0.57 g (13.6 mmol) lithium hydroxide monohydrate were added. The solution was stirred for 2 h at 100° C. After cooling to room temperature, 16 ml 1M aqueous hydrochloric acid were added upon stirring. The suspension was filtered, the filter cake washed with water and dried under high vacuum to give 2.46 g (99%) of the desired compound as colorless solid.

MS (ES$^-$): 524 (M−H)

Intermediates a)

2-(4-Chloro-phenyl)-5,6-difluoro-1H-benzoimidazole

The mixture of 50.7 g (0.35 mol) 1,2-diamino-4,5-difluorobenzene, 55.1 g (0.35 mol) 4-chlorobenzoic acid and 507 g polyphosphoric acid was heated to 160° C. and stirred at this temperature for 90 min. After cooling to 55° C., 1000 mL water and 500 mL ethyl acetate were added. Under ice cooling ca 1000 mL 32% aqueous sodium hydroxide solution was added (pH ca 9). The suspension was filtered over dicalite and the filter cake was washed with 1.5 L ethyl acetate. The phases were separated and the aqueous phase was washed with 0.5 L ethyl acetate. The organic phases were washed with 1M aqueous sodium hydroxide solution and brine, dried over magnesium sulfate and filtered. To the solution, silica gel was added and the solvent evaporated. The crude adsorbed product was purified by column chromatography over silica gel using a gradient of n-heptane:ethyl acetate (v/v, 4:1 to 1:1) as eluant. The fractions containing the product in pure form were pooled and evaporated. The remaining fractions were dissolved in ethyl acetate, washed twice with 1M aqueous sodium hydroxide solution and brine, the combined aqueous layers extracted once with ethyl acetate and the combined organic layers dried over magnesium sulfate and filtered. Chromatography over silica gel afforded a second batch of compound. Total yield: 75 g (80%) light yellow solid. MS (ES$^+$): 265 (M+H).

b) [2-(4-Chloro-phenyl)-5,6-difluoro-benzoimidazol-1-yl]-cyclohexyl-acetic acid ethyl ester To the solution of 75 g (0.28 mol) 2-(4-chloro-phenyl)-5,6-difluoro-1H-benzoimidazole in 750 ml N,N-dimethylformamide 116 g (0.33 mol) cesium carbonate and 88 g (0.35 mol) bromo-cyclohexyl-acetic acid ethyl ester (commercially available) were added. The mixture was heated to 100° C. and after stirring for 90 min. another 116 g cesium carbonate and 88 g bromo-cyclohexyl-acetic acid ethyl ester were added. After 6 h another 116 g cesium carbonate and 88 g bromo-cyclohexyl-acetic acid ethyl ester were added. After 22 h (total reaction time) the reaction mixture was cooled to 30° C. and was poured on 1 L ice water and 2 L ethyl acetate. The phases were separated and the aqueous phase extracted with 500 mL ethyl acetate. The combined organic phases were washed three times with 500 ml ice water and once with brine, dried over magnesium sulfate and filtered. To the solution, silica gel was added and the solvent evaporated. The crude adsorbed product was purified by column chromatography over silica gel using n-heptane:ethyl acetate (9:1 v/v) as eluant. The product-containing fractions were pooled and the solvent evaporated until a suspension had formed. The suspension was cooled in an ice bath and filtered to give 92 g (75%) of the desired product as colorless solid. MS (ES$^+$): 433 (M+H).

c) [2-(4-Chloro-phenyl)-5,6-difluoro-benzoimidazol-1-yl]-cyclohexyl-acetic acid

To the solution of 24 g (0.055 mol) [2-(4-chloro-phenyl)-5,6-difluoro-benzoimidazol-1-yl]-cyclohexyl-acetic acid ethyl ester in 240 ml dioxan, 240 ml water and 7.0 g (0.166 mol) lithium hydroxide monohydrate were added. The solution was stirred for 2 h at 100° C. After cooling to room temperature the organic solvent was evaporated. Under stirring 162 ml 1M hydrochloric acid were added. The resulting suspension was filtered, the filter cake washed with water and dried under high vacuum to give 21.7 g (95%) of the desired compound as a white solid. MS (ES⁻): 403 (M−H).

d) 4-{2-[2-(4-Chloro-phenyl)-5,6-difluoro-benzoimidazol-1-yl]-2-cyclohexyl-acetylamino}-benzoic acid ethyl ester The solution of 3.0 g (7.4 mmol) [2-(4-chloro-phenyl)-5,6-difluoro-benzoimidazol-1-yl]-cyclohexyl-acetic acid in 5.4 ml thionylchloride was stirred under reflux. After 1 h the volatile components were removed at a rotary evaporator, the residue taken up in toluene and evaporated (three times). The remaining oil was dissolved in 30 ml dichloromethane, cooled to 0° C. and added dropwise on a solution of ethyl 4-aminobenzoate (1.35 g, 8.1 mmol) and 2.72 g (22.2 mmol) 4-dimethylaminopyridine dissolved in 30 ml dichloromethane. The cooling bath was removed and stirring was continued for another 4 h. The reaction was poured on 25% aqueous hydrochloric acid solution, the phases separated and the aqueous phase extracted with dichloromethane. The combined organic phases were washed with brine, dried over magnesium sulfate, filtered and evaporated. The residue was purified by column chromatography on silica gel using heptane:ethyl acetate (1:0 to 1:1 v/v) as eluant to afford the title compound as a colorless solid (2.6 g, 62%). MS (ES⁺): 552 (M+H).

Examples 23 and 24

The title compounds were obtained by separation of the stereoisomers of 4-{2-[2-(4-chloro-phenyl)-5,6-difluoro-benzoimidazol-1-yl]-2-cyclohexyl-acetylamino}-benzoic acid by chiral preparative HPLC (Chiralpak-AD column).

(+)-4-{2-[2-(4-Chloro-phenyl)-5,6-difluoro-benzoimidazol-1-yl]-2-cyclohexyl-acetylamino}-benzoic acid Colorless solid. MS (TS) m/e (M−H)⁻: 522.2.

(−)-4-{2-[2-(4-Chloro-phenyl)-5¦6-difluoro-benzoimidazol-1-yl]-2-cyclohexyl-acetylamino}-benzoic acid Colorless solid. MS (TS) m/e (M−H)⁻: 522.2.

Intermediates a) 2-(4-Chloro-phenyl)-5,6-difluoro-1H-benzoimidazole

The mixture of 50.7 g (0.35 mol) 1,2-diamino-4,5-difluorobenzene, 55.1 g (0.35 mol) 4-chlorobenzoic acid and 507 g polyphosphoric acid was heated to 160° C. and stirred at this temperature for 90 min. After cooling to 55° C., 1000 mL water and 500 mL ethyl acetate were added. Under ice cooling ca 1000 mL 32% aqueous sodium hydroxide solution was added (pH ca 9). The suspension was filtered over dicalite and the filter cake was washed with 1.5 L ethyl acetate. The phases were separated and the aqueous phase was washed with 0.5 L ethyl acetate. The organic phases were washed with 1M aqueous sodium hydroxide solution and brine, dried over magnesium sulfate and filtered. To the solution, silica gel was added and the solvent evaporated. The crude adsorbed product was purified by column chromatography over silica gel using a gradient of n-heptane:ethyl acetate (v/v, 4:1 to 1:1) as eluant. The fractions containing the product in pure form were pooled and evaporated. The remaining fractions were dissolved in ethyl acetate, washed twice with 1M aqueous sodium hydroxide solution and brine, the combined aqueous layers extracted once with ethyl acetate and the combined organic layers dried over magnesium sulfate and filtered. Chromatography over silica gel afforded a second batch of compound. Total yield: 75 g (80%) light yellow solid.

MS (TS) m/e (M+H)⁺: 264.9.

b) [2-(4-Chloro-phenyl)-5,6-difluoro-benzoimidazol-1-yl]-cyclohexyl-acetic acid ethyl ester To the solution of 75 g (0.28 mol) 2-(4-chloro-phenyl)-5,6-difluoro-1H-benzoimidazole in 750 ml N,N-dimethylformamide 116 g (0.33 mol) cesium carbonate and 88 g (0.35 mol) bromo-cyclohexyl-acetic acid ethyl ester (commercially available) were added. The mixture was heated to 100° C. and after stirring for 90 min. another 116 g cesium carbonate and 88 g bromo-cyclohexyl-acetic acid ethyl ester were added. After 6 h another 116 g cesium carbonate and 88 g bromo-cyclohexyl-acetic acid ethyl ester were added. After 22 h (total reaction time) the reaction mixture was cooled to 30° C. and was poured on 1 L ice water and 2 L ethyl acetate. The phases were separated and the aqueous phase extracted with 500 mL ethyl acetate. The combined organic phases were washed three times with 500 ml ice water and once with brine, dried over magnesium sulfate and filtered. To the solution, silica gel was added and the solvent evaporated. The crude adsorbed product was purified by column chromatography over silica gel using n-heptane:ethyl acetate (9:1 v/v) as eluant. The product-containing fractions were pooled and the solvent evaporated until a suspension had formed. The suspension was cooled in an ice bath and filtered to give 92 g (75%) of the desired product as colorless solid.

MS (TS) m/e (M+H)⁺: 433.1.

c) [2-(4-Chloro-phenyl)-5,6-difluoro-benzoimidazol-1-yl]-cyclohexyl-acetic acid

To the solution of 24 g (0.055 mol) [2-(4-chloro-phenyl)-5,6-difluoro-benzoimidazol-1-yl]-cyclohexyl-acetic acid ethyl ester in 240 ml dioxan, 240 ml water and 7.0 g (0.166 mol) lithium hydroxide monohydrate were added. The solution was stirred for 2 h at 100° C. After cooling to room temperature the organic solvent was evaporated. Under stirring 162 ml 1M hydrochloric acid were added. The resulting suspension was filtered, the filter cake washed with water and dried under high vacuum to give 21.7 g (95%) of the desired compound as a white solid.

MS (TS) m/e (M−H)⁻ 403.2.

d) 4-{2-[2-(4-Chloro-phenyl)-5,6-difluoro-benzoimidazol-1-yl]-2-cyclohexyl-acetylamino}-benzoic acid ethyl ester The solution of 3.0 g (7.4 mmol) [2-(4-chloro-phenyl)-5, 6-difluoro-benzoimidazol-1-yl]-cyclohexyl-acetic acid in 5.4 ml thionylchloride was stirred under reflux. After 1 h the volatile components were removed at a rotary evaporator, the residue taken up in toluene and evaporated (three times). The remaining oil was dissolved in 30 ml dichloromethane, cooled to 0° C. and added dropwise on a solution of ethyl 4-aminobenzoate (1.35 g, 8.1 mmol) and 2.72 g (22.2 mmol) 4-dimethylaminopyridine dissolved in 30 ml dichloromethane. The cooling bath was removed and stirring was continued for another 4 h. The reaction was poured on 25% aqueous hydrochloric acid solution, the phases separated and the aqueous phase extracted with dichloromethane. The combined organic phases were washed with brine, dried over magnesium sulfate, filtered and evaporated. The residue was purified by column chromatography on silica gel using heptane:ethyl acetate (1:0 to 1:1 v/v) as eluant to afford the title compound as a colorless solid (2.6 g, 62%).

MS (TS) m/e (M+H)$^+$552.1

Example 25

4-{2-[2-(4-Chloro-phenyl)-5,6-difluoro-benzoimidazol-1-yl]-2-cyclohexyl-acetylamino}-3-methyl-benzoic acid The compound was prepared in analogy to example 22 from 4-{2-[2-(4-chloro-phenyl)-5,6-difluoro-benzoimidazol-1-yl]-2-cyclohexyl-acetylamino}-3-methyl-benzoic acid methyl ester.

Colorless solid (97%), MS (TS) m/e (M−H)$^-$: 536.3.

Examples 26 and 27

The title compounds were obtained by separation of the stereoisomers of 4-{2-[2-(4-chloro-phenyl)-5,6-difluoro-benzoimidazol-1-yl]-2-cyclohexyl-acetylamino}-3-methyl-benzoic acid by chiral preparative HPLC (Chiralpak-AD column).

(+)-4-{2-[2-(4-Chloro-phenyl)-5,6-difluoro-benzoimidazol-1-yl]-2-cyclohexyl-acetylamino}-3-methyl-benzoic acid Off-white solid (45%). MS (TS) m/e (M−H)$^-$: 536.2.

(−)-4-{2-[2-(4-Chloro-phenyl)-5,6-difluoro-benzoimidazol-1-yl]-2-cyclohexyl-acetylamino}-3-methyl-benzoic acid Off-white solid (42%). MS (TS) m/e (M−H)$^-$: 536.2.

Intermediate

4-{2-[2-(4-Chloro-phenyl)-5,6-difluoro-benzoimidazol-1-yl]-2-cyclohexyl-acetylamino}-3-methyl-benzoic acid methyl ester This compound was prepared in analogy to example 22, intermediate d, from [2-(4-chloro-phenyl)-5,6-difluoro-benzoimidazol-1-yl]-cyclohexyl-acetic acid and methyl 4-amino-3-methylbenzoate.

Colorless solid (97%). MS (TS) m/e (M+H)$^+$: 552.3.

Example 28

3-Chloro-4-{2-[2-(4-chloro-phenyl)-5,6-difluoro-benzoimidazol-1-yl]-2-cyclohexyl-acetylamino}-benzoic acid This compound was prepared in analogy to example 22 from 3-chloro-4-{2-[2-(4-chloro-phenyl)-5,6-difluoro-benzoimidazol-1-yl]-2-cyclohexyl-acetylamino}-benzoic acid methyl ester.

Light yellow solid (91%). MS (TS) m/e (M−H)$^-$: 556.1.

Examples 29 and 30

The title compounds were obtained by separation of the stereoisomers of 3-chloro-4-{2-[2-(4-chloro-phenyl)-5,6-difluoro-benzoimidazol-1-yl]-2-cyclohexyl-acetylamino}-benzoic acid by chiral preparative HPLC (Chiralpak-AD column).

(+)-3-Chloro-4-{2-[2-(4-chloro-phenyl)-5,6-difluoro-benzoimidazol-1-yl]-2-cyclohexyl-acetylamino}-benzoic acid Colorless solid (24%). MS (TS) m/e (M−H)$^-$: 556.0.

(−)-3-Chloro-4-{2-[2-(4-chloro-phenyl)-5,6-difluoro-benzoimidazol-1-yl]-2-cyclohexyl-acetylamino}-benzoic acid Colorless solid (24%). MS (TS) m/e (M−H)$^-$: 556.1.

Intermediate

3-Chloro-4-{2-[2-(4-chloro-phenyl)-5,6-difluoro-benzoimidazol-1-yl]-2-cyclohexyl-acetylamino}-benzoic acid methyl ester This compound was prepared in analogy to example 22, intermediate d, from [2-(4-chloro-phenyl)-5,6-difluoro-benzoimidazol-1-yl]-cyclohexyl-acetic acid and methyl 4-amino-3-chlorobenzoate.

Colorless solid (62%). MS (TS) m/e (M+H)$^+$572.2.

Example 31

4-{2-[2-(4-Chloro-phenyl)-5,6-difluoro-benzoimidazol-1-yl]-2-cyclohexyl-acetylamino}-3-fluoro-benzoic acid This compound was prepared in analogy to example 22 from 4-{2-[2-(4-chloro-phenyl)-5,6-difluoro-benzoimidazol-1-yl]-2-cyclohexyl-acetylamino}-3-fluoro-benzoic acid methyl ester.

Colorless solid (91%). MS (TS) m/e (M−H)$^-$: 540.2.

Examples 32 and 33

The title compounds were obtained by separation of the stereoisomers of 4-{2-[2-(4-Chloro-phenyl)-5,6-difluoro-benzoimidazol-1-yl]-2-cyclohexyl-acetylamino}-3-fluoro-benzoic acid by chiral preparative HPLC (Chiralpak-AD column).

(+)-{2-[2-(4-Chloro-phenyl)-5,6-difluoro-benzoimidazol-1-yl]-2-cyclohexyl-acetylamino}-3-fluoro-benzoic acid Colorless solid (41%). MS (TS) m/e (M–H)⁻ 540.2

(–)-4-{2-[2-(4-Chloro-phenyl)-5I6-difluoro-benzoimidazol-1-yl]-2-cyclohexyl-acetylamino}-3-fluoro-benzoic acid Colorless solid (35%). MS (TS) m/e (M–H)⁻ 540.2

Intermediate

4-{2-[2-(4-Chloro-phenyl)-5,6-difluoro-benzoimidazol-1-yl]-2-cyclohexyl-acetylamino}-3-fluoro-benzoic acid methyl ester This compound was prepared in analogy to example 22, intermediate d, from [2-(4-chloro-phenyl)-5,6-difluoro-benzoimidazol-1-yl]-cyclohexyl-acetic acid, methyl 4-amino-3-fluorobenzoate and using 4-(dimethylamino)pyridine as base.
Colorless foam (70%). MS (TS) m/e (M+H)⁺: 556.1.

Example 34

4-{2-[2-(4-Chloro-phenyl)-5,6-difluoro-benzoimidazol-1-yl]-2-cyclohexyl-acetylamino}-3,5-difluoro-benzoic acid This compound was prepared in analogy to example 22 from 4-{2-[2-(4-chloro-phenyl)-5,6-difluoro-benzoimidazol-1-yl]-2-cyclohexyl-acetylamino}-3,5-difluoro-benzoic acid methyl ester.
Colorless solid (92%). MS (TS) m/e (M–H)⁻: 558.1.

Examples 35 and 36

The title compounds were obtained by separation of the stereoisomers of 4-{2-[2-(4-chloro-phenyl)-5,6-difluoro-benzoimidazol-1-yl]-2-cyclohexyl-acetylamino}-3,5-difluoro-benzoic acid by chiral preparative HPLC (Chiralpak-AD column).

(+)-{2-[2-(4-Chloro-phenyl)-5,6-difluoro-benzoimidazol-1-yl]-2-cyclohexyl-acetylamino}-3,5-difluoro-benzoic acid Colorless solid (10%). MS (TS) m/e (M–H)⁻: 558.1.

(–)-4-{2-[2-(4-Chloro-phenyl)-5,6-difluoro-benzoimidazol-1-yl]-2-cyclohexyl-acetylamino}-3,5-difluoro-benzoic acid Colorless solid (19%). MS (TS) m/e (M–H)⁻: 558.1.

Intermediate

4-{2-[2-(4-Chloro-phenyl)-5,6-difluoro-benzoimidazol-1-yl]-2-cyclohexyl-acetylamino}-3,5-difluoro-benzoic acid methyl ester This compound was prepared in analogy to example 20, intermediate d, from [2-(4-chloro-phenyl)-5,6-difluoro-benzoimidazol-1-yl]-cyclohexyl-acetic acid, 4-amino-3,5-difluoro-benzoic acid methyl ester and using pyridine as a base.
Light yellow foam (73%). MS (TS) m/e (M+H)⁺: 574.3.

Example 37

4-{2-[2-(4-Chloro-phenyl)-5,6-difluoro-benzoimidazol-1-yl]-2-cyclohexyl-acetylamino}-3-cyano-benzoic acid This compound was prepared in analogy to example 22 from 4-{2-[2-(4-chloro-phenyl)-5,6-difluoro-benzoimidazol-1-yl]-2-cyclohexyl-acetylamino}-3-cyano-benzoic acid methyl ester to give the desired compound as colorless solid (27%).
MS (TS) m/e (M–H)⁻: 547.2.

Intermediate

4-{2-[2-(4-Chloro-phenyl)-5,6-difluoro-benzoimidazol-1-yl]-2-cyclohexyl-acetylamino}-3-cyano-benzoic acid methyl ester This compound was prepared in analogy to example 22, intermediate d, from [2-(4-chloro-phenyl)-5,6-difluoro-benzoimidazol-1-yl]-cyclohexyl-acetic acid, 4-amino-3-cyano-benzoic acid methyl ester and N,N-diisopropylethylamine as a base.
Colorless foam (20%). MS (TS) m/e (M+H)⁺: 563.3.

Example 38

3-Chloro-4-{2-[2-(4-chloro-phenyl)-benzoimidazol-1-yl]-2-cyclohexyl-acetylamino}-benzoic acid methyl ester This compound was prepared in analogy to example 22 from 3-chloro-4-{2-[2-(4-chloro-phenyl)-benzoimidazol-1-yl]-2-cyclohexyl-acetylamino}-benzoic acid methyl ester to give the title compound as a colorless solid (60%).
MS (TS) m/e (M–H)⁻: 522.1.

Examples 39 and 40

The title compounds were obtained by separation of the stereoisomers of 3-chloro-4-{2-[2-(4-chloro-phenyl)-benzoimidazol-1-yl]-2-cyclohexyl-acetylamino}-benzoic acid methyl ester by chiral preparative HPLC (Chiralpak-AD column).

(+)-3-Chloro-4-{2-[2-(4-chloro-phenyl)-benzoimidazol-1-yl]-2-cyclohexyl-acetylamino}-benzoic acid methyl ester Colorless solid (21%). MS (TS) m/e (M–H)⁻: 520.2.

(–)-3-Chloro-4-{2-[2-(4-chloro-phenyl)-benzoimidazol-1-yl]-2-cyclohexyl-acetylamino}-benzoic acid methyl ester Colorless solid (29%). MS (TS) m/e (M–H)⁻: 520.2.

Intermediates a) [2-(4-Chloro-phenyl)-benzoimidazol-1-yl]-cyclohexyl-acetic acid ethyl ester This compound was synthesized in analogy to example 22, intermediate b, from 2-(4-chloro-phenyl)-1H-benzoimidazole (commercially available), bromo-cyclohexyl-acetic acid ethyl ester (commercially available) and cesium carbonate, to provide the final compound as a colorless solid (58%).

MS (TS) m/e (M+H)$^+$: 397.2.

b) [2-(4-Chloro-phenyl)-benzoimidazol-1-yl]-cyclohexyl-acetic acid

This compound was synthesized in analogy to example 22, intermediate c, from [2-(4-chloro-phenyl)-benzoimidazol-1-yl]-cyclohexyl-acetic acid ethyl ester to give the desired compound as a colorless solid (99%).

MS (TS) m/e (M−H)$^−$: 367.0.

c) 3-Chloro-4-{2-[2-(4-chloro-phenyl)-benzoimidazol-1-yl]-2-cyclohexyl-acetylamino}-benzoic acid methyl ester The title compound was synthesized in analogy to example 22, intermediate d, from [2-(4-chloro-phenyl)-benzoimidazol-1-yl]-cyclohexyl-acetic acid, 4-amino-3-chloro-benzoic acid and using pyridine as a base.

MS (TS) m/e (M+H)$^+$: 537.4.

Example 41

4-{2-[2-(4-Chloro-phenyl)-5,6-difluoro-benzoimidazol-1-yl]-2-cyclohexyl-acetylamino}-3-methoxy-benzoic acid This compound was synthesized in analogy to example 22 from 4-{2-[2-(4-chloro-phenyl)-5,6-difluoro-benzoimidazol-1-yl]-2-cyclohexyl-acetylamino}-3-methoxy-benzoic acid methyl ester to give the title compound as colorless solid (84%).

MS (TS) m/e (M−H)$^−$: 552.0.

Intermediate

4-{2-[2-(4-Chloro-phenyl)-5,6-difluoro-benzoimidazol-1-yl]-2-cyclohexyl-acetylamino}-3-methoxy-benzoic acid methyl ester This compound was synthesized in analogy to example 20, intermediate d, from [2-(4-chloro-phenyl)-5,6-difluoro-benzoimidazol-1-yl]-cyclohexyl-acetic acid (example 22, intermediate c), 4-amino-3-methoxy-benzoic acid methyl ester and using pyridine as a base to afford the title compound as a colorless solid (74%).

MS m/e (M+H)$^+$: 568.1.

Example 42

4-{2-[2-(4-Chloro-phenyl)-5,6-difluoro-benzoimidazol-1-yl]-2-cyclohexyl-acetylamino}-3-trifluoromethyl-benzoic acid This compound was synthesized in analogy to example 22 from 4-{2-[2-(4-chloro-phenyl)-5,6-difluoro-benzoimidazol-1-yl]-2-cyclohexyl-acetylamino}-3-trifluoromethyl-benzoic acid methyl ester to afford the title compound as a colorless solid (79%).

MS m/e (M+H)$^+$: 590.0.

Intermediate

4-{2-[2-(4-Chloro-phenyl)-5,6-difluoro-benzoimidazol-1-yl]-2-cyclohexyl-acetylamino}-3-trifluoromethyl-benzoic acid methyl ester This compound was synthesized in analogy to example 20, intermediate d, from [2-(4-chloro-phenyl)-5,6-difluoro-benzoimidazol-1-yl]-cyclohexyl-acetic acid (example 20, intermediate c), 4-amino-3-trifluoromethyl-benzoic acid methyl ester and using pyridine as a base to afford the title compound as a colorless solid (74%).

MS m/e (M+H)$^+$: 606.1.

Example 43

4-{2-Cyclohexyl-2-[5,6-difluoro-2-(4-trifluoromethyl-phenyl)-benzoimidazol-1-yl]-acetylamino}-benzoic acid This compound was prepared in analogy to example 22 from 4-{2-cyclohexyl-2-[5,6-difluoro-2-(4-trifluoromethyl-phenyl)-benzoimidazol-1-yl]-acetylamino}-benzoic acid ethyl ester.

Colorless solid (95%). MS (TS) m/e (M−H)$^−$: 555.9.

Intermediate

4-{2-Cyclohexyl-2-[5,6-difluoro-2-(4-trifluoromethyl-phenyl)-benzoimidazol-1-yl]-acetylamino}-benzoic acid ethyl ester The solution of 0.30 g (1.23 mmol) (2-amino-4,5-difluoro-phenyl)-carbamic acid tert-butyl ester and 0.15 ml (0.14 g, 1.23 mmol) cyclohexanecarboxaldehyde was stirred for 10 min. Then, 0.23 g (1.23 mmol) 4-(trifluoromethyl)benzoic acid and after another 5 min. 0.22 g (1.23 mmol) 4-isocyano-benzoic acid ethyl ester were added. After 21 h 3 ml 4M aqueous hydrochloric acid were added and stirring continued for another 16 h. The solvent is evaporated, the residue dissolved in a mixture of acetonitrile, water and N,N-dimethyl-formamide and purified by preparative HPLC to give the desired compound as a colorless solid (7%).

MS m/e (M+H)$^+$: 586.1.

Example 44

4-{2-Cyclohexyl-2-[5-fluoro-2-(4-trifluoromethyl-phenyl)-benzoimidazol-1-yl]-acetylamino}-benzoic acid This compound was prepared in analogy to example 22 from 4-{2-cyclohexyl-2-[5-fluoro-2-(4-trifluoromethyl-phenyl)-benzoimidazol-1-yl]-acetylamino}-benzoic acid ethyl ester.

Colorless solid (64%). MS m/e 538.1 (M−H)$^−$.

Intermediate

4-{2-Cyclohexyl-2-[5-fluoro-2-(4-trifluoromethyl-phenyl)-benzoimidazol-1-yl]-acetylamino}-benzoic acid ethyl ester This compound was prepared in analogy to example 43, intermediate, from (2-amino-5-fluoro-phenyl)-carbamic acid tert-butyl ester, cyclohexanecarboxaldehyde, 4-(trifluoromethyl)benzoic acid and 4-isocyano-benzoic acid ethyl ester.

Light brown foam (21%). MS m/e (M+H)$^+$: 568.2.

Example 45

4-{2-[2-(4-Chloro-phenyl)-5,6-difluoro-benzoimidazol-1-yl]-2-cyclohexyl-acetylamino}-3-trifluoromethoxy-benzoic acid The title compound was synthesized in analogy to example 22 from 4-{2-[2-(4-chloro-phenyl)-5,6-difluoro-benzoimidazol-1-yl]-2-cyclohexyl-acetylamino}-3-trifluoromethoxy-benzoic acid methyl ester to give the desired compound as colorless solid (84%).

MS (TS) m/e (M−H)⁻: 608.0.

Intermediate

4-{2-[2-(4-Chloro-phenyl)-5,6-difluoro-benzoimidazol-1-yl]-2-cyclohexyl-acetylamino}-3-trifluoromethoxy-benzoic acid methyl ester This compound was synthesized in analogy to example 22, intermediate d, from [2-(4-chloro-phenyl)-5,6-difluoro-benzoimidazol-1-yl]-cyclohexyl-acetic acid (example 22, intermediate c), 4-amino-3-trifluoromethoxy-benzoic acid methyl ester and using pyridine as a base to afford the title compound as a colorless solid (85%).

MS (TS) m/e (M+H)⁺: 622.0.

Example 46

4-{2-[2-(4-Chloro-phenyl)-5-fluoro-benzoimidazol-1-yl]-2-cyclohexyl-acetylamino}-benzoic acid This compound was synthesized in analogy to example 22 from 4-{2-[2-(4-chloro-phenyl)-5-fluoro-benzoimidazol-1-yl]-2-cyclohexyl-acetylamino}-benzoic acid ethyl ester.

Colorless solid (86%).

MS (TS) m/e (M−H)⁻: 504.1.

Intermediate

4-{2-[2-(4-Chloro-phenyl)-5-fluoro-benzoimidazol-1-yl]-2-cyclohexyl-acetylamino}-benzoic acid ethyl ester This compound was synthesized in analogy to example 43, intermediate, from (2-amino-5-fluoro-phenyl)-carbamic acid tert-butyl ester, cyclohexanecarboxaldehyde, 4-chloro-benzoic acid and 4-isocyano-benzoic acid ethyl ester.

MS m/e (M+H)⁺: 534.1.

Example 47

4-{2-[2-(4-Chloro-phenyl)-5-fluoro-benzoimidazol-1-yl]-2-cyclohexyl-acetylamino}-3-fluoro-benzoic acid This compound was synthesized in analogy to example 22 from 4-{2-[2-(4-chloro-phenyl)-5-fluoro-benzoimidazol-1-yl]-2-cyclohexyl-acetylamino}-3-fluoro-benzoic acid methyl ester. Off-white solid (89%).

MS (TS) m/e (M−H)⁻: 522.2.

Intermediate

4-{2-[2-(4-Chloro-phenyl)-5-fluoro-benzoimidazol-1-yl]-2-cyclohexyl-acetylamino}-3-fluoro-benzoic acid methyl ester This compound was synthesized in analogy to example 43, intermediate, from (2-amino-5-fluoro-phenyl)-carbamic acid tert-butyl ester, cyclohexanecarboxaldehyde, 4-chloro-benzoic acid and 3-fluoro-4-isocyano-benzoic acid methyl ester.

Light brown foam (15%). MS m/e (M+H)⁺: 538.2.

Example 48

(4-{2-[2-(4-Chloro-phenyl)-5,6-difluoro-benzoimidazol-1-yl]-2-cyclohexyl-acetylamino}-phenyl)-acetic acid The title compound was synthesized in analogy to example 22 from (4-{2-[2-(4-chloro-phenyl)-5,6-difluoro-benzoimidazol-1-yl]-2-cyclohexyl-acetylamino}-phenyl)-acetic acid ethyl ester to afford the desired compound as colorless solid (95%).

MS (TS) m/e (M−H)⁻: 536.3.

Intermediate

(4-{2-[2-(4-Chloro-phenyl)-5,6-difluoro-benzoimidazol-1-yl]-2-cyclohexyl-acetylamino}-phenyl)-acetic acid ethyl ester This compound was synthesized in analogy to example 22, intermediate d, from [2-(4-chloro-phenyl)-5,6-difluoro-benzoimidazol-1-yl]-cyclohexyl-acetic acid (example 20, intermediate c), (4-amino-phenyl)-acetic acid ethyl ester and O-(7-azabenzotriazol-1-yl)-N,N,N',N'-tetramethyluronium hexafluorophosphate to give the desired compound as a yellow foam (82%).

MS m/e (M+H)⁺: 566.3.

Example 49

2-(4-{2-[2-(4-Chloro-phenyl)-5,6-difluoro-benzoimidazol-1-yl]-2-cyclohexyl-acetylamino}-3-fluoro-phenyl)-propionic acid The title compound was synthesized in analogy to example 22 from 2-(4-{2-[2-(4-chloro-phenyl)-5,6-difluoro-benzoimidazol-1-yl]-2-cyclohexyl-acetylamino}-3-fluoro-phenyl)-propionic acid ethyl ester.

Colorless solid (93%). MS (TS) m/e (M−H)⁻: 568.0.

Intermediate

2-(4-{2-[2-(4-Chloro-phenyl)-5,6-difluoro-benzoimidazol-1-yl]-2-cyclohexyl-acetylamino}-3-fluoro-phenyl)-propionic acid ethyl ester The title compound was synthesized in analogy to example 22, intermediate d, from [2-(4-chloro-phenyl)-5,6-difluoro-benzoimidazol-1-yl]-cyclohexyl-acetic acid (example 20, intermediate c), 2-(4-amino-3-fluoro-phenyl)-propionic acid and using 4-(dimethylamino)pyridine as a base.

Colorless foam (74%). MS m/e (M+H)⁺: 598.1.

Example 50

2-(4-{2-[2-(4-Chloro-phenyl)-5,6-difluoro-benzoimidazol-1-yl]-2-cyclohexyl-acetylamino}-3-fluoro-phenyl)-2-methyl-propionic acid The title compound was synthesized in analogy to example 22 from 2-(4-{2-[2-(4-chloro-phenyl)-5,6-difluoro-benzoimidazol-1-yl]-2-cyclohexyl-acetylamino}-3-fluoro-phenyl)-2-methyl-propionic acid methyl ester.

Colorless solid (88%). MS (TS) m/e (M−H)⁻: 582.0.

Intermediate 2-(4-{2-[2-(4-Chloro-phenyl)-5,6-difluoro-benzoimidazol-1-yl]-2-cyclohexyl-acetylamino}-3-fluoro-phenyl)-2-methyl-propionic acid methyl ester The title compound was synthesized in analogy to example 22, intermediate d, from [2-(4-chloro-phenyl)-5,6-difluoro-benzoimidazol-1-yl]-cyclohexyl-acetic acid (example 22, intermediate c), 2-(4-amino-3-fluoro-phenyl)-2-methyl-propionic acid methyl ester and using 4-(dimethylamino)pyridine as a base.

Colorless foam (54%). MS m/e (M+H)⁺: 598.2.

Example 51

3-(4-{2-[2-(4-Chloro-phenyl)-5,6-difluoro-benzoimidazol-1-yl]-2-cyclohexyl-acetylamino}-phenyl)-propionic acid The title compound was synthesized in analogy to example 22 from 3-(4-{2-[2-(4-chloro-phenyl)-5,6-difluoro-benzoimidazol-1-yl]-2-cyclohexyl-acetylamino}-phenyl)-propionic acid ethyl ester.

Colorless solid (78%). MS (TS) m/e (M+H)⁺: 552.1.

Intermediate 3-(4-{2-[2-(4-Chloro-phenyl)-5,6-difluoro-benzoimidazol-1-yl]-2-cyclohexyl-acetylamino}-phenyl)-propionic acid ethyl ester The title compound was synthesized in analogy to example 20, intermediate d, from [2-(4-chloro-phenyl)-5,6-difluoro-benzoimidazol-1-yl]-cyclohexyl-acetic acid (example 20, intermediate c), 3-(4-amino-phenyl)-propionic acid ethyl ester, O-(7-azabenzotriazol-1-yl)-N,N,N',N'-tetramethyluronium hexafluorophosphate and N-ethyldiisopropylamine.

Colorless solid (48%). MS (TS) m/e (M+H)⁺: 580.2.

Example 52

3-(4-{2-[2-(4-Chloro-phenyl)-5,6-difluoro-benzoimidazol-1-yl]-2-cyclohexyl-acetylamino}-3-fluoro-phenyl)-propionic acid The title compound was synthesized in analogy to example 22 from 3-(4-{2-[2-(4-chloro-phenyl)-5,6-difluoro-benzoimidazol-1-yl]-2-cyclohexyl-acetylamino}-3-fluoro-phenyl)-propionic acid methyl ester (intermediate a).

Colorless solid (80%). MS (TS) m/e (M−H)⁻: 568.1.

Intermediate 3-(4-{2-[2-(4-Chloro-phenyl)-5,6-difluoro-benzoimidazol-1-yl]-2-cyclohexyl-acetylamino}-3-fluoro-phenyl)-propionic acid methyl ester The title compound was synthesized in analogy to example 22, intermediate d, from [2-(4-chloro-phenyl)-5,6-difluoro-benzoimidazol-1-yl]-cyclohexyl-acetic acid (example 22, intermediate c), 3-(4-amino-3-fluoro-phenyl)-propionic acid methyl ester, O-(7-azabenzotriazol-1-yl)-N,N,N',N'-tetramethyluronium hexafluorophosphate and N-ethyldiisopropylamine.

Light brown foam (38%). MS m/e (M+H)⁺: 584.1.

Examples 53 and 54

The stereoisomers of example 52 were synthesized through acidic cleavage (formic acid/isopropanol (1/1 v/v), reflux, 17 h) of chiral tert-butyl ester of intermediates b1 and b2 as described below.

(−)-3-(4-{2-[2-(4-Chloro-phenyl)-5,6-difluoro-benzoimidazol-1-yl]-2-cyclohexyl-acetylamino}-3-fluoro-phenyl)-propionic acid Colorless solid. MS (TS) m/e (M−H)⁻: 568.1.

(+)-3-(4-{2-[2-(4-Chloro-phenyl)-5,6-difluoro-benzoimidazol-1-yl]-2-cyclohexyl-acetylamino}-3-fluoro-phenyl)-propionic acid Colorless solid. MS (TS) m/e (M−H)⁻: 568.1.

Intermediates a) 3-(4-{2-[2-(4-Chloro-phenyl)-5,6-difluoro-benzoimidazol-1-yl]-2-cyclohexyl-acetylamino}-3-fluoro-phenyl)-propionic acid tert-butyl ester The title compound was synthesized in analogy to example 22, intermediate d, from [2-(4-chloro-phenyl)-5,6-difluoro-benzoimidazol-1-yl]-cyclohexyl-acetic acid (example 20, intermediate c), 3-(4-amino-3-fluoro-phenyl)-propionic acid tert-butyl ester and using 4-(dimethylamino)pyridine as base. Light brown foam (78%).

MS m/e (M+H)⁺: 626.3.

The stereoisomers of above intermediate were obtained by chiral preparative HPLC (Chiralpak-AD column).

b1) (−)-3-(4-{2-[2-(4-Chloro-phenyl)-5,6-difluoro-benzoimidazol-1-yl]-2-cyclohexyl-acetylamino}-3-fluoro-phenyl)-propionic acid tert-butyl ester Colorless foam (30%). MS m/e (M+H)⁺: 626.2.

b2) (+)-3-(4-{2-[2-(4-Chloro-phenyl)-5,6-difluoro-benzoimidazol-1-yl]-2-cyclohexyl-acetylamino}-3-fluoro-phenyl)-propionic acid tert-butyl ester Colorless foam (35%). MS m/e (M+H)⁺: 626.3.

Example 55

(4-{2-[2-(4-Chloro-phenyl)-5,6-difluoro-benzoimidazol-1-yl]-2-cyclohexyl-acetylamino}-3-fluoro-phenoxy)-acetic acid To a solution of (4-{2-[2-(4-chloro-phenyl)-5,6-difluoro-benzoimidazol-1-yl]-2-cyclohexyl-acetylamino}-3-fluoro-phenoxy)-acetic acid tert-butyl ester (120 mg, 0.19 mmol) in dichloromethane (5 ml) was added trifluoroacetic acid (1.5 ml). After 2 h, the solvent was removed under reduced pressure. The resulting oil (78 mg, 71%) solidified upon standing in the refrigerator.

Light-brown solid. MS m/e (M−H)⁻: 570.2.

Intermediates a) (3-Fluoro-4-nitro-phenoxy)-acetic acid tert-butyl ester

To a solution of 3-fluoro-4-nitrophenol (1.57 g, 10 mmol) in N,N-dimethylformamide (10 ml) were added tert-butyl bromoacetate (1.95 g, 10 mmol) and potassium carbonate (1.38 g, 10 mmol). The mixture was stirred overnight at room temperature. The solvent was evaporated under reduced pressure and the residue purified by column chromatography on silica gel (50 g, dichloromethane eluant) to afford the product as a pale-yellow solid (2.22 g, 84%).

MS m/e (M+NH₄)⁺: 289.0.

b) (4-Amino-3-fluoro-phenoxy)-acetic acid tert-butyl ester

A solution of (3-fluoro-4-nitro-phenoxy)-acetic acid tert-butyl ester (2.14 g, 8 mmol) in ethanol (3 ml) was hydrogenated 5 h at room temperature and atmospheric pressure over 10% palladium on charcoal. The catalyst was removed by filtration, the solvent evaporated under reduced pressure and the residue purified by column chromatography on silica gel (1:0 to 1:1 heptane/ethyl acetate eluant) to afford the product as a brown oil (960 mg, 50%).

MS m/e (M+H)⁺: 242.2.

c) (4-{2-[2-(4-Chloro-phenyl)-5,6-difluoro-benzoimidazol-1-yl]-2-cyclohexyl-acetylamino}-3-fluoro-phenoxy)-acetic acid tert-butyl ester To a suspension of [2-(4-chloro-phenyl)-5,6-difluoro-benzoimidazol-1-yl]-cyclohexyl-acetic acid (ex. 22, intermediate a), 150 mg, 0.37 mmol) in dichloromethane (5 ml) were added pyridine (2.5 eq, 70 µl) and thionyl chloride (1.2 eq, 30 µl). The mixture was stirred 30 min. at room temperature. Pyridine (1.2 eq, 30 µl) and 4-amino-3-fluoro-phenoxy)-acetic acid tert-butyl ester (0.95 eq, 85 mg) were added. The mixture was diluted with dichloromethane, and the organic phase washed with 10% aqueous sodium bicarbonate solution, water and brine, dried over magnesium sulfate and the residue after evaporation purified by column chromatography on silica gel (1:0 to 3:2 heptane/ethyl acetate eluant) to afford the title compound as a light-brown foam (137 mg, 58%).

MS m/e (M+H)⁺: 628.4.

Example 56

2-(4-{2-[2-(4-Chloro-phenyl)-5,6-difluoro-benzoimidazol-1-yl]-2-cyclohexyl-acetylamino}-3-fluoro-phenoxy)-propionic acid This compound was prepared in analogy to example 22 from 2-(4-{2-[2-(4-chloro-phenyl)-5,6-difluoro-benzoimidazol-1-yl]-2-cyclohexyl-acetylamino}-3-fluoro-phenoxy)-propionic acid methyl ester to give the title compound as colorless solid (76%).

MS (TS) m/e (M−H)⁻: 584.1.

Intermediate 2-(4-{2-[2-(4-Chloro-phenyl)-5,6-difluoro-benzoimidazol-1-yl]-2-cyclohexyl-acetylamino}-3-fluoro-phenoxy)-propionic acid methyl ester This compound was prepared in analogy to example 57, intermediate, from [2-(4-chloro-phenyl)-5,6-difluoro-benzoimidazol-1-yl]-cyclohexyl-acetic acid and 2-(4-amino-3-fluoro-phenoxy)-propionic acid methyl ester.

Light yellow foam (48%). MS (TS) m/e (M+H)⁺: 600.2.

Example 57

2-(4-{2-[2-(4-Chloro-phenyl)-5,6-difluoro-benzoimidazol-1-yl]-2-cyclohexyl-acetylamino}-3-fluoro-phenoxy)-2-methyl-propionic acid This compound was prepared in analogy to example 22 from 2-(4-{2-[2-(4-chloro-phenyl)-5,6-difluoro-benzoimidazol-1-yl]-2-cyclohexyl-acetylamino}-3-fluoro-phenoxy)-2-methyl-propionic acid ethyl ester.

Colorless solid (78%). MS (TS) m/e (M−H)⁻: 598.1.

Examples 58 and 59

The title compounds were obtained by separation of the stereoisomers of 2-(4-{2-[2-(4-chloro-phenyl)-5,6-difluoro-benzoimidazol-1-yl]-2-cyclohexyl-acetylamino}-3-fluoro-phenoxy)-2-methyl-propionic acid by chiral preparative HPLC (Chiralpak-AD column).

(+)-2-(4-{2-[2-(4-Chloro-phenyl)-5,6-difluoro-benzoimidazol-1-yl]-2-cyclohexyl-acetylamino}-3-fluoro-phenoxy)-2-methyl-propionic acid Colorless solid (45%). MS (TS) m/e (M−H)⁻: 598.1.

(−)-2-(4-{2-[2-(4-Chloro-phenyl)-5,6-difluoro-benzoimidazol-1-yl]-2-cyclohexyl-acetylamino}-3-fluoro-phenoxy)-2-methyl-propionic acid Colorless solid (31%). MS (TS) m/e (M−H)⁻: 598.1.

Intermediate 2-(4-{2-[2-(4-Chloro-phenyl)-5,6-difluoro-benzoimidazol-1-yl]-2-cyclohexyl-acetylamino}-3-fluoro-phenoxy)-2-methyl-propionic acid ethyl ester To the solution of 0.2 g (0.49 mmol) [2-(4-chloro-phenyl)-5,6-difluoro-benzoimidazol-1-yl]-cyclohexyl-acetic acid (example 22, intermediate c)) in 3 ml N,N-dimethylformamide, 0.21 g (0.55 mmol) O-(7-azabenzotriazol-1-yl)-N,N,N',N'-tetramethyluronium hexafluorophosphate, 0.42 ml (0.32 g, 2.5 mmol) N-ethyldiisopropylamine and 0.13 g (0.54 mmol) 2-(4-amino-3-fluoro-phenoxy)-2-methyl-propionic acid ethyl ester were added. After 18 h the reaction mixture was poured on water and ethyl acetate, the phases were separated, the organic layer was washed twice with water followed by brine and dried over magnesium sulfate. After filtration the residue was purified by column chromatography on silica gel to give 0.12 g (40%) of the desired compound as light yellow foam.

MS (TS) m/e (M+H)⁺: 628.3.

Example 60

1-(4-{2-[2-(4-Chloro-phenyl)-5,6-difluoro-benzoimidazol-1-yl]-2-cyclohexyl-acetylamino}-3-fluoro-phenoxy)-cyclopropanecarboxylic acid This compound was prepared in analogy to example 22 from 1-(4-{2-[2-(4-chloro-phenyl)-5,6-difluoro-benzoimidazol-1-yl]-2-cyclohexyl-acetylamino}-3-fluoro-phenoxy)-cyclopropanecarboxylic acid methyl ester.
Colorless solid (97%). MS (TS) m/e (M−H)$^−$: 596.1.

Examples 61 and 62

The title compounds were obtained by separation of the stereoisomers of 1-(4-{2-[2-(4-Chloro-phenyl)-5,6-difluoro-benzoimidazol-1-yl]-2-cyclohexyl-acetylamino}-3-fluoro-phenoxy)-cyclopropanecarboxylic acid by chiral preparative HPLC (Chiralpak-AD column).

(+)-1-(4-{2-[2-(4-Chloro-phenyl)-5,6-difluoro-benzoimidazol-1-yl]-2-cyclohexyl-acetylamino}-3-fluoro-phenoxy)-cyclopropanecarboxylic acid Colorless solid (45%). MS (TS) m/e (M−H)$^−$: 596.2.

(+)-1-(4-{2-[2-(4-Chloro-phenyl)-5,6-difluoro-benzoimidazol-1-yl]-2-cyclohexyl-acetylamino}-3-fluoro-phenoxy)-cyclopropanecarboxylic acid Colorless solid (39%). MS (TS) m/e (M−H)$^−$: 596.3.

Intermediate 1-(4-{2-[2-(4-Chloro-phenyl)-5,6-difluoro-benzoimidazol-1-yl]-2-cyclohexyl-acetylamino}-3-fluoro-phenoxy)-cyclopropanecarboxylic acid methyl ester This compound was prepared in analogy to example 22, intermediate d, from [2-(4-chloro-phenyl)-5,6-difluoro-benzoimidazol-1-yl]-cyclohexyl-acetic acid, 1-(4-amino-3-fluoro-phenoxy)-cyclopropanecarboxylic acid methyl ester and using 4-(dimethylamino)pyridine as base.
Colorless foam (57%). MS (TS) m/e (M+H)$^+$: 612.2.

Example 63

2-[2-(4-Chloro-phenyl)-5,6-difluoro-benzoimidazol-1-yl]-2-cyclohexyl-N-trans-(4-hydroxy-cyclohexyl)-acetamide This compound was prepared in analogy to example 22, intermediate d, from [2-(4-chloro-phenyl)-5,6-difluoro-benzoimidazol-1-yl]-cyclohexyl-acetic acid, trans-4-aminocyclohexanol and using diisopropylethylamine as base.
Light brown foam (66%). MS (TS) m/e (M+H)$^+$: 502.2.

Examples 64 and 65

The title compounds were obtained by separation of the stereoisomers of 2-[2-(4-chloro-phenyl)-5,6-difluoro-benzoimidazol-1-yl]-2-cyclohexyl-N-trans-(4-hydroxy-cyclohexyl)-acetamide by chiral preparative HPLC (Chiralpak-AD column).

(−)-2-[2-(4-Chloro-phenyl)-5,6-difluoro-benzoimidazol-1-yl]-2-cyclohexyl-N-trans-(4-hydroxy-cyclohexyl)-acetamide Colorless foam (37%). MS (TS) m/e (M+H)$^+$: 502.2.

(+)-2-[2-(4-Chloro-phenyl)-5,6-difluoro-benzoimidazol-1-yl]-2-cyclohexyl-N-trans-(4-hydroxy-cyclohexyl)-acetamide Colorless foam (39%). MS (TS) m/e (M+H)$^+$: 502.2.

Example 66

6-{2-[2-(4-Chloro-phenyl)-5,6-difluoro-benzoimidazol-1-yl]-2-cyclohexyl-acetylamino}-nicotinic acid 6-{2-[2-(4-Chloro-phenyl)-5,6-difluoro-benzoimidazol-1-yl]-2-cyclohexyl-acetylamino}-nicotinic acid methyl ester (24 mg, 0.04 mmol) was dissolved in water (0.5 ml) and dioxane (0.5 ml). Lithium hydroxide monohydrate (9 eq, 17 mg) was added and the mixture stirred 3 h at room temperature. The dioxane was removed under reduced pressure and the residue acidified to pH2 with 3M aqueous hydrochloric acid. The precipitate was filtered to afford the title compound as a white solid (20 mg, 84%).
MS m/e (M+H)$^+$: 525.1.

Intermediate

6-{2-[2-(4-Chloro-phenyl)-5,6-difluoro-benzoimidazol-1-yl]-2-cyclohexyl-acetylamino}-nicotinic acid methyl ester The title compound was prepared according to Example 22, intermediate c), from [2-(4-chloro-phenyl)-5,6-difluoro-benzoimidazol-1-yl]-cyclohexyl-acetic acid and methyl 6-aminonicotinate.
Colorless solid (49%). MS m/e (M+H)$^+$: 539.2.

Examples 67 and 68

The title compounds were obtained by separation of the stereoisomers of 4-{2-[2-(4-chloro-phenyl)-5,6-difluoro-benzoimidazol-1-yl]-2-cyclohexyl-acetylamino}-3-cyano-benzoic acid (Ex. 37) by chiral preparative HPLC (Chiralpak-AD column).

(+)-4-{2-[2-(4-Chloro-phenyl)-5,6-difluoro-benzoimidazol-1-yl]-2-cyclohexyl-acetylamino}-3-cyano-benzoic acid Colorless solid. MS (TS) m/e (M−H)$^−$: 547.1.

(−)-4-{2-[2-(4-Chloro-phenyl)-5,6-difluoro-benzoimidazol-1-yl]-2-cyclohexyl-acetylamino}-3-cyano-benzoic acid Colorless solid. MS (TS) m/e (M−H)$^−$: 547.1.

Examples 69 and 70

The title compounds were obtained by separation of the stereoisomers of 4-{2-[2-(4-chloro-phenyl)-5,6-difluoro-benzoimidazol-1-yl]-2-cyclohexyl-acetylamino}-3-methoxy-benzoic acid (Ex. 41) by chiral preparative HPLC (Chiralpak-AD column).

(+)-4-{2-[2-(4-Chloro-phenyl)-5,6-difluoro-benzoimidazol-1-yl]-2-cyclohexyl-acetylamino}-3-methoxy-benzoic acid Light yellow solid. MS (TS) m/e (M+H)+: 554.2.

(−)-4-{2-[2-(4-Chloro-phenyl)-5,6-difluoro-benzoimidazol-1-yl]-2-cyclohexyl-acetylamino}-3-methoxy-benzoic acid Light yellow solid. MS (TS) m/e (M+H)+: 554.2.

Examples 71 and 72

The title compounds were obtained by separation of the stereoisomers of 4-{2-[2-(4-chloro-phenyl)-5,6-difluoro-benzoimidazol-1-yl]-2-cyclohexyl-acetylamino}-3-trifluoromethyl-benzoic acid (Ex. 42) by chiral preparative HPLC (Chiralpak-AD column).

(+)-4-{2-[2-(4-Chloro-phenyl)-5,6-difluoro-benzoimidazol-1-yl]-2-cyclohexyl-acetylamino}-3-trifluoromethyl-benzoic acid Colorless solid. MS (TS) m/e (M+H)+: 590.4.

(−)-4-{2-[2-(4-Chloro-phenyl)-5,6-difluoro-benzoimidazol-1-yl]-2-cyclohexyl-acetylamino}-3-trifluoromethyl-benzoic acid Colorless solid. MS (TS) m/e (M−H)−: 590.3.

Examples 73 and 74

The title compounds were obtained by separation of the stereoisomers of 4-{2-[2-(4-chloro-phenyl)-5,6-difluoro-benzoimidazol-1-yl]-2-cyclohexyl-acetylamino}-3-trifluoromethoxy-benzoic acid (Ex. 45) by chiral preparative HPLC (Chiralpak-AD column).

(+)-4-{2-[2-(4-Chloro-phenyl)-5,6-difluoro-benzoimidazol-1-yl]-2-cyclohexyl-acetylamino}-3-trifluoromethoxy-benzoic acid Colorless solid. MS (TS) m/e (M−H)−: 606.2.

(−)-4-{2-[2-(4-Chloro-phenyl)-5,6-difluoro-benzoimidazol-1-yl]-2-cyclohexyl-acetylamino}-3-trifluoromethoxy-benzoic acid Colorless solid. MS (TS) m/e (M−H)−: 606.3.

Examples 75 and 76

The title compounds were obtained by separation of the stereoisomers of 4-{2-[2-(4-chloro-phenyl)-5-fluoro-benzoimidazol-1-yl]-2-cyclohexyl-acetylamino}-3-fluoro-benzoic acid (Ex. 47) by chiral preparative HPLC (Chiralpak-AD column).

(−)-4-{2-[2-(4-Chloro-phenyl)-5-fluoro-benzoimidazol-1-yl]-2-cyclohexyl-acetylamino}-3-fluoro-benzoic acid Colorless solid. MS (TS) m/e (M−H)−: 522.2.

(+)-4-{2-[2-(4-Chloro-phenyl)-5-fluoro-benzoimidazol-1-yl]-2-cyclohexyl-acetylamino}-3-fluoro-benzoic acid Colorless solid. MS (TS) m/e (M−H)−: 522.2.

Example 77

4-{2-[2-(4-Chloro-phenyl)-5,6-difluoro-benzoimidazol-1-yl]-2-cyclohexyl-acetylamino}-3-cyano-5-fluoro-benzoic acid This compound was prepared in analogy to example 22 from 4-{2-[2-(4-Chloro-phenyl)-5,6-difluoro-benzoimidazol-1-yl]-2-cyclohexyl-acetylamino}-3-cyano-5-fluoro-benzoic acid methyl ester to give the title compound as a colorless solid (96%).

MS (TS) m/e (M−H)−: 565.2.

Intermediate

4-{2-[2-(4-Chloro-phenyl)-5,6-difluoro-benzoimidazol-1-yl]-2-cyclohexyl-acetylamino}-3-cyano-5-fluoro-benzoic acid methyl ester The title compound was prepared in analogy to example 22, intermediate d), from [2-(4-chloro-phenyl)-5,6-difluoro-benzoimidazol-1-yl]-cyclohexyl-acetic acid and 4-amino-3-cyano-5-fluoro-benzoic acid methyl ester (Arzneimittel Forschung, 34(II), Nr. 11a, 1984; 1612-1624) to give the product as a light brown solid (20%).

MS (TS) m/e (M+H)+: 581.1.

Examples 78 and 79

The title compounds were obtained by separation of the stereoisomers of 4-{2-[2-(4-chloro-phenyl)-5,6-difluoro-benzoimidazol-1-yl]-2-cyclohexyl-acetylamino}-3-cyano-5-fluoro-benzoic acid by chiral preparative HPLC (Reprosil Chiral-NR column).

(+)-4-{2-[2-(4-Chloro-phenyl)-5,6-difluoro-benzoimidazol-1-yl]-2-cyclohexyl-acetylamino}-3-cyano-5-fluoro-benzoic acid Light brown foam. MS (TS) m/e (M−H)−: 565.2.

(−)-4-{2-[2-(4-Chloro-phenyl)-5,6-difluoro-benzoimidazol-1-yl]-2-cyclohexyl-acetylamino}-3-cyano-5-fluoro-benzoic acid Light brown foam. MS (TS) m/e (M−H)−: 565.2.

Example 80

1-(4-{2-[2-(4-Chloro-phenyl)-benzoimidazol-1-yl]-2-cyclohexyl-acetylamino}-3-fluoro-phenoxy)-cyclopropanecarboxylic acid This compound was prepared in analogy to example 22 from 1-(4-{2-[2-(4-chloro-phenyl)-benzoimidazol-1-yl]-2-cyclohexyl-acetylamino}-3-fluoro-phenoxy)-cyclopropanecarboxylic acid methyl ester to give the title compound as a light yellow solid (91%).

MS (TS) m/e (M−H)−: 560.1.

Intermediates a) 1-(4-{2-[2-(4-Chloro-phenyl)-benzoimidazol-1-yl]-2-cyclohexyl-acetylamino}-3-fluoro-phenoxy)-cyclopropanecarboxylic acid methyl ester The title compound was prepared in analogy to example 22, intermediate d), from [2-(4-chloro-phenyl)-benzoimidazol-1-yl]-cyclohexyl-acetic acid (Ex. 39/40, int. b) and 1-(4-amino-3-fluoro-phenoxy)-cyclopropanecarboxylic acid methyl ester to give the product as a light yellow foam (21%).
MS (TS) m/e (M+H)$^+$: 576.2.

b) 1-(4-Amino-3-fluoro-phenoxy)-cyclopropanecarboxylic acid methyl ester

To a solution of 4.49 g (17.6 mmol) 1-(3-fluoro-4-nitro-phenoxy)-cyclopropanecarboxylic acid methyl ester in 50 mL ethanol 0.5 g 10% palladium on charcoal was added and the suspension stirred for 8 h at room temperature under an atmosphere of hydrogen (1.7 bar). After the addition of 100 mL ethyl acetate the catalyst was filtered off, the filtrate evaporated and dried under high vacuum to give the title compound as a brown oil (98%) which was used in the next step without further purification.
MS (TS) m/e (M+H)$^+$: 226.1.

c) 1-(3-Fluoro-4-nitro-phenoxy)-cyclopropanecarboxylic acid methyl ester

The solution of 7.5 g (22.3 mmol) 4-bromo-2-(3-fluoro-4-nitro-phenoxy)-butyric acid methyl ester in 100 mL tetrahydrofuran was cooled to −15° C. and 2.63 g (23.4 mmol) potassium tert-butoxide were added. The cooling bath was removed and the reaction was stirred for 5 h at room temperature. The dark solution was poured 200 mL ethyl acetate and 200 mL aqueous hydrochloric acid, extracted and the phases were separated. The organic layer was washed with brine and the aqueous layers extracted with ethyl acetate. The combined organic layers were dried over magnesium sulfate, filtered and evaporated. The residue was purified by column chromatography on silica gel using an MPLC system (CombiFlash Companion, Isco Inc.) eluting with a gradient of heptane:ethyl acetate (100:30 to 70:30 v/v) to afford the title compound as a light yellow oil (79%).
MS (TS) m/e (M): 255.0.

d) 4-Bromo-2-(3-fluoro-4-nitro-phenoxy)-butyric acid methyl ester

To the solution of 5.5 g (35.0 mmol) 3-fluoro-4-nitrophenol in 55 mL N,N-dimethylformamide, 11.8 g (45.5 mmol) methyl 2,4-dibromobutyrate and 6.3 g (45.5 mmol) potassium carbonate were added. After stirring for 3 h the reaction mixture was poured on ethyl acetate and 1 M aqueous hydrochloric acid and extracted. The organic phases were washed with brine, dried over magnesium sulfate, filtered and evaporated. The residue was purified by column chromatography on silica gel using an MPLC system (CombiFlash Companion, Isco Inc.) eluting with a gradient of heptane:ethyl acetate (1:0 to 1:1 v/v) to afford the title compound as a light yellow oil (64%) which was pure enough to be used in the next step.

Examples 81 and 82

The title compounds were obtained by separation of the stereoisomers of 1-(4-{2-[2-(4-chloro-phenyl)-benzoimidazol-1-yl]-2-cyclohexyl-acetylamino}-3-fluoro-phenoxy)-cyclopropanecarboxylic acid by chiral preparative HPLC (Chiralpak-AD column).

(+)-1-(4-{2-[2-(4-Chloro-phenyl)-benzoimidazol-1-yl]-2-cyclohexyl-acetylamino}-3-fluoro-phenoxy)-cyclopropanecarboxylic acid Colorless solid. MS (TS) m/e (M+H)$^+$: 562.4.

(−)-1-(4-{2-[2-(4-Chloro-phenyl)-benzoimidazol-1-yl]-2-cyclohexyl-acetylamino}-3-fluoro-phenoxy)-cyclopropanecarboxylic acid Colorless solid. MS (TS) m/e (M−H)$^−$: 560.2

Example 83

4-{2-[2-(4-Chloro-phenyl)-benzoimidazol-1-yl]-2-cyclohexyl-acetylamino}-3-trifluoromethyl-benzoic acid This compound was prepared in analogy to example 22 from 4-{2-[2-(4-chloro-phenyl)-benzoimidazol-1-yl]-2-cyclohexyl-acetylamino}-3-trifluoromethyl-benzoic acid methyl ester to give the title compound as a colorless solid (79%).
MS (TS) m/e (M+H)$^+$: 556.

Intermediates a) 4-{2-[2-(4-Chloro-phenyl)-benzoimidazol-1-yl]-2-cyclohexyl-acetylamino}-3-trifluoromethyl-benzoic acid methyl ester The title compound was prepared in analogy to example 22, intermediate d), from [2-(4-chloro-phenyl)-benzoimidazol-1-yl]-cyclohexyl-acetic acid (Ex. 39/40, int. b) and 4-amino-3-trifluoromethyl-benzoic acid methyl ester to give the product as a light yellow solid (57%).
MS (TS) m/e (M+H)$^+$: 570.3.

b) 4-Amino-3-trifluoromethyl-benzoic acid methyl ester

To a solution of 4.0 g (16.1 mmol) 4-nitro-3-trifluoromethyl-benzoic acid methyl ester in 50 mL methanol 0.4 g 10% palladium on charcoal was added and the suspension stirred for 2 h at room temperature under an atmosphere of hydrogen (1.7 bar). After the addition of 100 mL ethyl acetate the catalyst was filtered off, the filtrate evaporated and dried under high vacuum to give the title compound as a white solid (98%) which was used in the next step without further purification.

c) 4-Nitro-3-trifluoromethyl-benzoic acid methyl ester

The solution of 4.2 g (17.9 mmol) 4-nitro-3-(trifluoromethyl)benzoic acid (commercially available) in 5.1 mL 1.25 M hydrochloric acid in methanol was refluxed for 5 h. After cooling down to room temperature the solution was poured on saturated aqueous sodium bicarbonate solution and the phases were separated. The aqueous layer was extracted three times with ethyl acetate, the combined organic layers washed with brine, dried over magnesium sulfate and evaporated. After filtration the solvent was evaporated and the residue was purified by column chromatography on silica gel using an MPLC system (CombiFlash Companion, Isco Inc.) eluting with a gradient of heptane:ethyl acetate (100:0 to 60:40 v/v) to afford the title compound as a light yellow solid (90%) which was pure enough for the next step without further purification.

Examples 84 and 85

The title compounds were obtained by separation of the stereoisomers of 4-{2-[2-(4-chloro-phenyl)-benzoimidazol-1-yl]-2-cyclohexyl-acetylamino}-3-trifluoromethyl-benzoic acid by chiral preparative HPLC (Chiralpak-AD column).

(+)-4-{2-[2-(4-Chloro-phenyl)-benzoimidazol-1-yl]-2-cyclohexyl-acetylamino}-3-trifluoromethyl-benzoic acid Colorless solid. MS (TS) m/e (M−H)⁻: 554.0.

(−)-4-{2-[2-(4-Chloro-phenyl)-benzoimidazol-1-yl]-2-cyclohexyl-acetylamino}-3-trifluoromethyl-benzoic acid Colorless solid. MS (TS) m/e (M+H)⁺: 554.0.

Example 86 trans-4-{2-Cyclohexyl-2-[5,6-difluoro-2-(6-methoxy-pyridin-3-yl)-benzoimidazol-1-yl]-acetylamino}-cyclohexanecarboxylic acid The title compound was prepared in analogy to example 7 followed by purification with preparative HPLC on reversed phase eluting with a gradient of acetonitrile/water. MS (ES⁺): 527 (M+H)⁺.

Example 87

(−)-trans-4-{2-[2-(6-Chloro-pyridin-3-yl)-5,6-difluoro-benzoimidazol-1-yl]-2-cyclohexyl-acetylamino}-cyclohexanecarboxylic acid The title compound was prepared in accordance with example 7 conducting separation of the stereoisomers by chiral preparative HPLC (Chiralpak AD column) eluting with a gradient of ethanol (+0.5% formic acetic acid)/heptane. MS (ES⁺): 531 (M+H)⁺.

Intermediate (trans-4-Isocyano-cyclohexyl)-acetic acid ethyl ester 5 g (22.8 mmol) of trans-(4-Amino-cyclohexyl)-acetic acid ethyl ester hydrochloride were suspended in a mixture of 40 ml (731 mmol) ethylformiate and 10 ml DMF. 5.6 ml (25 mmol) of DIPEA were added and the mixture was heated to 80° C. for 72 h. The solvent mixture was evaporated to dryness and the crude product extracted from ethyl acetate/water. 4.2 g of a yellow solid were obtained which were dissolved in 40 ml DCM. 6.6 ml (47 mmol) triethylamine were added and the mixture was cooled to 0-5° C. 2.3 ml (7.9 mmol) of triphosgene were dissolved in 10 ml DCM and added dropwise. The reaction mixture was warmed to room temperature and the product was isolated directly via silica gel chromatography using ethyl acetate/hexane as an eluant. The intermediate was used without further characterization.

Example 88

(trans-4-{2-[2-(6-Chloro-2-methoxy-pyridin-3-yl)-5,6-difluoro-benzoimidazol-1-yl]-2-cyclohexyl-acetylamino}-cyclohexyl)-acetic acid The title compound was prepared in analogy to example 7 using (trans-4-isocyano-cyclohexyl)-acetic acid ethyl ester as the isonitrile component followed by purification with preparative HPLC on reversed phase eluting with a gradient of acetonitrile/water. MS (ES⁺): 575 (M+H)⁺.

Example 89 trans-4-{2-[2-(6-Chloro-2-methoxy-pyridin-3-yl)-5,6-difluoro-benzoimidazol-1-yl]-2-cyclohexyl-acetylamino}-cyclohexanecarboxylic acid The title compound was prepared in analogy to example 7 followed by purification with preparative HPLC on reversed phase eluting with a gradient of acetonitrile/water. MS (ES⁺): 561 (M+H)⁺.

Example 90

4-{2-[2-(6-Chloro-2-methoxy-pyridin-3-yl)-5,6-difluoro-benzoimidazol-1-yl]-2-cyclohexyl-acetylamino}-benzoic acid The title compound was prepared in analogy to example 7 followed by purification with preparative HPLC on reversed phase eluting with a gradient of acetonitrile/water. MS (ES⁺): 555 (M+H)⁺.

Example 91

(+)-trans-4-{2-Cyclohexyl-2-[5,6-difluoro-2-(6-methoxy-pyridin-3-yl)-benzoimidazol-1-yl]-acetylamino}-cyclohexanecarboxylic acid The title compound was prepared in accordance with example 7 conducting separation of the stereoisomers by chiral preparative HPLC (Chiralpak-AD column) eluting with a gradient of ethanol (+0.5% formic acetic acid)/heptane. MS (ES⁺): 528 (M+H)⁺.

Example 92

(−)-trans-4-{2-[2-(6-Chloro-2-methoxy-pyridin-3-yl)-5,6-difluoro-benzoimidazol-1-yl]-2-cyclohexyl-acetylamino}-cyclohexanecarboxylic acid The title compound was prepared in accordance with example 7 conducting separation of the stereoisomers by chiral preparative HPLC (Chiralpak AD column) eluting with a gradient of ethanol (+0.5% formic acetic acid)/heptane. MS (ES⁺): 561 (M+H)⁺.

Example 93

(−)-(trans-4-{2-[2-(6-Chloro-2-methoxy-pyridin-3-yl)-5,6-difluoro-benzoimidazol-1-yl]-2-cyclohexyl-acetylamino}-cyclohexyl)-acetic acid The title compound was prepared in accordance with example 7 conducting separation of the stereoisomers by chiral preparative HPLC (Chiralpak AD column) eluting with a gradient of ethanol (+0.5% formic acetic acid)/heptane. MS (ES$^+$): 575 (M+H)$^+$.

Example 94

(+)-4-{(S)-2-[2-(6-Chloro-2-methoxy-pyridin-3-yl)-5,6-difluoro-benzoimidazol-1-yl]-2-cyclohexyl-acetylamino}-benzoic acid The title compound was prepared in accordance with example 7 conducting separation of the stereoisomers by chiral preparative HPLC (Chiralcel-OD column) eluting with a gradient of ethanol (+0.5% formic acetic acid)/heptane. MS (ES$^+$): 555 (M+H)$^+$.

Intermediate

Bicyclo[2.2.1]heptane-7-carbaldehyde 15.9 g (81 mmol) of 7-Bromo-bicyclo[2.2.1]heptane were added dropwise to 2 g magnesium (81 mmol) in 25 ml of diethyl ether and refluxed for 2.5 h. The mixture was cooled to 0-5° C. and 6.3 ml (81 mmol) of DMF were added dropwise. The mixture was then refluxed for 2 h, cooled to room temperature and the white solid filtered off and washed with ether. The filtrate was reduced and 4.87 g of a white solid were obtained. The intermediate was used without further characterization.

Example 95

4-{2-Bicyclo[2.2.1]hept-7-yl-2-[2-(4-chloro-phenyl)-5,6-difluoro-benzoimidazol-1-yl]-acetylamino}-benzoic acid The title compound was prepared in analogy to example 7 followed by purification with preparative HPLC on reversed phase eluting with a gradient of acetonitrile/water. MS (ES$^+$): 536 (M+H)$^+$.

Example 96

(trans-4-{2-Cyclohexyl-2-[5,6-difluoro-2-(2-methoxy-pyridin-3-yl)-benzoimidazol-1-yl]-acetylamino}-cyclohexyl)-acetic acid The title compound was prepared in analogy to example 7 followed by purification with preparative HPLC on reversed phase eluting with a gradient of acetonitrile/water. MS (ES$^+$): 541 (M+H)$^+$.

Example 97

4-[2-Cyclohexyl-2-(5,6-difluoro-2-p-tolyl-benzoimidazol-1-yl)-acetylamino]-benzoic acid The title compound was prepared in analogy to example 7 followed by purification with preparative HPLC on reversed phase eluting with a gradient of acetonitrile/water. MS (ES$^+$): 504 (M+H)$^+$.

Example 98 trans-4-[2-Cyclohexyl-2-(5,6-difluoro-2-p-tolyl-benzoimidazol-1-yl)-acetylamino]-cyclohexanecarboxylic acid The title compound was prepared in analogy to example 7 followed by purification with preparative HPLC on reversed phase eluting with a gradient of acetonitrile/water. MS (ES$^+$): 510 (M+H)$^+$.

Example 99

(−)-4-[2-Cyclohexyl-2-(5,6-difluoro-2-p-tolyl-benzoimidazol-1-yl)-acetylamino]-benzoic acid The title compound was prepared in accordance with example 7 conducting separation of the stereoisomers by chiral preparative HPLC (Reprosil Chiral NR column) eluting with a gradient of ethanol (+0.5% formic acetic acid)/heptane. MS (ES$^+$): 504 (M+H)$^+$.

Example 100

(+)-trans-[2-Cyclohexyl-2-(5,6-difluoro-2-p-tolyl-benzoimidazol-1-yl)-acetylamino]-cyclohexanecarboxylic acid The title compound was prepared in accordance with example 7 conducting separation of the stereoisomers by chiral preparative HPLC (Reprosil Chiral NR column) eluting with a gradient of ethanol (+0.5% formic acetic acid)/heptane. MS (ES$^+$): 510 (M+H)$^+$.

Example 101 trans-4-{2-Bicyclo[2.2.1]hept-7-yl-2-[2-(4-chloro-phenyl)-5,6-difluoro-benzoimidazol-1-yl]-acetylamino}-cyclohexanecarboxylic acid The title compound was prepared in analogy to example 7 followed by purification with preparative HPLC on reversed phase eluting with a gradient of acetonitrile/water. MS (ES$^+$): 542 (M+H)$^+$.

Example 102

4-{2-Cyclohexyl-2-[5,6-difluoro-2-(4-methoxy-phenyl)-benzoimidazol-1-yl]-acetylamino}-benzoic acid The title compound was prepared in analogy to example 7 followed by purification with preparative HPLC on reversed phase eluting with a gradient of acetonitrile/water. MS (ES$^+$): 520 (M+H)$^+$.

Example 103

(−)-trans-4-{2-Bicyclo[2.2.1]hept-7-yl-2-[2-(4-chloro-phenyl)-5,6-difluoro-benzoimidazol-1-yl]-acetylamino}-cyclohexanecarboxylic acid The title compound was prepared in accordance with example 7 conducting separation of the stereoisomers by chiral preparative HPLC (Reprosil Chiral NR column) eluting with a gradient of ethanol (+0.5% trifluoroacetic acid)/heptane. MS (ES$^+$): 542 (M+H)$^+$.

Example 104 trans-4-{2-Cyclohexyl-2-[5,6-difluoro-2-(4-methoxy-phenyl)-benzoimidazol-1-yl]-acetylamino}-cyclohexanecarboxylic acid The title compound was prepared in accordance with example 7 conducting separation of the stereoisomers by chiral preparative HPLC (Reprosil Chiral NR column) eluting with a gradient of ethanol (+0.5% trifluoroacetic acid)/heptane. MS (ES$^+$): 526 (M+H)$^+$.

Example 105

(−)-4-{2-Cyclohexyl-2-[5,6-difluoro-2-(4-methoxy-phenyl)-benzoimidazol-1-yl]-acetylamino}-benzoic acid The title compound was prepared in accordance with example 7 conducting separation of the stereoisomers by chiral preparative HPLC (Chiralpak-AD column) eluting with a gradient of ethanol (+0.5% formic acetic acid)/heptane. MS (ES$^-$): 518 (M−H)$^-$.

Example 106

(trans-4-{2-Bicyclo[2.2.1]hept-7-yl-2-[2-(4-chloro-phenyl)-5,6-difluoro-benzoimidazol-1-yl]-acetylamino}-cyclohexyl)-acetic acid The title compound was prepared in analogy to example 7 followed by purification with preparative HPLC on reversed phase eluting with a gradient of acetonitrile/water. MS (ES$^+$): 556 (M+H)$^+$.

Example 107

(−)-4-{2-Bicyclo[2.2.1]hept-7-yl-2-[2-(4-chloro-phenyl)-5,6-difluoro-benzoimidazol-1-yl]-acetylamino}-benzoic acid The title compound was prepared in accordance with example 7 conducting separation of the stereoisomers by chiral preparative HPLC (Reprosil Chiral NR column) eluting with a gradient of ethanol (+0.5% formic acetic acid)/heptane. MS (ES$^+$): 536 (M+H)$^+$.

Example 108

(−)-(trans-4-{2-Bicyclo[2.2.1]hept-7-yl-2-[2-(4-chloro-phenyl)-5,6-difluoro-benzoimidazol-1-yl]-acetylamino}-cyclohexyl)-acetic acid The title compound was prepared in accordance with example 7 conducting separation of the stereoisomers by chiral preparative HPLC (Chiralpak AD column) eluting with a gradient of ethanol (+0.5% formic acetic acid)/heptane. MS (ES$^+$): 556 (M+H)$^+$.

Example 109

2-[2-(4-Chloro-phenyl)-5,6-difluoro-benzoimidazol-1-yl]-2-cyclohexyl-N-[4-(1H-tetrazol-5-yl)-phenyl]-acetamide The suspension of 0.13 g (0.25 mmol) 2-[2-(4-chloro-phenyl)-5,6-difluoro-benzoimidazol-1-yl]-N-(4-cyano-phenyl)-2-cyclohexyl-acetamide, 0.17 g (1.26 mmol) triethylammonium hydrochloride and 82 mg (1.26 mmol) sodium azide in 3 mL ortho-xylene was stirred at 145° C. for 2.5 hrs. The brown suspension was poured on 1M aqueous hydrochloric acid solution and extracted three times with ethyl acetate. The combined organic layers were dried over magnesium sulfate, filtered and evaporated to dryness. The residue was dissolved in acetonitrile and a few drops of water were added upon which precipitation started. The formed suspension was filtered and the solid was washed with acetonitrile containing a few drops of water to give the desired compound as a white solid (68%). MS (ES$^+$): 548.3 (M+H).

Intermediate

2-[2-(4-Chloro-phenyl)-5,6-difluoro-benzoimidazol-1-yl]-N-(4-cyano-phenyl)-2-cyclohexyl-acetamide To the suspension of 0.5 g (1.24 mmol) [2-(4-chloro-phenyl)-5,6-difluoro-benzoimidazol-1-yl]-cyclohexyl-acetic acid (Ex. 22, int. c) in 3 ml dichloromethane 0.01 ml (0.12 mmol) N,N-dimethylformamide, 0.13 ml (1.54 mmol) oxalylchloride were added dropwise under gas evolution. The resulting clear, light yellow solution was stirred for 1 h at room temperature, then evaporated to dryness, treated twice with 5 ml of dichloromethane and again evaporated to dryness. The light yellow solid was dissolved in 8 ml of dichloromethane and added dropwise to a stirred mixture of 0.13 g (1.24 mmol) 4-aminobenzonitrile and 0.46 ml (3.31 mmol) triethylamine in dichloromethane. After stirring for 3.75 h the clear yellow solution was poured on water and extracted twice with dichloromethane. The organic layers were washed with water and brine, dried over magnesium sulfate, filtered and after addition of silica gel evaporated to dryness. Purification by silica gel column chromatography using a MPLC system (CombiFlash Companion, Isco Inc.) eluting with a gradient of heptane to heptan/ethyl acetate (1:0 to 1:1 v/v) yielded 0.45 g (81%) of the title compound as a light brown solid. MS (ES$^-$): M−H: 571.2.

Example 110

2-[2-(4-Chloro-phenyl)-5,6-difluoro-benzoimidazol-1-yl]-N-[2-chloro-4-(1H-tetrazol-5-yl)-phenyl]-2-cyclohexyl-acetamide The title compound was formed in analogy to Example 109 from N-(2-chloro-4-cyano-phenyl)-2-[2-(4-chloro-phenyl)-5,6-difluoro-benzoimidazol-1-yl]-2-cyclohexyl-acetamide without using water for the precipitation to give the desired compound as a white solid (85%).

MS (ES$^-$): 580.1 (M−H).

Intermediate

N-(2-Chloro-4-cyano-phenyl)-2-[2-(4-chloro-phenyl)-5,6-difluoro-benzoimidazol-1-yl]-2-cyclohexyl-acetamide The title compound was prepared in analogy to example 22, int. d) from [2-(4-chloro-phenyl)-5,6-difluoro-benzoimidazol-1-yl]-cyclohexyl-acetic acid and 4-amino-3-chlorobenzonitrile to give the desired compound as a white solid (62%). MS (ES$^+$): M−H: 539.2.

Example 111

2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide The title compound was formed in analogy to Example 109 from 2-[2-(4-chloro-phenyl)-5,6-difluoro-benzoimidazol-1-yl]-N-(4-cyano-2-fluoro-phenyl)-2-cyclohexyl-acetamide without using water for the precipitation. The residue was suspended in acetonitrile and heated to reflux temperature upon which a solution formed. After cooling to room temperature the newly formed precipitate was collected by filtration and the same procedure was applied a second time to give the desired compound as an off-white solid (29%). MS (ES+): 566.4 (M+H).

Intermediate

2-[2-(4-Chloro-phenyl)-5,6-difluoro-benzoimidazol-1-yl]-N-(4-cyano-2-fluoro-phenyl)-2-cyclohexyl-acetamide The title compound was prepared in analogy to example 22, int. d) from [2-(4-chloro-phenyl)-5,6-difluoro-benzoimidazol-1-yl]-cyclohexyl-acetic acid and 4-amino-3-fluorobenzonitrile and using a gradient of heptane:ethyl acetate (1:1 to 4:1) as eluant. The title product was crystallized from tert-butyl methyl ether to give 0.79 g (61%) of a white solid (29%).
MS (ES+): M+H: 523.2.

Examples 112 and 113

The title compounds were obtained by separation of the stereoisomers of 2-[2-(4-chloro-phenyl)-5,6-difluoro-benzoimidazol-1-yl]-2-cyclohexyl-N-[2-fluoro-4-(1H-tetrazol-5-yl)-phenyl]-acetamide by chiral preparative HPLC (Reprosil Chiral-NR column).

(+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide Colorless solid. MS (TS) m/e (M+H)+: 566.4

(+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide Colorless solid. MS (TS) m/e (M+H)+: 566.4

Example 114

2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide The title compound was formed in analogy to Example 109 from 2-[2-(4-chloro-phenyl)-5,6-difluoro-benzoimidazol-1-yl]-N-(4-cyano-2-trifluoromethyl-phenyl)-2-cyclohexyl-acetamide without using water for the precipitation. Colorless solid (87%). MS (TS) m/e (M+H)+: 616.3.

Intermediate

2-[2-(4-Chloro-phenyl)-5,6-difluoro-benzoimidazol-1-yl]-N-(4-cyano-2-trifluoromethyl-phenyl)-2-cyclohexyl-acetamide The title compound was prepared in analogy to example 22, int. d) from [2-(4-chloro-phenyl)-5,6-difluoro-benzoimidazol-1-yl]-cyclohexyl-acetic acid and 4-amino-3-trifluoromethylbenzonitrile. The compound was purified by using a MPLC system (CombiFlash Companion, Isco Inc.) eluting with a gradient of heptane to n-heptane/ethyl acetate (1:0 to 4:1 v/v) and subsequent purification by preparative HPLC using a Gemini column and a gradient of acetonitrile:water (containing 0.5% formic acid). Colorless foam (47%). MS (ES+): M+H: 573.2.

Examples 115 and 116

The title compounds were obtained by separation of the stereoisomers of 2-[2-(4-chloro-phenyl)-5,6-difluoro-benzoimidazol-1-yl]-2-cyclohexyl-N-[4-(1H-tetrazol-5-yl)-2-trifluoromethyl-phenyl]-acetamide by chiral preparative HPLC (Reprosil Chiral-NR column) using a mixture of ethanol (containing 0.01 M ammonium acetate):n-heptane (30:70 v/v).

(+)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide Colorless solid. MS (TS) m/e (M+H)+: 616.4

(−)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide Colorless solid. MS (TS) m/e (M+H)+: 616.4

Example 117

2-[2-(4-Chloro-phenyl)-benzoimidazol-1-yl]-2-cyclohexyl-N-[4-(1H-tetrazol-5-yl)-2-trifluoromethyl-phenyl]-acetamide The title compound was formed in analogy to Example 109 from 2-[2-(4-chloro-phenyl)-benzoimidazol-1-yl]-N-(4-cyano-2-trifluoromethyl-phenyl)-2-cyclohexyl-acetamide without using water for the precipitation. Colorless solid (89%). MS (TS) m/e (M+H)+: 580.2.

Intermediate

2-[2-(4-Chloro-phenyl)-benzoimidazol-1-yl]-N-(4-cyano-2-trifluoromethyl-phenyl)-2-cyclohexyl-acetamide The title compound was prepared in analogy to example 22, int. d) from [2-(4-chloro-phenyl)-5,6-difluoro-benzoimidazol-1-yl]-cyclohexyl-acetic acid and 4-amino-3-trifluoromethylbenzonitrile. The compound was purified by preparative HPLC using a Gemini column and a gradient of acetonitrile:water (containing 0.5% formic acid). Light brown foam (42%). MS (ES+): M+H: 537.3.

Examples 118 and 119

The title compounds were obtained by separation of the stereoisomers of 2-[2-(4-chloro-phenyl)-5,6-difluoro-benzoimidazol-1-yl]-2-cyclohexyl-N-[4-(1H-tetrazol-5-yl)-2-trifluoromethyl-phenyl]-acetamide by chiral preparative HPLC (Reprosil Chiral-NR column) using a mixture of ethanol (containing 0.01 M ammonium acetate):n-heptane (40:60 v/v).

(+)-2-[2-(4-Chloro-phenyl)-benzoimidazol-1-yl]-2-cyclohexyl-N-[4-(1H-tetrazol-5-yl)-2-trifluoromethyl-phenyl]-acetamide Colorless solid. MS (TS) m/e (M+H)$^+$: 580.3

(−)-2-[2-(4-Chloro-phenyl)-benzoimidazol-1-yl]-2-cyclohexyl-N-[4-(1H-tetrazol-5-yl)-2-trifluoromethyl-phenyl]-acetamide Off-white solid. MS (TS) m/e (M+H)$^+$: 580.2

Example 120

2-Cyclohexyl-2-[2-(2,6-dimethoxy-pyridin-3-yl)-5,6-difluoro-benzoimidazol-1-yl]-N-[2-fluoro-4-(1H-tetrazol-5-yl)-phenyl]-acetamide The title compound was formed in analogy to Example 109 from N-(4-cyano-2-fluoro-phenyl)-2-cyclohexyl-2-[2-(2,6-dimethoxy-pyridin-3-yl)-5,6-difluoro-benzoimidazol-1-yl]-acetamide. The crude product was purified on a preparative HPLC system (Phenomenex Gemini column) using a gradient of acetonitrile and water (containing 0.5% formic acid). Off-white solid (44%). MS (TS) m/e (M−H)$^-$: 591.4.

Example 121

2-Cyclohexyl-2-[2-(2,6-dimethoxy-pyridin-3-yl)-5,6-difluoro-benzoimidazol-1-yl]-N-[4-(1H-tetrazol-5-yl)-2-trifluoromethyl-phenyl]-acetamide The title compound was formed in analogy to Example 109 from N-(4-cyano-2-trifluoromethyl-phenyl)-2-cyclohexyl-2-[2-(2,6-dimethoxy-pyridin-3-yl)-5,6-difluoro-benzoimidazol-1-yl]-acetamide. The crude product was purified on a preparative HPLC system (Phenomenex Gemini column) using a gradient of acetonitrile and water (containing 0.5% formic acid). Off-white solid (36%). MS (TS) m/e (M−H)$^-$: 641.2.

Intermediate

N-(4-Cyano-2-trifluoromethyl-phenyl)-2-cyclohexyl-2-[2-(2,6-dimethoxy-pyridin-3-yl)-5,6-difluoro-benzoimidazol-1-yl]-acetamide The title compound was prepared in analogy to example 22, int. d) from cyclohexyl-[2-(2,6-dimethoxy-pyridin-3-yl)-5,6-difluoro-benzoimidazol-1-yl]-acetic acid and 4-amino-3-trifluoromethylbenzonitrile. The crude product was purified on a preparative HPLC system (Phenomenex Gemini column) using a gradient of acetonitrile and water (containing 0.5% formic acid). Light brown foam (19%). MS (TS) (M+H$^+$)$^+$: 600.3.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | | |
|---|---|---|
| Compound of formula (I) | 5.0 | mg |
| Yellow wax | 8.0 | mg |
| Hydrogenated Soya bean oil | 8.0 | mg |
| Partially hydrogenated plant oils | 34.0 | mg |
| Soya bean oil | 110.0 | mg |
| Weight of capsule contents | 165.0 | mg |
| Gelatin capsule | | |
| Gelatin | 75.0 | mg |
| Glycerol 85% | 32.0 | mg |
| Karion 83 | 8.0 | mg (dry matter) |
| Titan dioxide | 0.4 | mg |
| Iron oxide yellow | 1.1 | mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula (I):

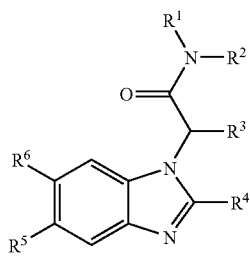

(I)

or a pharmaceutically acceptable salt thereof, wherein:
$R^1$ is selected from the group consisting of:

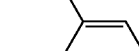

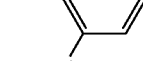

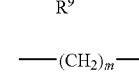

$R^2$ is hydrogen or lower alkyl;
$R^3$ is cyclohexyl or bicyclo[2.2.1]heptyl;
$R^4$ is selected from the group consisting of: (1) phenyl which is substituted at the 4-position by halogen, cyano or fluoro-lower alkyl, and (2) pyridyl which is substituted with 1 or 2 substituents independently selected from the group consisting of halogen, amino, cyano and lower alkoxy;
$R^5$ and $R^6$ independently from each other are hydrogen or fluoro;
$R^7$ and $R^9$ independently from each other are selected from the group consisting of hydrogen, lower alkyl, halogen, lower alkoxy, fluoro-lower alkyl, fluoro-lower alkoxy and cyano;
$R^8$ is selected from the group consisting of: (1) —$(CR^{12}R^{13})_n$—COOH wherein n is 0, 1 or 2 and $R^{12}$ and $R^{13}$ independently from each other are hydrogen or lower alkyl, or $R^{12}$ and $R^{13}$ together with the carbon atom they are attached to form a cycloalkyl ring, and (2) —O—$(CR^{14}R^{15})_p$—COOH wherein p is 1 or 2 and $R^{14}$ and $R^{15}$ independently from each other are hydrogen or lower alkyl, or $R^{14}$ and $R^{15}$ together with the carbon atom they are attached to form a cycloalkyl ring;
$R^{10}$ is hydroxy or —$(CH_2)_p$—COOH wherein p is 0, 1 or 2;
m is 0 or 1; and
$R^{11}$ is —COOH.

2. A compound of formula (I) according to claim 1, wherein $R^8$ is selected from the group consisting of: (1) —$(CR^{12}R^{13})_n$—COOH wherein n is 0, 1 or 2 and $R^{12}$ and $R^{13}$ independently from each other are hydrogen or lower alkyl, and (2) —O—$(CR^{14}R^{15})_p$—COOH wherein p is 1 or 2 and $R^{14}$ and $R^{15}$ independently from each other are hydrogen or lower alkyl.

3. A compound of formula (I) according to claim 1, wherein $R^2$ is hydrogen.

4. A compound of formula (I) according to claim 1 wherein $R^3$ is cyclohexyl.

5. A compound of formula (I) according to claim 1 wherein $R^4$ is phenyl which is substituted at the 4-position by halogen, cyano or fluoro-lower alkyl.

6. A compound of formula (I) according to claim 5 wherein $R^4$ is 4-halogenphenyl.

7. A compound of formula (I) according to claim 6 wherein $R^4$ is 4-chlorophenyl.

8. A compound of formula (I) according to claim 1 wherein $R^4$ is pyridyl which is substituted with 1 or 2 substituents independently selected from the group consisting of halogen, amino, cyano and lower alkoxy.

9. A compound of formula (I) according to claim 8 wherein $R^4$ is pyridin-3-yl which is substituted with 1 or 2 substituents independently selected from the group consisting of halogen, amino, cyano and lower alkoxy.

10. A compound of formula (I) according to claim 1 wherein $R^5$ and $R^6$ are fluoro.

11. A compound of formula (I) according to claim 1 wherein $R^1$ is

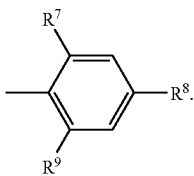

12. A compound of claim 11 wherein $R^8$ is —$(CR^{12}R^{13})_n$—COOH, n is 0, 1 or 2 and $R^{12}$ and $R^{13}$ independently from each other are hydrogen or lower alkyl, or $R^{12}$ and $R^{13}$ together with the carbon atom they are attached to form a cycloalkyl ring.

13. A compound of claim 11 wherein $R^8$ is —COOH.

14. A compound of claim 11 wherein $R^8$ is —O—$(CR^{14}R^{15})_p$—COOH wherein p is 1 or 2 and $R^{14}$ and $R^{15}$ independently from each other are hydrogen or lower alkyl, or $R^{14}$ and $R^{15}$ together with the carbon atom they are attached to form a cycloalkyl ring.

15. A compound of formula (I) according to claim 1 wherein $R^1$ is

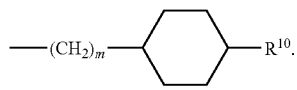

16. A compound of claim 15 wherein $R^{10}$ is hydroxy or —COOH.

17. A compound of claim 16 wherein $R^{10}$ is hydroxy.

18. A compound of formula (I) according to claim 1 wherein $R^1$ is

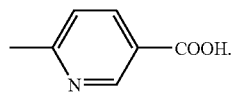

19. A compound of claim 1 selected from the group consisting of:
- 6-{2-[2-(6-chloro-pyridin-3-yl)-5,6-difluoro-benzoimidazol-1-yl]-2-cyclohexyl-acetylamino}-nicotinic acid,
- 3-chloro-4-{2-[2-(6-chloro-pyridin-3-yl)-5,6-difluoro-benzoimidazol-1-yl]-2-cyclohexyl-acetylamino}-benzoic acid,
- 4-{2-[2-(6-chloro-pyridin-3-yl)-5,6-difluoro-benzoimidazol-1-yl]-2-cyclohexyl-acetylamino}-3-fluoro-benzoic acid,
- 4-{2-[2-(6-chloro-pyridin-3-yl)-5,6-difluoro-benzoimidazol-1-yl]-2-cyclohexyl-acetylamino}-3-methyl-benzoic acid,
- (−)-3-chloro-4-{2-[2-(6-chloro-pyridin-3-yl)-5,6-difluoro-benzoimidazol-1-yl]-2-cyclohexyl-acetylamino}-benzoic acid,
- (+)-3-chloro-4-{2-[2-(6-chloro-pyridin-3-yl)-5,6-difluoro-benzoimidazol-1-yl]-2-cyclohexyl-acetylamino}-benzoic acid,
- trans-4-{2-[2-(6-chloro-pyridin-3-yl)-5,6-difluoro-benzoimidazol-1-yl]-2-cyclohexyl-acetylamino}-cyclohexanecarboxylic acid,
- 2-cyclohexyl-2-[2-(2,6-dimethoxy-pyridin-3-yl)-5,6-difluoro-benzoimidazol-1-yl]-N-(4-hydroxy-cyclohexyl)-acetamide,
- (+)-cyclohexyl-2-[2-(2,6-dimethoxy-pyridin-3-yl)-5,6-difluoro-benzoimidazol-1-yl]-N-(trans-4-hydroxy-cyclohexyl)-acetamide,
- trans-4-({cyclohexyl[2-(2,6-dimethoxypyridin-3-yl)-5,6-difluoro-1H-benzimidazol-1-yl]acetyl}amino)cyclohexanecarboxylic acid,
- (+)-4-{2-cyclohexyl-2-[2-(2,6-dimethoxy-pyridin-3-yl)-5,6-difluoro-benzoimidazol-1-yl]-acetylamino}-cyclohexanecarboxylic acid,
- 4-{2-cyclohexyl-2-[2-(2,6-dimethoxy-pyridin-3-yl)-5,6-difluoro-benzoimidazol-1-yl]-acetylamino}-3-methyl-benzoic acid,
- 4-{2-cyclohexyl-2-[2-(2,6-dimethoxy-pyridin-3-yl)-5,6-difluoro-benzoimidazol-1-yl]-acetylamino}-3-fluoro-benzoic acid,
- 4-{2-cyclohexyl-2-[2-(2,6-dimethoxy-pyridin-3-yl)-5-fluoro-benzoimidazol-1-yl]-acetylamino}-cyclohexanecarboxylic acid, and
- (−)-4-{2-cyclohexyl-2-[2-(2,6-dimethoxy-pyridin-3-yl)-5-fluoro-benzoimidazol-1-yl]-acetylamino}-cyclohexanecarboxylic acid, or a pharmaceutically acceptable salt thereof.

20. A compound of claim 1 selected from the group consisting of:
- (−)-4-{2-[2-(4-chloro-phenyl)-5,6-difluoro-benzoimidazol-1-yl]-2-cyclohexyl-acetylamino}-cyclohexanecarboxylic acid,
- (4-{2-[2-(4-chloro-phenyl)-5,6-difluoro-benzoimidazol-1-yl]-2-cyclohexyl-acetylamino}-cyclohexyl)-acetic acid,
- (+)-[trans-4-({2-[2-(4-chlorophenyl)-5,6-difluoro-1H-benzimidazol-1-yl]-2-cyclohexylacetyl}amino)cyclohexyl]acetic acid,
- 4-{2-bicyclo[2.2.1]hept-7-yl-2-[2-(4-chloro-phenyl)-5,6-difluoro-benzoimidazol-1-yl]-acetylamino}-benzoic acid,
- (−)-trans-4-[({2-[2-(4-chlorophenyl)-5-fluoro-1H-benzimidazol-1-yl]-2-cyclohexylacetyl}amino)methyl]cyclohexanecarboxylic acid,
- 3-chloro-4-{2-[2-(4-chloro-phenyl)-5-fluoro-benzoimidazol-1-yl]-2-cyclohexyl-acetylamino}-benzoic acid,
- 4-{2-[2-(4-chloro-phenyl)-5,6-difluoro-benzoimidazol-1-yl]-2-cyclohexyl-acetylamino}-benzoic acid,
- (+)-4-{-2-[2-(4-chloro-phenyl)-5,6-difluoro-benzoimidazol-1-yl]-2-cyclohexyl-acetylamino}-benzoic acid,
- (−)-4-{-2-[2-(4-chloro-phenyl)-5,6-difluoro-benzoimidazol-1-yl]-2-cyclohexyl-acetylamino}-benzoic acid,
- 4-{2-[2-(4-chloro-phenyl)-5,6-difluoro-benzoimidazol-1-yl]-2-cyclohexyl-acetylamino}-3-methyl-benzoic acid,
- (+)-4-{-2-[2-(4-chloro-phenyl)-5,6-difluoro-benzoimidazol-1-yl]-2-cyclohexyl-acetylamino}-3-methyl-benzoic acid,
- (−)-4-{-2-[2-(4-chloro-phenyl)-5,6-difluoro-benzoimidazol-1-yl]-2-cyclohexyl-acetylamino}-3-methyl-benzoic acid,
- 3-chloro-4-{2-[2-(4-chloro-phenyl)-5,6-difluoro-benzoimidazol-1-yl]-2-cyclohexyl-acetylamino}-benzoic acid, (+)-3-chloro-4-{-2-[2-(4-chloro-phenyl)-5,6-difluoro-benzoimidazol-1-yl]-2-cyclohexyl-acetylamino}-benzoic acid, and (−)-3-chloro-4-{-2-[2-(4-chloro-phenyl)-5,6-difluoro-benzoimidazol-1-yl]-2-cyclohexyl-acetylamino}-benzoic acid, or a pharmaceutically acceptable salt thereof.

21. A compound of claim 1 selected from the group consisting of:

4-{2-[2-(4-chloro-phenyl)-5,6-difluoro-benzoimidazol-1-yl]-2-cyclohexyl-acetylamino}-3-fluoro-benzoic acid, (+)-4-{-2-[2-(4-chloro-phenyl)-5,6-difluoro-benzoimidazol-1-yl]-2-cyclohexyl-acetylamino}-3-fluoro-benzoic acid, (−)-4-{-2-[2-(4-chloro-phenyl)-5,6-difluoro-benzoimidazol-1-yl]-2-cyclohexyl-acetylamino}-3-fluoro-benzoic acid, 4-{2-[2-(4-chloro-phenyl)-5,6-difluoro-benzoimidazol-1-yl]-2-cyclohexyl-acetylamino}-3,5-difluoro-benzoic acid, (+)-4-{-2-[2-(4-chloro-phenyl)-5,6-difluoro-benzoimidazol-1-yl]-2-cyclohexyl-acetylamino}-3,5-difluoro-benzoic acid, (−)-4-{-2-[2-(4-chloro-phenyl)-5,6-difluoro-benzoimidazol-1-yl]-2-cyclohexyl-acetylamino}-3,5-difluoro-benzoic acid, 4-{2-[2-(4-chloro-phenyl)-5,6-difluoro-benzoimidazol-1-yl]-2-cyclohexyl-acetylamino}-3-cyano-benzoic acid, 3-chloro-4-{2-[2-(4-chloro-phenyl)-benzoimidazol-1-yl]-2-cyclohexyl-acetylamino}-benzoic acid, (+)-3-chloro-4-{-2-[2-(4-chloro-phenyl)-benzoimidazol-1-yl]-2-cyclohexyl-acetylamino}-benzoic acid, (−)-3-chloro-4-{-2-[2-(4-chloro-phenyl)-benzoimidazol-1-yl]-2-cyclohexyl-acetylamino}-benzoic acid, 4-{2-[2-(4-chloro-phenyl)-5,6-difluoro-benzoimidazol-1-yl]-2-cyclohexyl-acetylamino}-3-methoxy-benzoic acid, 4-{2-[2-(4-chloro-phenyl)-5,6-difluoro-benzoimidazol-1-yl]-2-cyclohexyl-acetylamino}-3-trifluoromethyl-benzoic acid, 4-{2-cyclohexyl-2-[5,6-difluoro-2-(4-trifluoromethyl-phenyl)-benzoimidazol-1-yl]-acetylamino}-benzoic acid, 4-{2-cyclohexyl-2-[5-fluoro-2-(4-trifluoromethyl-phenyl)-benzoimidazol-1-yl]-acetylamino}-benzoic acid, and 4-{2-[2-(4-chloro-phenyl)-5,6-difluoro-benzoimidazol-1-yl]-2-cyclohexyl-acetylamino}-3-trifluoromethoxy-benzoic acid, or a pharmaceutically acceptable salt thereof.

22. A compound of claim 1 selected from the group consisting of:

4-{2-[2-(4-chloro-phenyl)-5-fluoro-benzoimidazol-1-yl]-2-cyclohexyl-acetylamino}-benzoic acid, 4-{2-[2-(4-chloro-phenyl)-5-fluoro-benzoimidazol-1-yl]-2-cyclohexyl-acetylamino}-3-fluoro-benzoic acid, (4-{2-[2-(4-chloro-phenyl)-5,6-difluoro-benzoimidazol-1-yl]-2-cyclohexyl-acetylamino}-phenyl)-acetic acid, 2-(4-{2-[2-(4-chloro-phenyl)-5,6-difluoro-benzoimidazol-1-yl]-2-cyclohexyl-acetylamino}-3-fluoro-phenyl)-propionic acid, 2-(4-{2-[2-(4-chloro-phenyl)-5,6-difluoro-benzoimidazol-1-yl]-2-cyclohexyl-acetylamino}-3-fluoro-phenyl)-2-methyl-propionic acid, 3-(4-{2-[2-(4-chloro-phenyl)-5,6-difluoro-benzoimidazol-1-yl]-2-cyclohexyl-acetylamino}-phenyl)-propionic acid, 3-(4-{2-[2-(4-chloro-phenyl)-5,6-difluoro-benzoimidazol-1-yl]-2-cyclohexyl-acetylamino}-3-fluoro-phenyl)-propionic acid, (−)-3-(4-{2-[2-(4-chloro-phenyl)-5,6-difluoro-benzoimidazol-1-yl]-2-cyclohexyl-acetylamino}-3-fluoro-phenyl)-propionic acid, (+)-3-(4-{2-[2-(4-chloro-phenyl)-5,6-difluoro-benzoimidazol-1-yl]-2-cyclohexyl-acetylamino}-3-fluoro-phenyl)-propionic acid, (4-{2-[2-(4-chloro-phenyl)-5,6-difluoro-benzoimidazol-1-yl]-2-cyclohexyl-acetylamino}-3-fluoro-phenoxy)-acetic acid, 2-(4-{2-[2-(4-chloro-phenyl)-5,6-difluoro-benzoimidazol-1-yl]-2-cyclohexyl-acetylamino}-3-fluoro-phenoxy)-propionic acid, 2-(4-{2-[2-(4-chloro-phenyl)-5,6-difluoro-benzoimidazol-1-yl]-2-cyclohexyl-acetylamino}-3-fluoro-phenoxy)-2-methyl-propionic acid, (+)-2-(4-{-2-[2-(4-chloro-phenyl)-5,6-difluoro-benzoimidazol-1-yl]-2-cyclohexyl-acetylamino}-3-fluoro-phenoxy)-2-methyl-propionic acid, (−)-2-(4-{-2-[2-(4-chloro-phenyl)-5,6-difluoro-benzoimidazol-1-yl]-2-cyclohexyl-acetylamino}-3-fluoro-phenoxy)-2-methyl-propionic acid, and 1-(4-{2-[2-(4-chloro-phenyl)-5,6-difluoro-benzoimidazol-1-yl]-2-cyclohexyl-acetylamino}-3-fluoro-phenoxy)-cyclopropanecarboxylic acid, or a pharmaceutically acceptable salt thereof.

23. A compound of claim 1 selected from the group consisting of:

(+)-1-(4-{-2-[2-(4-chloro-phenyl)-5,6-difluoro-benzoimidazol-1-yl]-2-cyclohexyl-acetylamino}-3-fluoro-phenoxy)-cyclopropanecarboxylic acid, (−)-1-(4-{-2-[2-(4-chloro-phenyl)-5,6-difluoro-benzoimidazol-1-yl]-2-cyclohexyl-acetylamino}-3-fluoro-phenoxy)-cyclopropanecarboxylic acid, 2-[2-(4-chloro-phenyl)-5,6-difluoro-benzoimidazol-1-yl]-2-cyclohexyl-N-trans-(4-hydroxy-cyclohexyl)-acetamide, (−)-2-[2-(4-chloro-phenyl)-5,6-difluoro-benzoimidazol-1-yl]-2-cyclohexyl-N-(4-hydroxy-cyclohexyl)-acetamide, (+)-2-[2-(4-chloro-phenyl)-5,6-difluoro-benzoimidazol-1-yl]-2-cyclohexyl-N-(4-hydroxy-cyclohexyl)-acetamide, 6-{2-[2-(4-chloro-phenyl)-5,6-difluoro-benzoimidazol-1-yl]-2-cyclohexyl-acetylamino}-nicotinic acid, (+)-4-{2-[2-(4-Chloro-phenyl)-5,6-difluoro-benzoimidazol-1-yl]-2-cyclohexyl-acetylamino}-3-cyano-benzoic acid, (−)4-{2-[2-(4-Chloro-phenyl)-5,6-difluoro-benzoimidazol-1-yl]-2-cyclohexyl-acetylamino}-3-cyano-benzoic acid, (+)-4-{2-[2-(4-Chloro-phenyl)-5,6-difluoro-benzoimidazol-1-yl]-2-cyclohexyl-acetylamino}-3-methoxy-benzoic acid, (−)-4-{2-[2-(4-Chloro-phenyl)-5,6-difluoro-benzoimidazol-1-yl]-2-cyclohexyl-acetylamino}-3-methoxy-benzoic acid, (+)-4-{2-[2-(4-Chloro-phenyl)-5,6-difluoro-benzoimidazol-1-yl]-2-cyclohexyl-acetylamino}-3-trifluoromethyl-benzoic acid, (−)-4-{2-[2-(4-Chloro-phenyl)-5,6-difluoro-benzoimidazol-1-yl]-2-cyclohexyl-acetylamino}-3-trifluoromethyl-benzoic acid, (+)-4-{2-[2-(4-Chloro-phenyl)-5,6-difluoro-benzoimidazol-1-yl]-2-cyclohexyl-acetylamino}-3-trifluoromethoxy-benzoic acid,
(−)-4-{2-[2-(4-Chloro-phenyl)-5,6-difluoro-benzoimidazol-1-yl]-2-cyclohexyl-acetylamino}-3-trifluoromethoxy-benzoic acid, and
(−)-4-{2-[2-(4-Chloro-phenyl)-5-fluoro-benzoimidazol-1-yl]-2-cyclohexyl-acetylamino}-3-fluoro-benzoic acid, or a pharmaceutically acceptable salt thereof.

24. A compound of claim 1 selected from the group consisting of:
- (+)-4-{2-[2-(4-Chloro-phenyl)-5-fluoro-benzoimidazol-1-yl]-2-cyclohexyl-acetylamino}-3-fluoro-benzoic acid,
- 4-{2-[2-(4-Chloro-phenyl)-5,6-difluoro-benzoimidazol-1-yl]-2-cyclohexyl-acetylamino}-3-cyano-5-fluoro-benzoic acid,
- (+)-4-{2-[2-(4-Chloro-phenyl)-5,6-difluoro-benzoimidazol-1-yl]-2-cyclohexyl-acetylamino}-3-cyano-5-fluoro-benzoic acid,
- (−)-4-{2-[2-(4-Chloro-phenyl)-5,6-difluoro-benzoimidazol-1-yl]-2-cyclohexyl-acetylamino}-3-cyano-5-fluoro-benzoic acid,
- 1-(4-{2-[2-(4-Chloro-phenyl)-benzoimidazol-1-yl]-2-cyclohexyl-acetylamino}-3-fluoro-phenoxy)-cyclopropanecarboxylic acid,
- (+)-1-(4-{2-[2-(4-Chloro-phenyl)-benzoimidazol-1-yl]-2-cyclohexyl-acetylamino}-3-fluoro-phenoxy)-cyclopropanecarboxylic acid,
- (−)-1-(4-{2-[2-(4-Chloro-phenyl)-benzoimidazol-1-yl]-2-cyclohexyl-acetylamino}-3-fluoro-phenoxy)-cyclopropanecarboxylic acid,
- 4-{2-[2-(4-Chloro-phenyl)-benzoimidazol-1-yl]-2-cyclohexyl-acetylamino}-3-trifluoromethyl-benzoic acid,
- (+)-4-{2-[2-(4-Chloro-phenyl)-benzoimidazol-1-yl]-2-cyclohexyl-acetylamino}-3-trifluoromethyl-benzoic acid,
- (−)-4-{2-[2-(4-Chloro-phenyl)-benzoimidazol-1-yl]-2-cyclohexyl-acetylamino}-3-trifluoromethyl-benzoic acid,
- 4-{2-Cyclohexyl-2-[5,6-difluoro-2-(6-methoxy-pyridin-3-yl)-benzoimidazol-1-yl]-acetylamino}-cyclohexanecarboxylic acid,
- (−)-4-{2-[2-(6-Chloro-pyridin-3-yl)-5,6-difluoro-benzoimidazol-1-yl]-2-cyclohexyl-acetylamino}-cyclohexanecarboxylic acid,
- (4-{2-[2-(6-Chloro-2-methoxy-pyridin-3-yl)-5,6-difluoro-benzoimidazol-1-yl]-2-cyclohexyl-acetylamino}-cyclohexyl)-acetic acid,
- 4-{2-[2-(6-Chloro-2-methoxy-pyridin-3-yl)-5,6-difluoro-benzoimidazol-1-yl]-2-cyclohexyl-acetylamino}-cyclohexanecarboxylic acid, and
- 4-{2-[2-(6-Chloro-2-methoxy-pyridin-3-yl)-5,6-difluoro-benzoimidazol-1-yl]-2-cyclohexyl-acetylamino}-benzoic acid, or a pharmaceutically acceptable salt thereof.

25. A compound of claim 1 selected from the group consisting of:
- (+)-4-{2-Cyclohexyl-2-[5,6-difluoro-2-(6-methoxy-pyridin-3-yl)-benzoimidazol-1-yl]-acetylamino}-cyclohexanecarboxylic acid,
- (−)-4-{2-[2-(6-Chloro-2-methoxy-pyridin-3-yl)-5,6-difluoro-benzoimidazol-1-yl]-2-cyclohexyl-acetylamino}-cyclohexanecarboxylic acid,
- (−)-(4-{2-[2-(6-Chloro-2-methoxy-pyridin-3-yl)-5,6-difluoro-benzoimidazol-1-yl]-2-cyclohexyl-acetylamino}-cyclohexyl)-acetic acid,
- (+)-4-{(S)-2-[2-(6-Chloro-2-methoxy-pyridin-3-yl)-5,6-difluoro-benzoimidazol-1-yl]-2-cyclohexyl-acetylamino}-benzoic acid,
- 4-{2-Bicyclo[2.2.1]hept-7-yl-2-[2-(4-chloro-phenyl)-5,6-difluoro-benzoimidazol-1-yl]-acetylamino}-benzoic acid,
- (4-{2-Cyclohexyl-2-[5,6-difluoro-2-(2-methoxy-pyridin-3-yl)-benzoimidazol-1-yl]-acetylamino}-cyclohexyl)-acetic acid,
- 4-[2-Cyclohexyl-2-(5,6-difluoro-2-p-tolyl-benzoimidazol-1-yl)-acetylamino]-benzoic acid
- 4-[2-Cyclohexyl-2-(5,6-difluoro-2-p-tolyl-benzoimidazol-1-yl)-acetylamino]-cyclohexanecarboxylic acid,
- (−)-4-[2-Cyclohexyl-2-(5,6-difluoro-2-p-tolyl-benzoimidazol-1-yl)-acetylamino]-benzoic acid,
- (+)-[2-Cyclohexyl-2-(5,6-difluoro-2-p-tolyl-benzoimidazol-1-yl)-acetylamino]-cyclohexanecarboxylic acid,
- 4-{2-Bicyclo[2.2.1]hept-7-yl-2-[2-(4-chloro-phenyl)-5,6-difluoro-benzoimidazol-1-yl]-acetylamino}-cyclohexanecarboxylic acid,
- 4-{2-Cyclohexyl-2-[5,6-difluoro-2-(4-methoxy-phenyl)-benzoimidazol-1-yl]-acetylamino}-benzoic acid,
- (−)-4-{2-Bicyclo[2.2.1]hept-7-yl-2-[2-(4-chloro-phenyl)-5,6-difluoro-benzoimidazol-1-yl]-acetylamino}-cyclohexanecarboxylic acid,
- 4-{2-Cyclohexyl-2-[5,6-difluoro-2-(4-methoxy-phenyl)-benzoimidazol-1-yl]-acetylamino}-cyclohexanecarboxylic acid, and
- (−)-4-{2-Cyclohexyl-2-[5,6-difluoro-2-(4-methoxy-phenyl)-benzoimidazol-1-yl]-acetylamino}-benzoic acid, or a pharmaceutically acceptable salt thereof.

26. A compound of claim 1 selected from the group consisting of:
- (4-{2-Bicyclo[2.2.1]hept-7-yl-2-[2-(4-chloro-phenyl)-5,6-difluoro-benzoimidazol-1-yl]-acetylamino}-cyclohexyl)-acetic acid,
- (−)-4-{2-Bicyclo[2.2.1]hept-7-yl-2-[2-(4-chloro-phenyl)-5,6-difluoro-benzoimidazol-1-yl]-acetylamino}-benzoic acid, and
- (−)-(4-{2-Bicyclo[2.2.1]hept-7-yl-2-[2-(4-chloro-phenyl)-5,6-difluoro-benzoimidazol-1-yl]-acetylamino}-cyclohexyl)-acetic acid, or a pharmaceutically acceptable salt thereof.

27. A compound of claim 1 selected from the group consisting of:
- 2-cyclohexyl-2-[2-(2,6-dimethoxy-pyridin-3-yl)-5,6-difluoro-benzoimidazol-1-yl]-N-(4-hydroxy-cyclohexyl)-acetamide,
- (+)-2-cyclohexyl-2-[2-(2,6-dimethoxy-pyridin-3-yl)-5,6-difluoro-benzoimidazol-1-yl]-N-(trans-4-hydroxy-cyclohexyl)-acetamide,
- (−)-2-[2-(4-chloro-phenyl)-5,6-difluoro-benzoimidazol-1-yl]-2-cyclohexyl-N-(4-hydroxy-cyclohexyl)-acetamide, and
- (+)-2-[2-(4-chloro-phenyl)-5,6-difluoro-benzoimidazol-1-yl]-2-cyclohexyl-N-(4-hydroxy-cyclohexyl)-acetamide, or a pharmaceutically acceptable salt thereof.

28. A compound of claim 1 selected from the group consisting of:
- 4-{2-[2-(4-chloro-phenyl)-5,6-difluoro-benzoimidazol-1-yl]-2-cyclohexyl-acetylamino}-benzoic acid,
- (−)-4-{-2-[2-(4-chloro-phenyl)-5,6-difluoro-benzoimidazol-1-yl]-2-cyclohexyl-acetylamino}-benzoic acid, 4-{2-[2-(4-chloro-phenyl)-5,6-difluoro-benzoimidazol-1-yl]-2-cyclohexyl-acetylamino}-3-fluoro-benzoic acid, and (−)-4-{-2-[2-(4-chloro-phenyl)-5,6-difluoro-benzoimidazol-1-yl]-2-cyclohexyl-acetylamino}-3-fluoro-benzoic acid, or a pharmaceutically acceptable salt thereof.

29. A compound of claim 1 selected from the group consisting of:

2-(4-{2-[2-(4-chloro-phenyl)-5,6-difluoro-benzoimidazol-1-yl]-2-cyclohexyl-acetylamino}-3-fluoro-phenoxy)-2-methyl-propionic acid, (−)-2-(4-{-2-[2-(4-chloro-phenyl)-5,6-difluoro-benzoimidazol-1-yl]-2-cyclohexyl-acetylamino}-3-fluoro-phenoxy)-2-methyl-propionic acid, 1-(4-{2-[2-(4-chloro-phenyl)-5,6-difluoro-benzoimidazol-1-yl]-2-cyclohexyl-acetylamino}-3-fluoro-phenoxy)-cyclopropanecarboxylic acid, and (−)-1-(4-{-2-[2-(4-chloro-phenyl)-5,6-difluoro-benzoimidazol-1-yl]-2-cyclohexyl-acetylamino}-3-fluoro-phenoxy)-cyclopropanecarboxylic acid, or a pharmaceutically acceptable salt thereof.

30. A compound of claim 1 selected from the group consisting of:

(−)4-{2-[2-(4-Chloro-phenyl)-5,6-difluoro-benzoimidazol-1-yl]-2-cyclohexyl-acetylamino}-3-cyano-benzoic acid, (−)-4-{2-[2-(4-Chloro-phenyl)-5,6-difluoro-benzoimidazol-1-yl]-2-cyclohexyl-acetylamino}-3-trifluoromethyl-benzoic acid, (−)-4-{2-[2-(4-Chloro-phenyl)-5,6-difluoro-benzoimidazol-1-yl]-2-cyclohexyl-acetylamino}-3-cyano-5-fluoro-benzoic acid, and (−)-4-{2-[2-(4-Chloro-phenyl)-benzoimidazol-1-yl]-2-cyclohexyl-acetylamino}-3-trifluoromethyl-benzoic acid, or a pharmaceutically acceptable salt thereof.

31. A pharmaceutical composition comprising a therapeutically effective amount of a compound of formula (I) according to claim 1 and a pharmaceutically acceptable carrier and/or adjuvant.

32. A compound selected from the group consisting of:

2-[2-(4-Chloro-phenyl)-5,6-difluoro-benzoimidazol-1-yl]-2-cyclohexyl-N-[4-(1H-tetrazol-5-yl)-phenyl]-acetamide, 2-[2-(4-Chloro-phenyl)-5,6-difluoro-benzoimidazol-1-yl]-N-[2-chloro-4-(1H-tetrazol-5-yl)-phenyl]-2-cyclohexyl-acetamide, 2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide, (+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide, (+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide, 2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide, (+)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide, (−)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide, 2-[2-(4-Chloro-phenyl)-benzoimidazol-1-yl]-2-cyclohexyl-N-[4-(1H-tetrazol-5-yl)-2-trifluoromethyl-phenyl]-acetamide, (+)-2-[2-(4-Chloro-phenyl)-benzoimidazol-1-yl]-2-cyclohexyl-N-[4-(1H-tetrazol-5-yl)-2-trifluoromethyl-phenyl]-acetamide, (−)-2-[2-(4-Chloro-phenyl)-benzoimidazol-1-yl]-2-cyclohexyl-N-[4-(1H-tetrazol-5-yl)-2-trifluoromethyl-phenyl]-acetamide, 2-Cyclohexyl-2-[2-(2,6-dimethoxy-pyridin-3-yl)-5,6-difluoro-benzoimidazol-1-yl]-N-[2-fluoro-4-(1H-tetrazol-5-yl)-phenyl]-acetamide, 2-Cyclohexyl-2-[2-(2,6-dimethoxy-pyridin-3-yl)-5,6-difluoro-benzoimidazol-1-yl]-N-[4-(1H-tetrazol-5-yl)-2-trifluoromethyl-phenyl]-acetamide, (+ or −)-2-[2-(4-Chloro-phenyl)-5,6-difluoro-benzoimidazol-1-yl]-2-cyclohexyl-N-[2-fluoro-4-(1H-tetrazol-5-yl)-phenyl]-acetamide, (−)-2-[2-(4-Chloro-phenyl)-5,6-difluoro-benzoimidazol-1-yl]-2-cyclohexyl-N-[4-(1H-tetrazol-5-yl)-2-trifluoromethyl-phenyl]-acetamide, and (−)-2-[2-(4-Chloro-phenyl)-benzoimidazol-1-yl]-2-cyclohexyl-N-[4-(1H-tetrazol-5-yl)-2-trifluoromethyl-phenyl]-acetamide, or a pharmaceutically acceptable salt thereof.

* * * * *